(12) United States Patent
Van Ooijen et al.

(10) Patent No.: US 11,640,845 B2
(45) Date of Patent: May 2, 2023

(54) BIOINFORMATICS PROCESS FOR IDENTIFYING AT RISK SUBJECT POPULATIONS

(71) Applicant: KONINKLIJKE PHILIPS N.V., Eindhoven (NL)

(72) Inventors: Hendrik Jan Van Ooijen, Eindhoven (NL); Wilhelmus Franciscus Johannes Verhaegh, Eindhoven (NL); Anne Godefrida Catharina Van Brussel, Eindhoven (NL); Janneke Wrobel, Eindhoven (NL); Robert Van Gog, Eindhoven (NL)

(73) Assignee: KONINKLIJKE PHILIPS N.V., Eindhoven (NL)

(\*) Notice: Subject to any disclaimer, the term of this patent is extended or adjusted under 35 U.S.C. 154(b) by 1000 days.

(21) Appl. No.: 14/922,506

(22) Filed: Oct. 26, 2015

(65) Prior Publication Data
US 2016/0117443 A1    Apr. 28, 2016

(30) Foreign Application Priority Data
Oct. 24, 2014  (EP) .................................... 14190273

(51) Int. Cl.
  *G16B 5/00* (2019.01)
  *G16B 25/10* (2019.01)
  (Continued)

(52) U.S. Cl.
  CPC ............. *G16B 5/20* (2019.02); *C12Q 1/6883* (2013.01); *C12Q 1/6886* (2013.01); *G16B 5/00* (2019.02);
  (Continued)

(58) Field of Classification Search
  None
  See application file for complete search history.

(56) References Cited

U.S. PATENT DOCUMENTS 5,436,134 A   7/1995 Haugland
5,476,928 A   12/1995 Ward
(Continued)

FOREIGN PATENT DOCUMENTS

WO   2012154567 A2   11/2012
WO   2013003384 A1   1/2013
(Continued)

OTHER PUBLICATIONS

Teschendorff et al. Improved prognostic classification of breast cancer defined by antagonistic activation patterns of immune response pathway modules BMC Cancer 2010, 10:604, pp. 1-20 (Year: 2010).*
(Continued)

*Primary Examiner* — Olivia M. Wise

(57) ABSTRACT

A bioinformatics method for determining a risk score that indicates a risk that a subject will experience a negative clinical event within a certain period of time. The risk score is based on a combination of activities of two or more cellular signaling pathways in a subject, such as a human, wherein the specific cellular signaling pathways are the PI3K pathway and one or more of a Wnt pathway, an ER pathway, and an HH pathway. The invention also includes an apparatus with a digital processor configured to perform such a method, to a non-transitory storage medium storing instructions that are executable by a digital processing device to perform such a method, and to a computer program comprising program code means for causing a digital processing device to perform such a method. The invention achieves advanced prognosis of negative clinical events, for example, disease progression, recurrence, development of metastasis, or even death.

7 Claims, 15 Drawing Sheets

Specification includes a Sequence Listing.

(51) Int. Cl.
| | |
|---|---|
| *G16H 50/20* | (2018.01) |
| *G16H 50/30* | (2018.01) |
| *G16B 5/20* | (2019.01) |
| *G16B 30/00* | (2019.01) |
| *G16B 20/00* | (2019.01) |
| *G16B 20/30* | (2019.01) |
| *G16B 20/20* | (2019.01) |
| *C12Q 1/6883* | (2018.01) |
| *C12Q 1/6886* | (2018.01) |

(52) U.S. Cl.
CPC ............ *G16B 20/00* (2019.02); *G16B 20/20* (2019.02); *G16B 20/30* (2019.02); *G16B 25/10* (2019.02); *G16B 30/00* (2019.02); *G16H 50/20* (2018.01); *G16H 50/30* (2018.01); *C12Q 2600/112* (2013.01); *C12Q 2600/118* (2013.01); *C12Q 2600/158* (2013.01); *C12Q 2600/16* (2013.01)

(56) References Cited

U.S. PATENT DOCUMENTS

| | | |
|---|---|---|
| 5,658,751 A | 8/1997 | Yue |
| 5,874,219 A | 2/1999 | Rava |
| 5,958,691 A | 9/1999 | Pieken |
| 6,004,761 A | 12/1999 | Linsley |
| 6,146,897 A | 11/2000 | Cohenford |
| 6,171,798 B1 | 1/2001 | Levine |
| 6,225,047 B1 | 5/2001 | Hutchens |
| 6,308,170 B1 | 10/2001 | Balaban |
| 6,391,550 B1 | 5/2002 | Lockhart |
| 6,675,104 B2 | 1/2004 | Paulse |
| 6,720,149 B1 | 4/2004 | Rava |
| 6,844,165 B2 | 1/2005 | Hutchens |
| 6,884,578 B2 | 4/2005 | Warrington |
| 7,056,674 B2 | 6/2006 | Baker |
| 7,081,340 B2 | 7/2006 | Baker |
| 7,160,734 B2 | 1/2007 | Hutchens |
| 7,208,470 B2 | 4/2007 | Duan |
| 7,299,134 B2 | 11/2007 | Rich |
| 7,526,637 B2 | 4/2009 | Jung |
| 7,569,345 B2 | 8/2009 | Cobleigh |
| 7,695,913 B2 | 4/2010 | Cowens |
| 7,723,033 B2 | 5/2010 | Baker |
| 7,754,431 B2 | 7/2010 | Ring |
| 7,754,861 B2 | 7/2010 | Boschetti |
| 7,816,084 B2 | 10/2010 | Ring |
| 7,838,224 B2 | 11/2010 | Baker |
| 7,858,304 B2 | 12/2010 | Baker |
| 7,888,019 B2 | 2/2011 | Kiefer |
| 7,930,104 B2 | 4/2011 | Baker |
| 7,939,261 B2 | 5/2011 | Baker |
| 8,008,003 B2 | 8/2011 | Baker |
| 8,021,894 B2 | 9/2011 | Hutchens |
| 8,026,060 B2 | 9/2011 | Watson |
| 8,029,995 B2 | 10/2011 | Watson |
| 8,029,997 B2 | 10/2011 | Kennedy |
| 8,034,565 B2 | 10/2011 | Cobleigh |
| 8,067,178 B2 | 11/2011 | Baker |
| 8,071,286 B2 | 12/2011 | Baker |
| 8,148,076 B2 | 4/2012 | Baker |
| 8,153,378 B2 | 4/2012 | Cowens |
| 8,153,379 B2 | 4/2012 | Watson |
| 8,153,380 B2 | 4/2012 | Watson |
| 8,198,024 B2 | 6/2012 | Watson |
| 8,206,919 B2 | 6/2012 | Cobleigh |
| 8,273,537 B2 | 9/2012 | Watson |
| 8,367,345 B2 | 2/2013 | Cowens |
| 8,451,450 B2 | 5/2013 | Heng |
| 8,518,639 B2 | 8/2013 | Rihet |
| 8,632,980 B2 | 1/2014 | Baker |
| 8,703,736 B2 | 4/2014 | Whatcott |
| 8,725,426 B2 | 5/2014 | Shak |
| 8,741,605 B2 | 6/2014 | Cobleigh |
| 8,765,383 B2 | 7/2014 | Cowens |
| 8,808,994 B2 | 8/2014 | Kiefer |
| 8,868,352 B2 | 10/2014 | Baker |
| 8,906,625 B2 | 12/2014 | Kiefer |
| 8,911,940 B2 | 12/2014 | Weiss |
| 9,076,104 B2 | 7/2015 | Wang |
| 2006/0234911 A1 | 10/2006 | Hoffmann |
| 2009/0186024 A1* | 7/2009 | Nevins ................ C12Q 1/6886 424/134.1 |
| 2010/0131432 A1 | 5/2010 | Kennedy |
| 2010/0285980 A1 | 11/2010 | Shak |
| 2011/0053804 A1 | 3/2011 | Massague |
| 2011/0129833 A1 | 6/2011 | Baker |
| 2012/0009581 A1 | 1/2012 | Bankaitis-Davis |
| 2014/0339597 A1 | 11/2014 | Schiaffino |

FOREIGN PATENT DOCUMENTS

| | | |
|---|---|---|
| WO | 2013011479 A2 | 1/2013 |
| WO | 2013075059 A1 | 5/2013 |
| WO | 2014102668 A2 | 7/2014 |
| WO | 2014174003 A1 | 10/2014 |
| WO | 2015101635 A1 | 7/2015 |

OTHER PUBLICATIONS

Weigelt et al. Genomic determinants of PI3K pathway inhibitor response in cancer. Frontiers in Oncology, Aug. 2012, vol. 2, Article 109, pp. 1-16 (Year: 2012).*
Howe et al. Wnt Signaling and Breast Cancer. Cancer Biology & Therapy Jan. 2004, 3:1, pp. 36-41 (Year: 2004).*
Mohinta et al. Wnt pathway and breast cancer. Frontiers in Bioscience May 2007, 12, pp. 4020-4033 (Year: 2007).*
Chen et al. Constitutively Nuclear FOXO3a localization predicts poor survival and promotes Akt phosphorylation in breast cancer. PLoS One Aug. 2010, vol. 5, Issue 8, e12293, pp. 1-17 (Year: 2010).*
Li et al. The expression of beta-catenin in different subtypes of breast cancer and its clinical significance. Tumor Biol May 8, 2014, 35:7693-7698 (Year: 2014).*
Zellmer, Victoria et al "Evolving Concepts of Tumor Heterogeneity" Cell & Bioscience 2014.
Chen, Min et al "A Powerful Bayesian Meta-Analysis Method to Integrate Multiple Gene Set Enrichment Studies", Bioinformatic, vol. 29, No. 7, 2013, pp. 862-869.
Fanelli, Laise P. et al "Modeling TGF-Beta Signaling Pathway in Epithelial-Mesenchymal Transistion", AIP Advances, 2012, vol. 2, No. 1. Abstract Only.
Zhang, Ping et al "Joint Loading-Driven Bone Formation and Signaling Pathways Predicted from Genome-Wide Expression Profiles", Sciencedirect—Bone, vol. 44, 2009, pp. 989-998.
Fan, C. et al "Concordance Among Gene Expression Based Predictors for Breast Cancer" The New England Journal of Medicine, vol. 355, 2006.
Paik, S. et al "A Multigene Assay to Predict Recurrence of Tamoxifen treated, Node-Negatve Breast Cancer", The New England Journal of Medicine, vol. 351, 2004.
Nout, Remi A. "Improved Risk Assessment of Endometrial Cancer by Combined Analysis of MSI, PI3K-AKT, Wnt/Beta Catenin and P53 Pathway Activation", Gynecologic Oncology, vol. 126, 2012.
Vadlakonda, Kakshmipathi et al "Role of PI3K-AKT-mTOR and Wnt Signaling Pathways in Transition of G1-S Phase of Cell Cycle in Cancer Cells", Perspecirive Article Frontiers in Oncology, 2013.
Van De Stolpe, Anja et al "RNA Based Approaches to Profile Oncogenic Pathways from Low Quantity Samples to Drive Precision Oncology Strategies", Methods, Frontiers in Genetics, vol. 11, Feb. 2021.
Verhaegh, Wim et al "Knowledge-based Computational Models", Oncotarget, vol. 5, No. 14, 2014.
Verhaegh, Wim et al, "Selection of Personalized Patient Therapy through the use of Knowledge-Based Computational Models that Identify Tumor-Driving Signal Transduction Pathways", Cancer Research, Integrated Systems and Technologies: Mathematical Oncology, vol. 74, No. 11, Jun. 2014.

(56) References Cited

OTHER PUBLICATIONS

"Measuring Functional Activity of Signal Transduction Pathways from target Gene mRNA Levels", Philips Molecular Pathway DX, Oct. 2020.

Van Ooijen, Henk et al "Assessment of Functional Phosphatidylinositol 3-Kinase Pathway Activity in Cancer Tissue using Forkhead Box-0 Target Gene Expression in a Knowledge-Based Computational model", The American Journal of Pathology, vol. 188, No. 9, Sep. 2018.

Van Ooijen, Henk et al "Prognosis within Different Breast Cancer Subtypes using Functional Activity of Signaling Pathways", Philips Research, 2015.

\* cited by examiner

BIOINFORMATICS PROCESS FOR IDENTIFYING AT RISK SUBJECT POPULATIONS

RELATED APPLICATIONS

This application claims the benefit of European Patent Application No. EP14190273.4, filed Oct. 24, 2014, the entirety of the specification and claims thereof is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 2014PF00610_2015-10-26_SequenceListing_ST25.txt. The text file is 796 KB, was created on Oct. 26, 2015, and is being submitted electronically via EFS-Web.

FIELD

The present disclosure is in the field of systems biology, bioinformatics, genomic mathematical processing, and proteomic mathematical processing. In particularly, the present disclosure is a method for identifying a subject at risk of experiencing a clinical event associated with a disease or disorder within a certain period of time based on the evaluation of two or more cellular signaling pathway activities in a subject, wherein the cellular signaling pathways comprise a a PI3K pathway, and one or more of a Wnt pathway, an ER pathway, and an HH pathway. The present application also includes an apparatus with a digital processor configured to perform such a method, to a non-transitory storage medium storing instructions that are executable by a digital processing device to perform such a method, and to a computer program comprising program code means for causing a digital processing device to perform such a method. The present disclosure further includes kits for measuring expression levels for the unique combinations of target genes.

BACKGROUND

As knowledge of tumors including cancers evolve, it becomes more clear that they are extraordinarily heterogeneous and multifactorial. Tumors and cancers have a wide range of genotypes and phenotypes, they are influenced by their individualized cell receptors (or lack thereof), microenvironment, extracellular matrix, tumor vascularization, neighboring immune cells, and accumulations of mutations, with differing capacities for proliferation, migration, stem cell properties and invasion. This scope of heterogeneity exists even among same classes of tumors. See generally: Nature Insight: Tumor Heterogeneity (entire issue of articles), 19 Sep. 2013 (Vol. 501, Issue 7467); Zellmer and Zhang, "Evolving concepts of tumor heterogeneity". Cell and Bioscience 2014, 4:69.

Traditionally, physicians have treated tumors, including cancers, as the same within class type (including within receptor type) without taking into account the enormous fundamental individualized nature of the diseased tissue. Patients have been treated with available chemotherapeutic agents based on class and receptor type, and if they do not respond, they are treated with an alternative therapeutic, if it exists. This is an empirical approach to medicine.

There has been a growing trend toward taking into account the heterogeneity of tumors at a more fundamental level as a means to create individualized therapies, however, this trend is still in its formative stages. What is desperately needed are approaches to obtain more metadata about the tumor to inform therapeutic treatment in a manner that allows the prescription of approaches more closely tailored to the individual tumor, and perhaps more importantly, avoiding therapies destined to fail and waste valuable time, which can be life-determinative.

The Wnt signaling pathway affects cell proliferation and is highly regulated. High Wnt pathway activity due to loss of regulation has been associated with the development and advancement of certain disease, for example cancer and the development of malignant colon tumors. It is believed that deregulation of the Wnt pathway in malignant colon cells leads to high Wnt pathway activity that in turn causes cell proliferation of the malignant colon cells, i.e., spread of colon cancer. On the other hand, abnormally low pathway activity might also be of interest, for example in the case of osteoporosis. Other pathways which play roles in cell division, function and/or differentiation in health and disease are cellular signaling pathways such as ER. PR, AR, PPAR, GR, VitD, TGF-β, Notch, Hedgehog, FGF, NFkB, VEGF, and PDGF.

Certain technologies for acquiring traditional genomic and proteomic data are available in clinical settings. For example, measurements by microarrays are employed to assess gene expression levels, protein levels, methylation, and so forth. Automated gene sequencing enables cost-effective identification of genetic variations/mutations/abnormal methylation patterns in DNA and mRNA. Quantitative assessment of mRNA levels during gene sequencing holds promise as a clinical tool for assessing gene expression levels.

A number of companies and institutions are active in the area of traditional, and some more advanced, genetic testing, diagnostics, and predictions for the development of human diseases, including, for example: Affymetrix, Inc.; Bio-Rad, Inc; Roche Diagnostics; Genomic Health. Inc.; Regents of the University of California; Illumina; Fluidigm Corporation: Sequenom, Inc.; High Throughput Genomics; NanoString Technologies: Thermo Fisher; Danaher; Becton, Dickinson and Company; bioMerieux: Johnson & Johnson. Myriad Genetics, and Hologic.

Genomic Health, Inc. is the assignee of numerous patents pertaining to gene expression profiling, for example: U.S. Pat. Nos. 7,081,340; 8,808,994; 8,034,565; 8,206,919; 7,858,304; 8,741,605; 8,765,383; 7,838,224; 8,071,286; 8,148,076; 8,008,003; 8,725,426; 7,888,019; 8,906,625; 8,703,736; 7,695,913; 7,569,345; 8,067,178; 7,056,674; 8,153,379; 8,153,380; 8,153,378; 8,026,060; 8,029,995; 8,198,024; 8,273,537; 8,632,980; 7,723,033; 8,367,345; 8,911,940; 7,939,261; 7,526,637; 8,868,352; 7,930,104; 7,816,084; 7,754,431 and 7,208,470, and their foreign counterparts.

U.S. Pat. No. 9,076,104 to the Regents of the University of California titled "Systems and Methods for Identifying Drug Targets using Biological Networks" claims a method with computer executable instructions by a processor for predicting gene expression profile changes on inhibition of proteins or genes of drug targets on treating a disease, that includes constructing a genetic network using a dynamic Bayesian network based at least in part on knowledge of drug inhibiting effects on a disease, associating a set of parameters with the constructed dynamic Bayesian network, determining the values of a joint probability distribution via an automatic procedure, deriving a mean dynamic Bayesian network with averaged parameters and calculating a quantitative prediction based at least in part on the mean dynamic Bayesian network, wherein the method searches for an optimal combination of drug targets whose perturbed gene expression profiles are most similar to healthy cells.

Affymetrix has developed a number of products related to gene expression profiling. Non-limiting examples of U.S. Patents to Affymetrix include: U.S. Pat. Nos. 6,884,578; 8,029,997; 6,308,170; 6,720,149; 5,874,219; 6,171,798; and 6,391,550.

Likewise, Bio-Rad has a number of products directed to gene expression profiling. Illustrative examples of U.S. Patents to Bio-Rad include: U.S. Pat. Nos. 8,021,894; 8,451, 450; 8,518,639; 6,004,761; 6,146,897; 7,299,134; 7,160, 734; 6,675,104; 6,844,165; 6,225,047; 7,754,861 and 6,004, 761.

Koninklijke Philips N.V. (NL) has filed a number of patent applications in the general area of assessment of cellular signaling pathway activity using various mathematical models, including U.S. Ser. No. 14/233,546 (WO 2013/011479), titled "Assessment of Cellular Signaling Pathway Using Probabilistic Modeling of Target Gene Expression"; U.S. Ser. No. 14/652,805 (WO 2014/102668) titled "Assessment of Cellular Signaling Pathway Activity Using Linear Combinations of Target Gene Expressions: WO 2014/174003 titled "Medical Prognosis and Prediction of Treatment Response Using Multiple Cellular Signaling Pathway Activities; and WO 2015/101635 titled "Assessment of the PI3K Cellular Signaling Pathway Activity Using Mathematical Modeling of Target Gene Expression".

Physicians must use caution in administering a drug that modulates a target pathway to a patient with a tumor, including cancer, because that pathway may either be not tumor-affecting and/or may be playing a tumor suppressing role. Further, the role of the pathway can change over time. It is therefore important to be able to more accurately assess the functional state of the target pathway at specific points in disease progression.

It is therefore an object of the disclosure to provide a more accurate process to determine the individual characteristics of a tumor, tumorigenic propensity of the cellular signaling pathways in a cell, as well as associated methods of therapeutic treatment, kits, systems, etc.

SUMMARY

The present disclosure includes methods and apparatuses which are capable of identifying a subject at risk of experiencing a negative clinical event associated with a disease within a defined period of time (such as death, disease recurrence, disease progression or development of metastasis) by determining the activity level of a phosphatidylinositide 3-kinase (PI3K) cellular signaling pathway in combination with at least one other cellular signaling pathway selected from a Wnt signaling pathway, an estrogen-receptor (ER) signaling pathway, or a hedgehog (HH) signaling pathway, using the methods described herein. It has been discovered that determining the activity levels of these specific cellular signaling pathways using the methods described herein (for example, with specified probesets) provides for a more accurate prediction that a subject will experience the negative clinical event associated with a particular disorder, such as a tumor or cancer.

Functional cellular pathway activities can be dramatically different between, and within, particular diseases and disorders. The use of the combinatorial cellular signaling pathway activity analysis described herein using multi-pathway score (MPS) modeling can be used to directly define the specific risks of experiencing a negative clinical event associated with the disease. This more accurate risk assessment allows, for example, a clinician to develop or adjust a treatment modality to reduce or avoid the risk of experiencing the negative clinical event. For example, the use of the combination of specific pathways and methods described herein is a powerful tool in guiding clinical modalities based on the prognosis and subtyping identification in, for example, cancer, which in turn dictates the risk of experiencing a clinical event within a period of time associated with the particular disease. By identifying these subject populations before the occurrence of the clinical event, a higher accuracy of treatment options and efficacies is provided. Thus, the current disclosure provides higher accuracy in, not only the risk of experiencing a clinical event, but why the subject is likely to experience the clinical event, allowing the clinician to better address the underlying causative abnormal pathway.

The present disclosure identifies subjects at risk for developing a negative clinical event associated with a disease such as a tumor or cancer by uniquely combining the information from two steps:

a.) First determining an activity level of a PI3K cellular signaling pathway in a sample isolated from the subject, wherein the PI3K cellular signaling pathway activity is calculated by i) calculating an activity level of a PI3K transcription factor element in the sample, wherein the activity level of the PI3K transcription factor element in the sample is calculated by (1) receiving data on the expression levels of at least three PI3K selected target genes derived from the sample, wherein the PI3K transcription factor element controls transcription of the at least three PI3K target genes, (2) calculating the activity level of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor elements; and, ii) calculating the activity level of the PI3K cellular signaling pathway in the sample based on the calculated activity levels of the PI3K transcription factor element in the sample.

b.) The determination of the PI3K cellular signaling pathway activity is then analyzed in combination or in light of the activity level of at least one additional cellular signaling pathway selected from a Wnt signaling pathway, an ER signaling pathway, or a HH signaling pathway by calculating an activity level of at least one additional cellular signaling pathway in the sample, wherein the activity levels of the additional cellular signaling pathways is calculated by i) calculating an activity level of a transcription factor element from the additional cellular signaling pathway in the sample, wherein the activity level of the transcription factor element of the additional cellular signaling pathway is calculated by (1) receiving data on the expression levels of at least three target genes of the additional cellular signaling pathway derived from the sample, wherein the transcription factor element of the additional cellular signaling pathway controls transcription of the at least three target genes of the additional cellular signaling pathway, and (2) calculating the activity level of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and ii) calculating the activity level of the additional cellular signaling pathway in the sample based on the calculated activity levels of the transcription factor element of the additional cellular signaling pathway in the sample.

The term "transcription factor element" as used herein refers to an intermediate or precursor protein or protein complex of the active transcription factor, or an active transcription factor protein or protein complex which controls the specified target gene expression.

The term "target gene" as used herein, means a gene whose transcription is directly or indirectly controlled by a TGF-β transcription factor element. The "target gene" may be a "direct target gene" and/or an "indirect target gene" (as described herein).

The activity levels of the PI3K cellular signaling pathway and the at least one other cellular signaling pathway are then used to calculate a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event. The resultant MPS score is used to assign a risk of experiencing the clinical event. Using an MPS model across the cellular signaling pathways identified herein provides important and significant biological insight into the risk of certain clinical events occurring.

In one particular aspect of the present disclosure, expression levels of unique sets of target genes from the analyzed cellular signaling pathways are used to determine the activity level of the cellular signaling pathways. It has been discovered that analyzing the specified set of target genes as described herein in the disclosed pathway model provides for an advantageously accurate cellular signaling pathway activity determination, which, in turn, provides further accuracies in determining the occurrence of a particular clinical event occurring.

The determination of the activity level of the specified combinations of the cellular signaling pathways as described herein based on expression levels of unique sets of genes, and applying the calculated activity levels to a MPS model which has been calibrated against specific clinical event occurrences provides a powerful tool for identifying subjects at risk of experiencing particular clinical events, for example but not limited to, the presence or risk of developing a disease within a period of time, the recurrence of diseases, the advancement of disease, the development of metastasis of a disease, or even death and survival. Importantly, the present disclosure allows the identification of subjects at risk for such clinical events within a specific time period, for example, 3 months, 6 months, 1 year, 18 months, 2 years, 30 months, 3 years, 42 months, 4 years, 5 years, 6 years, 7 years, 8 years, 9 years, or 10 years or more. This information can be used to adjust therapeutic protocols to, for example, adjust treatment to administer a cellular signaling pathway inhibitor, wherein the identified cellular signaling pathway's activity level is associated with the identified clinical risk occurring.

The present disclosure is based on the innovation of the inventors that a suitable way of identifying effects occurring in the cellular signaling pathway described herein can be based on a measurement of the signaling output of the unique combination of particular cellular signaling pathways, which is—among others—the transcription of the unique target genes described herein by the specific transcription factor (TF) elements controlled by the cellular signaling pathway. This innovation by the inventors assumes that the TF level is at a quasi-steady state in the sample which can be detected by means of—amongst others—the expression values of the uniquely identified target genes.

In particular, unique sets of cellular signaling pathway target genes whose expression levels are analyzed in the model have been identified. For use in the model, at least one, at least two, at least three, at least four, at least, five, at least six, at least seven, at least eight, at least nine, at least ten or more target genes from each assessed cellular signaling pathway can be analyzed to develop a risk score.

As further contemplated herein, the expression levels of at least three or more for example, three, four, five, six, seven, eight, nine, ten, eleven, twelve or more PI3K target genes are analyzed, wherein the PI3K target genes are selected from ATP8A1, BCL2L11, BNIP3, BTG1, C10orf10, CAT, CBLB, CCND1, CCND2, CDKN1B, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10. In some embodiment, the at least three or more PI3K target genes are selected from AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10. In further embodiments, the expression levels of the PI3K target genes FBXO32, BCL2L11, SOD2, TNFSF10, BCL6, BTG1, CCNG2, CDKN1B, BNIP3, GADD45A, INSR, and MXI1 are determined.

In certain embodiments, at least three, four, five, six, seven, eight, nine, ten, eleven, twelve, or more Wnt target genes are selected from ADRA2C, ASCL2, AXIN2, BMP7, CCND1, CD44, COL18A1, DEFA6, DKK1, EPHB2, EPHB3, FAT1, FZD7, GLUL, HNF1A, CXCL8 (previously known as IL8). CEMIP (previously known as KIAA1199), KLF6, LECT2, LEF1, LGR5, MYC, NKD1, OAT, PPARG, REG1B, RNF43, SLC1A2, SOX9, SP5, TBX3, TCF7L2, TDGF1, and ZNRF3. In certain embodiments, the at least three or more Wnt target genes are selected from CEMIP, AXIN2, CD44, RNF43, MYC, TBX3, TDGF1, SOX9, ASCL2, CXCL8, SP5, ZNRF3, EPHB2, LGR5, EPHB3. KLF6, CCND1, DEFA6, and FZD7. In still further embodiments, the expression levels of the Wnt target genes AXIN2, CD44, LGR5, CEMIP, MYC, CXCL8, SOX9, EPHB3, RNF43, TDGF1, ZNRF3, and DEFA6 are determined.

In certain embodiments, the expression levels of at least three, four, five, six, seven, eight, nine, ten, eleven, twelve, or more ER target genes are analyzed, wherein the ER target genes are selected from AP1B1, ATP5J, COL18A1, COX7A2L, CTSD, DSCAM, EBAG9, ESR1, HSPB1. KRT19, NDUFV3, NRIP1, PGR, PISD, PRDM15, PTMA, RARA, SOD1, TFF1, TRIM25, XBP1, GREB1, IGFBP4, MYC, SGK3, WISP2, ERBB2, CA12, CDH26, and CELSR2. In certain embodiments, at least three or more ER target genes are selected from CDH26, SGK3, PGR, GREB1, CA12, XBP1, CELSR2, WISP2, DSCAM, ERBB2, CTSD, TFF1, PDZK1, IGFBP4, ESR1, SOD1, AP1B1, and NRIP1. In certain embodiments, the expression levels of the ER target genes TFF1, GREB1, PGR, SGK3, PDZK1, IGFBP4, NRIP1, CA12, XBP1, ERBB2, ESR1, and CELSR2 are determined.

The use of unique target genes of the HH pathway is provided, wherein at least three, at least four, at least five, at least six, at least seven, at least eight, at least nine, at least ten, at least eleven, at least twelve or more HH target genes are selected from GLI1, PTCH1, PTCH2, HHIP, SPP1, TSC22D1, CCND2, H19, IGFBP6, TOM1, JUP, FOXA2, MYCN, NKX2-2, NKX2-8, RAB34, MIF, GLI3, FST, BCL2, CTSL1, TCEA2, MYLK, FYN, PITRM1, CFLAR, IL1R2, S100A7, S100A9, CCND1, JAG2, FOXM1, FOXF1, and FOXL1. In certain embodiments, the at least three or more HH target genes are selected from GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1. In certain embodiments, the expression levels of the HH target genes GLI1, PTCH1, PTCH2, CCND2, IGFBP6, MYCN, FST, RAB34, GLI3, CFLAR, SI00A7, and S100A9 are determined.

In one aspect of the disclosure, provided herein is a method for identifying a subject at risk of experiencing a clinical event associated with a disease within a defined period of time performed by a computerized device having a processor comprising:
  a. calculating an activity level of a phosphatidylinositide 3-kinase (PI3K) cellular signaling pathway in a sample isolated from the subject, wherein the PI3K cellular signaling pathway activity is calculated by:
    i. calculating an activity level of the PI3K transcription factor element in the sample, wherein the activity level of the PI3K transcription factor element in the sample is calculated by:
      1. receiving data on the expression levels of at least three PI3K target genes derived from the sample, wherein the PI3K transcription factor element controls transcription of the at least three PI3K target genes,
      2. calculating the activity levels of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and,
    ii. calculating the activity level of the PI3K cellular signaling pathway in the sample based on the calculated activity level of the PI3K transcription factor element in the sample; and,
  b. calculating an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity levels of the additional cellular signaling pathways is calculated by:
    i. calculating an activity level of the transcription factor element from the additional cellular signaling pathway in the sample, wherein the activity level of the transcription factor element of the additional cellular signaling pathway is calculated by:
      1. receiving data on the expression levels of at least three target genes of the additional cellular signaling pathway derived from the sample, wherein the transcription factor element of the additional cellular signaling pathway controls transcription of the at least three target genes of the additional cellular signaling pathway.
      2. calculating the activity level of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and,
    ii. calculating the activity level of the additional cellular signaling pathway in the sample based on the calculated activity levels of the transcription factor element of the additional cellular signaling pathway in the sample; and,
  c. calculating a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event.

In one embodiment, the method further comprises assigning a risk of experiencing the clinical event based on the calculated MPS. The clinical event can be for example, but not limited to, death, disease recurrence, disease progression, development of metastasis, survival, development of cancer, for example, of a tumor or cancer, which in non-limiting embodiments can be breast, prostate, lung, glioma and colon cancer.

In one embodiment, the activity level of the PI3K cellular signaling pathway and the activity level of at least the Wnt cellular signaling pathway in the sample are used to calculate the MPS. In one embodiment, the activity level of the PI3K cellular signaling pathway and the activity level of at least the ER cellular signaling pathway in the sample are used to calculate the MPS. In one embodiment, the activity level of the PI3K cellular signaling pathway and the activity level of at least the HH cellular signaling pathway in the sample are used to calculate the MPS. In one embodiment, the activity level of the PI3K cellular signaling pathway, and the activity levels of one of the Wnt cellular signaling pathway, the ER cellular signaling pathway, or the HH cellular signaling pathway in the sample are used to calculate the MPS. In one embodiment, the activity level of the PI3K cellular signaling pathway, the activity level of the Wnt cellular signaling pathway, the activity level of the ER cellular signaling pathway, and the activity level of the HH cellular signaling pathway in the sample are used to calculate the MPS.

Methods for treating a subject are identified that provide having an increased risk of experiencing a negative clinical event. For example, if the risk of the clinical event occurring monotonically increases with an increasing activity level of the PI3K cellular signaling pathway in the sample, then the subject can be treated by administering to the subject a PI3K inhibitor. Where the risk monotonically increases with an increasing activity level of the PI3K cellular signaling pathway in the sample, the subject may be administered a PI3K inhibitor. Where the risk monotonically decreases with an increasing activity level of the ER cellular signaling pathway in the sample, the subject may be administered an estrogen hormone replacement therapeutic. Moreover, patients at high risk of experiencing a clinical event may receive chemotherapy in addition to standard of care treatment modalities such as, but not limited to, surgery, radiotherapy, (targeted) drug therapy.

The level of the cellular signaling pathway transcription factor element for the cellular signaling pathways is determined using a calibrated pathway model executed by one or more computer processors, as further described below. The calibrated pathway model compares the expression levels of the at least three target genes of the specific cellular signaling pathway in the sample with expression levels of the at least three target genes in the calibrated pathway model which define a level of a cellular signaling pathway transcription factor element. In one embodiment, the calibrated pathway model is a probabilistic model incorporating conditional probabilistic relationships that compare the expression levels of the at least three target genes in the sample with expression levels of the at least three target genes in the model which define a level of a transcription factor element of a particular cellular signaling pathway to determine the level of the transcription factor element in the sample. In one embodiment, the probabilistic model is a Bayesian network model. In an alternative embodiment, the calibrated pathway model can be a linear or pseudo-linear model. In an embodiment, the linear or pseudo-linear model is a linear or pseudo-linear combination model.

The expression levels of the innovative combination of unique set of target genes can be determined using standard methods known in the art. For example, the expression levels of the target genes can be determined by measuring the level of mRNA of the target genes, through quantitative reverse transcriptase-polymerase chain reaction techniques, using probes associated with a mRNA sequence of the target genes, using a DNA or RNA microarray, and/or by measuring the protein level of the protein encoded by the target genes. Once the expression level of the target genes is determined, the expression levels of the target genes within the sample can be utilized in the model in a raw state or, alternatively, following normalization of the expression level data. For example, expression level data can be normalized by transforming it into continuous data, z-score data, discrete data, or fuzzy data.

The calculation of the activity level of a cellular signaling pathway in the sample is performed on a computerized device having a processor capable of executing a readable program code for calculating the PI3K signaling in the sample according to the methods described above. The computerized device can include means for receiving expression level data, wherein the data is expression levels of at least three target genes of a PI3K cellular signaling pathway and at least target genes of at least one additional cellular signaling pathway as described herein and derived from the sample, a means for calculating the level of the specific transcription factor element of the cellular signaling pathways in the sample using a calibrated pathway model, wherein the calibrated pathway model compares the expression levels of the at least three target genes of the cellular signaling pathways in the sample with expression levels of the at least three target genes in the model which define a level of the cellular signaling pathway specific transcription factor elements; a means for calculating the cellular signaling in the sample based on the calculated levels the transcription factor elements in the sample, a means for calculating an MPS score using a calibrated MPS model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event; and, optionally, a means for displaying the calculated risk score.

In accordance with another disclosed aspect, further provided herein is a non-transitory storage medium capable of storing instructions that are executable by a digital processing device to perform the method according to the present disclosure as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

Methods of treating a subject are provided that identify a risk for experiencing a negative clinical even associated with a particular disease or disorder. In one embodiment, the disorder is one of an auto-immune and other immune disorders, cancer, bronchial asthma, heart disease, diabetes, hereditary hemorrhagic telangiectasia, Marfan syndrome, Vascular Ehlers-Danlos syndrome, Loeys-Dietz syndrome. Parkinson's disease, Chronic kidney disease, Multiple Sclerosis, fibrotic diseases such as liver, lung, or kidney fibrosis, Dupuytren's disease, or Alzheimer's disease. In a particular embodiment, the subject is suffering from a cancer, for example, a breast cancer, lung cancer, a colon cancer, pancreatic cancer, brain cancer, or breast cancer. In a more particular embodiment, the cancer is a breast cancer.

A kit is also provided for measuring the expression levels of at least three or more PI3K cellular signaling pathway target genes, and at least three or more target genes from at least one or more additional cellular signaling pathways. In one embodiment, the kit includes one or more components capable of measuring the expression levels of at least three PI3K signaling target genes selected from ATP8A1, BCL2L11, BNIP3, BTG1, C10orf10. CAT, CBLB, CCND1, CCND2, CDKN1B, DDB1, DYRK2, ERBB3, EREG, ESR1, EXT1, FASLG. FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10. In one embodiment, the kit comprises one or more components capable of measuring the expression levels of at least three PI3K signaling target genes selected from wherein the at least three PI3K target genes are selected from AGRP, BCL2L11, BCL6. BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10. In one embodiment, the kit comprises one or more components capable of measuring the expression levels of the PI3K target genes FBXO32, BCL2L11, SOD2, TNFSF10, BCL6, BTG1, CCNG2, CDKN1B, BNIP3, GADD45A, INSR, and MXI1.

In one embodiment, the kit comprises one or more components capable of measuring the expression levels of at least three Wnt target genes are selected from ADRA2C, ASCL2, AXIN2, BMP7, CCND1, CD44, COL18A1, DEFA6, DKK1, EPHB2, EPHB3, FAT1, FZD7, GLUL, HNF1A, CXCL8 (IL8), CEMIP (KIAA1199), KLF6, LECT2, LEF1, LGR5, MYC, NKD1, OAT, PPARG, REG1B, RNF43, SLC1A2, SOX9, SP5, TBX3, TCF7L2, TDGF1, and ZNRF3. In one embodiment, the kit comprises one or more components capable of measuring the expression levels of at least three Wnt target genes are selected from CEMIP, AXIN2, CD44, RNF43, MYC, TBX3, TDGF1, SOX9, ASCL2, CXCL8, SP5, ZNRF3, EPHB2, LGR5, EPHB3, KLF6, CCND1, DEFA6, and FZD7. In one embodiment, the kit comprises one or more components capable of measuring the expression levels of the Wnt target genes AXIN2, CD44, LGR5, CEMIP, MYC, CXCL8, SOX9, EPHB3, RNF43, TDGF1, ZNRF3, and DEFA6.

In one embodiment, the kit comprises one or more components capable of measuring the expression levels of at least three ER target genes are selected from AP1B1, ATP5J, COL18A1, COX7A2L, CTSD, DSCAM, EBAG9, ESR1, HSPB1, KRT19, NDUFV3, NRIP1, PGR, PISD, PRDM15, PTMA, RARA, SOD1, TFF1, TRIM25, XBP1, GREB1, IGFBP4, MYC, SGK3, WISP2, ERBB2, CA12, CDH26, and CELSR2. In one embodiment, the kit comprises one or more components capable of measuring the expression levels of at least three ER target genes selected from CDH26, SGK3, PGR, GREB1, CA12, XBP1, CELSR2, WISP2, DSCAM, ERBB2, CTSD, TFF1, PDZK1, IGFBP4, ESR1, SOD1, AP1B1, and NRIP1 In one embodiment, the kit comprises one or more components capable of measuring the expression levels of the ER target genes TFF1, GREB1, PGR, SGK3, PDZK1, IGFBP4, NRIP1, CA12, XBP1, ERBB2, ESR1, and CELSR2.

In one embodiment, the kit comprises one or more components capable of measuring the expression levels of at least three HH target genes selected from GLI1, PTCH1, PTCH2, HHIP, SPP1, TSC22D1, CCND2, H19, IGFBP6, TOM1, JUP, FOXA2, MYCN, NKX2-2, NKX2-8, RAB34, MIF, GLI3, FST, BCL2, CTSL1, TCEA2, MYLK, FYN, PITRM1, CFLAR, IL1R2, S100A7, S100A9, CCND1, JAG2, FOXM1, FOXF1, and FOXL1. In one embodiment, the kit comprises one or more components capable of measuring the expression levels of at least three HH target genes selected from GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1. In one embodiment, the kit comprises one or more components capable of measuring the expression levels of the HH target genes GLI1, PTCH1, PTCH2, CCND2, IGFBP6, MYCN, FST, RAB34, GLI3, CFLAR, S100A7, and S100A9.

In a specific embodiment, the kit comprises one or more components capable of measuring the expression levels of:
  a. at least three PI3K signaling target genes selected from FBXO32, BCL2L11, SOD2, TNFSF10, BCL6, BTG1, CCNG2, CDKN1B, BNIP3, GADD45A, INSR, and MXI1;
  b. at least three Wnt target genes selected from AXIN2, CD44, LGR5, CEMIP, MYC, CXCL8, SOX9, EPHB3, RNF43, TDGF1, ZNRF3, and DEFA6;
  c. at least three ER target genes selected from TFF1, GREB1, PGR, SGK3, PDZK1, IGFBP4, NRIP1, CA12, XBP1, ERBB2, ESR1, and CELSR2; and,
  d. at least three HH target genes selected from GLI1, PTCH1, PTCH2, CCND2, IGFBP6, MYCN, FST, RAB34, GLI3, CFLAR, S100A7, and S100A9.

In a particular embodiment, the kit comprises one or more components capable of measuring the expression levels of:
  a. PI3K signaling target genes FBXO32, BCL2L11, SOD2, TNFSF10, BCL6, BTG1, CCNG2, CDKN1B, BNIP3, GADD45A, INSR, and MXI1;
  b. Wnt target genes AXIN2, CD44, LGR5, CEMIP, MYC, CXCL8, SOX9, EPHB3, RNF43, TDGF1, ZNRF3, and DEFA6;
  c. ER target genes TFF1, GREB1, PGR, SGK3, PDZK1, IGFBP4, NRIP1, CA12, XBP1, ERBB2, ESR1, and CELSR2; and,
  d. HH target genes GLI1, PTCH1, PTCH2, CCND2, IGFBP6, MYCN, FST, RAB34, GLI3, CFLAR, S100A7, and S100A9.

The one or more components or means for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to a portion of an mRNA or cDNA sequence of the targeted genes as described herein. In one embodiment, the kit includes a set of primers and probes directed to a portion of an mRNA or cDNA sequence of the targeted genes as described further below, for example, a set of specific primers or probes selected from the sequences of Table 16-19. In one embodiment, the labeled probes are contained in a standardized 96-well plate. In one embodiment, the kit further includes primers or probes directed to a set of reference genes, for example, as represented in Table 20. Such reference genes can be, for example, constitutively expressed genes useful in normalizing or standardizing expression levels of the target gene expression levels described herein. In one embodiment, the kit for measuring the expression levels of cellular signaling target genes in a sample isolated from a subject comprises:
  a. a set of polymerase chain reaction primers directed to at least three PI3K cellular signaling pathway target genes from a sample isolated from a subject;
  b. a set of probes directed to the at least three PI3K cellular signaling pathway target genes, derived from the sample:
  c. a set of polymerase chain reaction primers directed to a set of at least three target genes from at least one other cellular signaling pathways, wherein the other cellular signaling pathway genes are selected from Wnt cellular signaling pathway target genes, ER cellular signaling pathway target genes, and HH cellular signaling pathway target genes; and,
  d. a set of probes directed to the at least one other cellular signaling pathway target genes, wherein the other cellular signaling pathway genes are selected from Wnt cellular signaling pathway target genes, ER cellular signaling pathway target genes, and HH cellular signaling pathway target genes.

In one embodiment, the kit further includes a non-transitory storage medium containing instructions that are executable by a digital processing device to perform a method according to the present disclosure as described herein. In one embodiment, the kit includes an identification code that provides access to a server or computer network for analyzing the activity level of the cellular signaling pathways based on the expression levels of the target genes and the methods described herein.

DETAILED DESCRIPTION OF EMBODIMENTS

Figure 1:
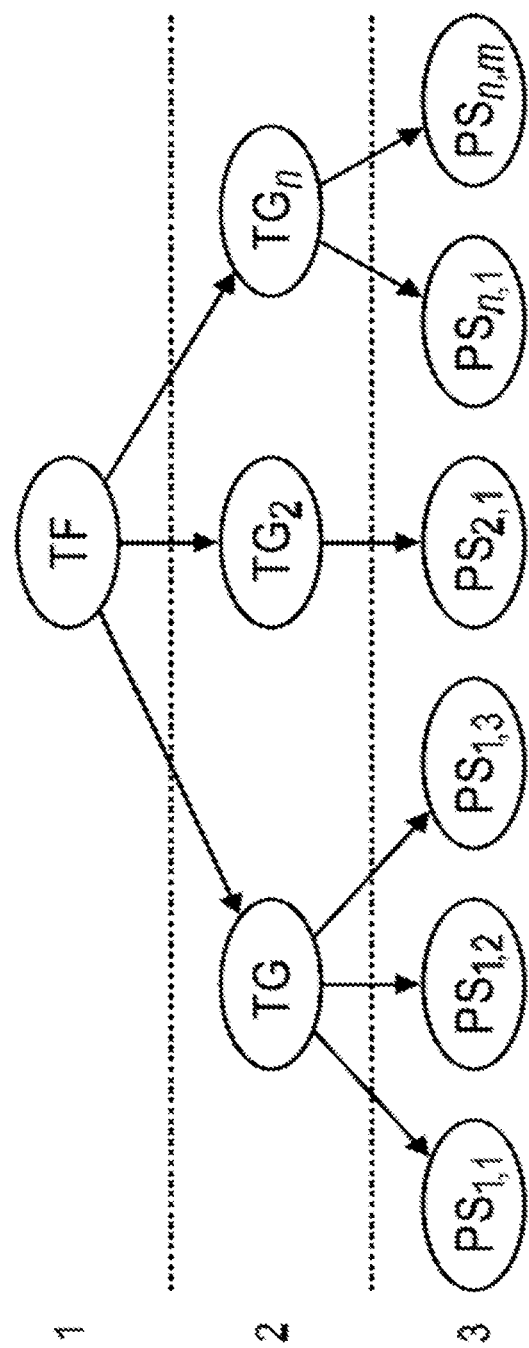
FIG. 1 shows schematically and exemplarily a mathematical model, herein, a Bayesian network model, used to model the transcriptional program of the PI3K pathway, the Wnt pathway, the ER pathway, and the HH pathway, respectively.

In accordance with a main aspect of the present disclosure, the methods and apparatuses described herein are capable of identifying a subject at risk of experiencing a negative clinical event associated with a disease within a defined period of time by determining the activity level of a phosphatidylinositide 3-kinase (PI3K) cellular signaling pathway in combination with at least one other cellular signaling pathway selected from a Wnt signaling pathway, an estrogen-receptor (ER) signaling pathway, or a hedgehog (HH) signaling pathway, using the methods described herein. It has been discovered that analyzing the activity levels of the unique combination of specific cellular signaling pathways in combination using the methods described herein provides for an advantageously accurate prediction that a subject will experience a negative clinical event associated with a particular disorder. This more accurate risk assessment allows, for example, a clinician to develop or adjust a treatment modality to reduce or avoid the risk of developing the clinical event.

The present disclosure identifies subjects at risk for developing certain clinical events associated with a particular disease in two steps:

a.) First determining an activity level of a PI3K cellular signaling pathway in a sample isolated from the subject, wherein the PI3K cellular signaling pathway activity is calculated by i) calculating an activity level a PI3K transcription factor element in the sample, wherein the activity level of the PI3K transcription factor element in the sample is calculated by (1) receiving data on the expression levels of at least three PI3K target genes derived from the sample, wherein the PI3K transcription factor element controls transcription of the at least three PI3K target genes, (2) calculating the activity level of the PI3K transcription factor elements in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and, ii) calculating the activity level of the PI3K cellular signaling pathway in the sample based on the calculated activity level of the PI3K transcription factor element in the sample.

b.) The determination of the PI3K cellular signaling pathway activity is then analyzed in combination or in light of the activity level of at least one additional cellular signaling pathway selected from a Wnt signaling pathway, an ER signaling pathway, or a HH signaling pathway by calculating an activity level of at least one additional cellular signaling pathway in the sample, wherein the activity levels of the additional cellular signaling pathways is calculated by i) calculating an activity level of transcription factor elements from the additional cellular signaling pathways in the sample, wherein the activity level of the transcription factor element of the additional cellular signaling pathway is calculated by (1) receiving data on the expression levels of at least three target genes of the additional cellular signaling pathway derived from the sample, wherein the transcription factor element of the additional cellular signaling pathway controls transcription of the at least three target genes of the additional cellular signaling pathway, and (2) calculating the activity level of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and ii) calculating the activity level of the additional cellular signaling pathway in the sample based on the calculated activity level of the transcription factor element of the additional cellular signaling pathway in the sample.

The activity levels of the PI3K cellular signaling pathway and the at least one other cellular signaling pathway are then used to calculate a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event. The resultant MPS score can be used to assign a risk of experiencing the clinical event.

In some embodiments, the increase or decrease in the activity level is monotonical. In alternative embodiments, the increase or decrease is non-monotonical. Therefore, in the specification herein where the word "monotonical is used in an embodiment, in an alternative embodiment, the increase or decrease can be non-monotonical.

Definitions

All terms used herein are intended to have their plain and ordinary meaning as normally ascribed in the art unless otherwise specifically indicated herein.

Herein, the "level" of a transcription factor (TF) element denotes the level of activity of the TF element regarding transcription of its target genes.

The term "subject", as used herein, refers to any living being. In some embodiments, the subject is an animal, for example a mammal. In certain embodiments, the subject is a human being, for example a medical subject. In a particular embodiment, the subject is a human. In one embodiment, the human is suspected of having a disorder mediated or exacerbated by an active level of one or more of the cellular signaling pathways examined by the methods provided herein, for example, a cancer. In one embodiment, the human has or is suspected of having a breast cancer.

The term "sample", as used herein, also encompasses the case where e.g. a tissue and/or cells and/or a body fluid of the subject have been taken from the subject and, e.g., have been put on a microscope slide, and where for performing the claimed method a portion of this sample is extracted, e.g., by means of Laser Capture Microdissection (LCM), or by scraping off the cells of interest from the slide, or by fluorescence-activated cell sorting techniques. In addition, the term "sample", as used herein, also encompasses the case where e.g. a tissue and/or cells and/or a body fluid of the subject have been taken from the subject and have been put on a microscope slide, and the claimed method is performed on the slide. In addition, the term "samples," as used herein, may also encompass circulating tumor cells or CTCs.

As contemplated herein, the present disclosure includes:
A) A computer implemented method for identifying a subject at risk of experiencing a clinical event associated with a disease within a defined period of time performed by a computerized device having a processor comprising:
   a. calculating an activity level of a phosphatidylinositide 3-kinase (PI3K) signaling pathway in a sample isolated from the subject, wherein the PI3K cellular signaling pathway activity is calculated by:
      i. calculating an activity level of a PI3K transcription factor element in the sample, wherein the activity level of the PI3K transcription factor element in the sample is calculated by:
         1. receiving data on the expression levels of at least three PI3K target genes derived from the sample, wherein the PI3K transcription factor element controls transcription of the at least three PI3K target genes,
         2. calculating the activity levels of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and.
      ii. calculating the activity level of the PI3K cellular signaling pathway in the sample based on the calculated activity level of the PI3K transcription factor element in the sample; and,
   b. calculating an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity levels of the additional cellular signaling pathways is calculated by:
  i. calculating an activity level of a transcription factor element from the additional cellular signaling pathway in the sample, wherein the activity level of the transcription factor element of the additional cellular signaling pathway is calculated by:
    1. receiving data on the expression levels of at least three target genes of the additional cellular signaling pathway derived from the sample, wherein the transcription factor element of the additional cellular signaling pathway controls transcription of the at least three target genes of the additional cellular signaling pathway,
    2. calculating the activity level of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor elements of the additional cellular signaling pathway; and,
  ii. calculating the activity level of the additional cellular signaling pathway in the sample based on the calculated activity level of the transcription factor element of the additional cellular signaling pathway in the sample; and,
 c. calculating a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event; and
 d. assigning a risk of experiencing the clinical event based on the calculated MPS.

In one embodiment, the activity level of the PI3K cellular signaling pathway and the activity level of at least the Wnt cellular signaling pathway in the sample are used to calculate the MPS.

In one embodiment, the activity level of the PI3K cellular signaling pathway and the activity level of at least the ER cellular signaling pathway in the sample are used to calculate the MPS. In one embodiment, the activity level of the PI3K cellular signaling pathway and the activity level of at least the HH cellular signaling pathway in the sample are used to calculate the MPS. In one embodiment, the activity level of the PI3K cellular signaling pathway, and the activity levels of one of the Wnt cellular signaling pathway, the ER cellular signaling pathway, or the HH cellular signaling pathway in the sample are used to calculate the MPS. In one embodiment, the activity level of the PI3K cellular signaling pathway, the activity level of the Wnt cellular signaling pathway, the activity level of the ER cellular signaling pathway, and the activity level of the HH cellular signaling pathway in the sample are used to calculate the MPS. In one embodiment, the clinical event is death. In one embodiment, the clinical event is disease recurrence. In one embodiment, the clinical event is disease progression. In one embodiment, the disease is cancer. In one embodiment, the cancer is breast cancer. In one embodiment, the clinical event is the development of metastatic disease. In one embodiment, the risk monotonically increases with an increasing activity level of the PI3K cellular signaling pathway in the sample. In one embodiment, the additional cellular signaling pathway is at least the Wnt cellular signaling pathway and wherein the risk monotonically increases with an increasing activity level of the Wnt cellular signaling pathway in the sample. In one embodiment, the additional cellular signaling pathway is at least the HH cellular signaling pathway, and wherein the risk monotonically increases with an increasing activity level of the HH cellular signaling in the sample. In one embodiment, the additional cellular signaling pathway is at least the ER cellular signaling pathway wherein the risk monotonically decreases with an increasing activity level of the ER cellular signaling pathway in the sample. In one embodiment, the additional cellular signaling pathway is the Wnt cellular signaling pathway, the ER cellular signaling pathway, and the HH cellular signaling pathway wherein the risk monotonically increases with an increasing activity level of the PI3K cellular signaling pathway, the Wnt cellular signaling pathway, and the HH cellular signaling pathway in the sample, and monotonically decreases with an increasing activity level of the ER cellular signaling pathway in the sample. In one embodiment, the at least three PI3K target genes are selected from ATP8A1, BCL2L11, BNIP3, BTG1, C10orf10, CAT, CBLB, CCND1, CCND2, CDKN1B, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10. In one embodiment, the at least three PI3K target genes are selected from AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10. In one embodiment, the PI3K target genes FBXO32, BCL2L11, SOD2, TNFSF10, BCL6, BTG1, CCNG2, CDKN1B, BNIP3, GADD45A, INSR, and MXI1 are determined. In one embodiment, the additional cellular signaling pathway is at least the Wnt cellular signaling pathway and wherein the at least three Wnt target genes are selected from ADRA2C, ASCL2, AXIN2, BMP7, CCND1, CD44, COL18A1, DEFA6, DKK1, EPHB2, EPHB3, FAT1, FZD7, GLUL, HNF1A, CXCL8, CEMIP, KLF6, LECT2, LEF1, LGR5, MYC, NKD1, OAT, PPARG, REG1B, RNF43, SLC1A2, SOX9, SP5, TBX3, TCF7L2, TDGF1, and ZNRF3. In one embodiment, the additional cellular signaling pathway is at least the Wnt cellular signaling pathway and wherein the at least three Wnt target genes are selected from CEMIP, AXIN2, CD44, RNF43, MYC, TBX3, TDGF1, SOX9, ASCL2, CXCL8, SP5, ZNRF3, EPHB2, LGR5, EPHB3, KLF6, CCND1, DEFA6, and FZD7. In one embodiment, the additional cellular signaling pathway is at least the Wnt cellular signaling pathway and wherein the expression levels of the Wnt target genes AXIN2, CD44, LGR5, CEMIP, MYC, CXCL8, SOX9, EPHB3, RNF43, TDGF1, ZNRF3, and DEFA6 are determined. In one embodiment, the additional cellular signaling pathway is at least the ER cellular signaling pathway and wherein the at least three ER target genes are selected from AP1B1, ATP5J, COL18A1, COX7A2L, CTSD, DSCAM. EBAG9, ESR1, HSPB1, KRT19. NDUFV3, NRIP1, PGR, PISD, PRDM15, PTMA, RARA, SOD1, TFF1, TRIM25, XBP1, GREB1, IGFBP4, MYC, SGK3, WISP2, ERBB2, CA12, CDH26, and CELSR2. In one embodiment, the additional cellular signaling pathway is at least the ER cellular signaling pathway and wherein the at least three ER target genes are selected from CDH26, SGK3. PGR. GREB1. CA12, XBP1, CELSR2, WISP2, DSCAM, ERBB2, CTSD, TFF1, PDZK1, IGFBP4, ESR1, SOD1, AP1B1, and NRIP1. In one embodiment, the additional cellular signaling pathway is at least the ER cellular signaling pathway and wherein the expression levels of the ER target genes TFF1, GREB1, PGR, SGK3, PDZK1, IGFBP4, NRIP1, CA12, XBP1, ERBB2, ESR1, and CELSR2 are determined. In one embodiment, the additional cellular signaling pathway is at least the HH cellular signaling pathway and wherein the at least three HH target genes are selected from GLI1, PTCH1, PTCH2, HHIP, SPP1, TSC22D1, CCND2, H19, IGFBP6, TOM1, JUP, FOXA2, MYCN, NKX2-2, NKX2-8, RAB34, MIF, GLI3, FST, BCL2, CTSL1, TCEA2, MYLK, FYN, PITRM1, CFLAR, IL1R2, S100A7, S100A9, CCND1, JAG2, FOXM1, FOXF1, and FOXL1. In one embodiment, the additional cellular signaling pathway is at least the HH cellular signaling pathway and wherein the at least three HH target genes are selected from GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1.

In one embodiment, the additional cellular signaling pathway is at least the HH cellular signaling pathway and wherein the expression levels of the HH target genes GLI1, PTCH1, PTCH2, CCND2, IGFBP6, MYCN, FST, RAB34, GLI3, CFLAR, S100A7, and S100A9 are determined. In one embodiment, the additional cellular signaling pathway is at least the Wnt cellular signaling pathway and wherein the MPS is calculated by the following equation:

$$MPS = w_p \cdot P_p + w_w \cdot P_w$$

wherein $P_p$, and $P_w$, denote the calculated activity of the PI3K cellular signaling pathway and the Wnt cellular signaling pathway respectively, and wherein $w_p$ and $w_w$ are weighting coefficients representing a correlation between the activity of the PI3K cellular signaling pathway and the Wnt cellular signaling pathway respectively to the risk of the clinical event occurring. In one embodiment, the additional cellular signaling pathway is at least the ER cellular signaling pathway and wherein the MPS is calculated by the following equation:

$$MPS = w_p \cdot P_p + w_e \cdot P_e$$

wherein $P_p$ and $P_e$ denote the calculated activity of the PI3K cellular signaling pathway and the ER cellular signaling pathway respectively, and wherein $w_p$ and $w_e$ are weighting coefficients representing a correlation between the activity of the PI3K cellular signaling pathway and the ER cellular signaling pathway respectively to the risk of the clinical event occurring. In one embodiment, the additional cellular signaling pathway is at least the HH cellular signaling pathway and wherein the MPS is calculated by the following equation:

$$MPS = w_p \cdot P_p + w_h \cdot P_h$$

wherein $P_p$ and $P_h$ denote the calculated activity of the PI3K cellular signaling pathway and the HH cellular signaling pathway respectively, and wherein $w_p$ and $w_h$ are weighting coefficients representing a correlation between the activity of the PI3K cellular signaling pathway and the HH cellular signaling pathway respectively to the risk of a clinical event occurring. In one embodiment, the additional cellular signaling pathway is the Wnt cellular signaling pathway, the ER cellular signaling pathway, and the HH cellular signaling pathway, and wherein the MPS is calculated by the following equation:

$$MPS = w_p \cdot P_p + w_w \cdot P_w + w_e \cdot P_e + w_h \cdot P_h$$

wherein $P_p$, $P_w$, $P_e$, and $P_h$ denote the calculated activity of the the PI3K cellular signaling pathway, the Wnt cellular signaling pathway, the ER cellular signaling pathway, and the HH cellular signaling pathway respectively, and wherein $w_p$, $w_w$, $w_e$ and $w_h$ are weighting coefficients representing a correlation between the activity of the the PI3K cellular signaling pathway, the Wnt cellular signaling pathway, the ER cellular signaling pathway, and the HH cellular signaling pathway respectively to the risk of the clinical event occurring. In one embodiment, the weighting coefficients $w_p$ and $w_w$ are calculated using a Cox's proportional hazard model, wherein the Cox's proportional hazard model is fitted to a training set of samples with calculated activities $P_p$ and $P_w$ and survival data. In one embodiment, the weighting coefficients $w_p$ and $w_e$ are calculated using a Cox's proportional hazard model, wherein the Cox's proportional hazard model is fitted to a training set of samples with calculated activities $P_p$ and $P_e$ and survival data. In one embodiment, the weighting coefficients $w_p$ and $w_h$ are calculated using a Cox's proportional hazard model, wherein the Cox's proportional hazard model is fitted to a training set of samples with calculated activities $P_p$ and $P_h$ and survival data. In one embodiment, the weighting coefficients $w_p$, $w_p$, $w_e$, $w_e$ and $w_h$ are calculated using a Cox's proportional hazard model, wherein the Cox's proportional hazard model is fitted to a training set of samples with calculated activities $P_p$, $P_w$, $P_e$, and $P_h$ and survival data. In one embodiment, the risk score is the MPS. In one embodiment, the risk score is used to prescribe a course of treatment to decrease the risk of the clinical event occurring.

B) A computer program product for identifying a subject at risk of experiencing a clinical event associated with a disease within a defined period of time comprising:

a. a non-transitory computer readable storage medium having computer readable program code embodied therewith, the computer readable program code executable by at least one processor to:

i. calculate activity level of a PI3K cellular signaling pathway in a sample isolated from the subject, wherein the PI3K cellular signaling pathway activity is calculated by:

1. calculating an activity level of a PI3K transcription factor element in the sample, wherein the activity level of the PI3K transcription factor element in the sample is calculated by:

a. receiving data on the expression levels of at least three PI3K target genes derived from the sample, wherein the PI3K transcription factor element controls transcription of the at least three PI3K target genes, b. calculating the activity levels of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and, 2. calculating the activity level of the PI3K cellular signaling pathway in the sample based on the calculated activity level of the PI3K transcription factor element in the sample; and, ii. calculate an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity levels of the additional cellular signaling pathways is calculated by:

a. calculating an activity level of a transcription factor element from the additional cellular signaling pathway in the sample, wherein the activity level of the transcription factor element of the additional cellular signaling pathway is calculated by:

i. receiving data on the expression levels of at least three target genes of the additional cellular signaling pathway derived from the sample, wherein the transcription factor element of the additional cellular signaling pathway controls transcription of the at least three target genes of the additional cellular signaling pathway, ii. calculating the activity levels of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and, b. calculating the activity level of the additional cellular signaling pathway in the sample based on the calculated activity level of the transcription factor element of the additional cellular signaling pathway in the sample; and, iii. calculate a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event.

In one embodiment, the computer readable program code is executable by at least one processor to assign a risk of experiencing the clinical event based on the calculated MPS. In one embodiment, the computer readable program code is executable by at least one processor to display the risk of experiencing the clinical event.

C) A method of treating a subject suffering from a disease, wherein the disease places the subject at risk of experiencing a clinical event in a defined period of time, comprising:

a. receiving information regarding the risk that the subject will experience a clinical event within a defined period of time associated with the disease, wherein the risk is determined by:

i. calculating an activity level of a PI3K cellular signaling pathway in a sample isolated from the subject, wherein the PI3K cellular signaling pathway activity is calculated by:

1. calculating an activity level of a PI3K transcription factor element in the sample, wherein the activity level of the PI3K transcription factor element in the sample is calculated by:

a. receiving data on the expression levels of at least three PI3K target genes derived from the sample, wherein the PI3K transcription factor element controls transcription of the at least three PI3K target genes, b. calculating the activity levels of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and, 2. calculating the activity level of the PI3K cellular signaling pathway in the sample based on the calculated activity level of the PI3K transcription factor element in the sample; and, ii. calculating an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity levels of the additional cellular signaling pathways is calculated by:

1. calculating an activity level of a transcription factor element from the additional cellular signaling pathway in the sample, wherein the activity level of the transcription factor element of the additional cellular signaling pathway is calculated by:

a. receiving data on the expression levels of at least three target genes of the additional cellular signaling pathway derived from the sample, wherein the transcription factor element of the additional cellular signaling pathway controls transcription of the at least three target genes of the additional cellular signaling pathway, b. calculating the activity level of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and, 2. calculating the activity level of the additional cellular signaling pathway in the sample based on the calculated activity level of the transcription factor element of the additional cellular signaling pathway in the sample; and, iii. calculating a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event; and iv. assigning a risk of experiencing the clinical event based on the calculated MPS; and, b. administering to the subject a treatment based on the risk that the subject will experience the clinical event within the certain period of time.

In one embodiment, the activity level of the PI3K cellular signaling pathway and the activity level of at least the Wnt cellular signaling pathway in the sample are used to calculate the MPS. In one embodiment, the activity level of the PI3K cellular signaling pathway and the activity level of at least the ER cellular signaling pathway in the sample are used to calculate the MPS. In one embodiment, the activity level of the PI3K cellular signaling pathway and the activity level of at least the HH cellular signaling pathway in the sample are used to calculate the MPS. In one embodiment, the activity level of the PI3K cellular signaling pathway, and the activity levels of one of the Wnt cellular signaling pathway, the ER cellular signaling pathway, or the HH cellular signaling pathway in the sample are used to calculate the MPS. In one embodiment, the activity level of the PI3K cellular signaling pathway, the activity level of the Wnt cellular signaling pathway, the activity level of the ER cellular signaling pathway, and the activity level of the HH cellular signaling pathway in the sample are used to calculate the MPS. In one embodiment, the clinical event is death. In one embodiment, the clinical event is disease recurrence. In one embodiment, the clinical event is disease progression. In one embodiment, the disease is cancer. In one embodiment, the cancer is breast cancer. In one embodiment, the clinical event is the development of metastatic disease. In one embodiment, the risk monotonically increases with an increasing activity level of the PI3K cellular signaling pathway in the sample. In one embodiment, the risk is increased due to an activity level of the PI3K cellular signaling pathway in the sample, administering to the subject a PI3K cellular signaling pathway inhibitor. In one embodiment, the additional cellular signaling pathway is at least the Wnt cellular signaling pathway and wherein the risk monotonically increases with an increasing activity level of the Wnt cellular signaling pathway in the sample. In one embodiment, the risk is increased due to an activity level of the Wnt cellular signaling pathway in the sample, administering to the subject a Wnt cellular signaling pathway inhibitor. In on embodiment, the additional cellular signaling pathway is at least the ER cellular signaling pathway and wherein the risk monotonically decreases with an increasing activity level of the ER cellular signaling pathway in the sample. In one embodiment, if the risk is decreased due to an activity level of the ER cellular signaling pathway in the sample, administering to the subject hormone therapy. In one embodiment, the additional cellular signaling pathway is at least the HH cellular signaling pathway and wherein the risk monotonically increases with an increasing activity level of the HH cellular signaling pathway in the sample. In one embodiment, if the risk is increased due to an activity level of the HH cellular signaling pathway in the sample, administering to the subject a HH cellular signaling pathway inhibitor. In one embodiment, the additional cellular signaling pathway is the Wnt cellular signaling pathway, the ER cellular signaling pathway, and the HH cellular signaling pathway wherein the risk monotonically increases with an increasing activity level of the PI3K cellular signaling pathway, the Wnt cellular signaling pathway, and the HH cellular signaling pathway in the sample, and monotonically decreases with an increasing activity level of the ER cellular signaling pathway in the sample. In one embodiment, the at least three PI3K target genes are selected from ATP8A1, BCL2L11, BNIP3, BTG1, C10orf10, CAT, CBLB, CCND1, CCND2, CDKN1B, DDB1, DYRK2, ERBB3, EREG, ESR1, EXT1, FASLG. FGFR2. GADD45A, IGF1R. IGFBP1. IGFBP3, INSR, LGMN, MXI1, PPM1D, SEMA3C, SEPP1, SESN1, SLC5A3, SMAD4, SOD2, TLE4, and TNFSF10. In one embodiment, the at least three PI3K target genes are selected from AGRP, BCL2L11, BCL6, BNIP3, BTG1, CAT, CAV1, CCND1, CCND2, CCNG2, CDKN1A, CDKN1B, ESR1, FASLG. FBXO32, GADD45A, INSR, MXI1, NOS3, PCK1, POMC, PPARGC1A, PRDX3, RBL2, SOD2, and TNFSF10. In one embodiment, the expression levels of the PI3K target genes FBXO32, BCL2L11, SOD2, TNFSF10, BCL6, BTG1, CCNG2, CDKN1B, BNIP3, GADD45A, INSR, and MXI1 are determined. In one embodiment, the additional cellular signaling pathway is at least the Wnt cellular signaling pathway and wherein the at least three Wnt target genes are selected from ADRA2C, ASCL2, AXIN2, BMP7, CCND1, CD44, COL18A1, DEFA6, DKK1, EPHB2, EPHB3, FAT1, FZD7, GLUL, HNF1A, CXCL8, CEMIP, KLF6. LECT2, LEF1, LGR5. MYC, NKD1, OAT, PPARG, REG1B, RNF43, SLC1A2, SOX9, SP5, TBX3, TCF7L2, TDGF1, and ZNRF3. In one embodiment, the additional cellular signaling pathway is at least the Wnt cellular signaling pathway and wherein the at least three Wnt target genes are selected from CEMIP, AXIN2, CD44, RNF43, MYC, TBX3, TDGF1, SOX9, ASCL2, CXCL8, SP5, ZNRF3, EPHB2, LGR5, EPHB3, KLF6, CCND1, DEFA6, and FZD7. In one embodiment, the additional cellular signaling pathway is at least the Wnt cellular signaling pathway and wherein the expression levels of the Wnt target genes AXIN2, CD44, LGR5, CEMIP, MYC, CXCL8, SOX9, EPHB3, RNF43, TDGF1, ZNRF3, and DEFA6 are determined. In one embodiment, the additional cellular signaling pathway is at least the ER cellular signaling pathway and wherein the at least three ER target genes are selected from AP1B1, ATP5J, COL18A1, COX7A2L, CTSD, DSCAM, EBAG9, ESR1, HSPB1, KRT19, NDUFV3, NRIP1, PGR, PISD, PRDM15, PTMA, RARA, SOD1, TFF1, TRIM25, XBP1, GREB1, IGFBP4, MYC, SGK3, WISP2. ERBB2, CA12, CDH26, and CELSR2. In one embodiment, the additional cellular signaling pathway is at least the ER cellular signaling pathway and wherein the at least three ER target genes are selected from CDH26, SGK3, PGR, GREB1, CA12, XBP1, CELSR2, WISP2, DSCAM, ERBB2, CTSD, TFF1, PDZK1, IGFBP4, ESR1, SOD1, AP1B1, and NRIP1. In one embodiment, the additional cellular signaling pathway is at least the ER cellular signaling pathway and wherein the expression levels of the ER target genes TFF1, GREB1, PGR, SGK3, PDZK1, IGFBP4, NRIP1, CA12, XBP1, ERBB2, ESR1, and CELSR2 are determined. In one embodiment, the additional cellular signaling pathway is at least the HH cellular signaling pathway and wherein the at least three HH target genes are selected from GLI1, PTCH1, PTCH2, HHIP, SPP1, TSC22D1, CCND2, H19, IGFBP6, TOM1, JUP, FOXA2, MYCN, NKX2-2, NKX2-8. RAB34, MIF, GLI3. FST, BCL2, CTSL1, TCEA2, MYLK, FYN, PITRM1, CFLAR, IL1R2, S100A7, S100A9, CCND1, JAG2, FOXM1, FOXF1, and FOXL1. In one embodiment, the additional cellular signaling pathway is at least the HH cellular signaling pathway and wherein the at least three HH target genes are selected from GLI1, PTCH1, PTCH2, IGFBP6, SPP1, CCND2, FST. FOXL1, CFLAR, TSC22D1, RAB34, S100A9, S100A7, MYCN, FOXM1, GLI3, TCEA2, FYN, and CTSL1. In one embodiment, the additional cellular signaling pathway is at least the HH cellular signaling pathway and wherein the expression levels of the HH target genes GLI1, PTCH1, PTCH2, CCND2, IGFBP6, MYCN, FST, RAB34, GLI3, CFLAR, S100A7, and S100A9 are determined. In one embodiment, the additional cellular signaling pathway is at least the Wnt cellular signaling pathway and wherein the MPS is calculated by the following equation:

$$MPS = w_p \cdot P_p + w_w \cdot P_w$$

wherein $P_p$ and $P_w$ denote the calculated activity of the PI3K cellular signaling pathway and the Wnt cellular signaling pathway respectively, and wherein $w_p$ and $w_w$ are weighting coefficients representing a correlation between the activity of the PI3K cellular signaling pathway and the Wnt cellular signaling pathway respectively to the risk of the clinical event occurring. In one embodiment, the additional cellular signaling pathway is at least the ER cellular signaling pathway and wherein the MPS is calculated by the following equation:

$$MPS = w_p \cdot P_p + w_e \cdot P_e$$

wherein $P_p$ and $P_e$ denote the calculated activity of the PI3K cellular signaling pathway and the ER cellular signaling pathway respectively, and wherein $w_p$ and $w_e$ are weighting coefficients representing a correlation between the activity of the PI3K cellular signaling pathway and the ER cellular signaling pathway respectively to the risk of the clinical event occurring. In one embodiment, the additional cellular signaling pathway is at least the HH cellular signaling pathway and wherein the MPS is calculated by the following equation:

$$MPS = w_p \cdot P_p + w_h \cdot P_h$$

wherein $P_p$ and $P_h$ denote the calculated activity of the PI3K cellular signaling pathway and the HH cellular signaling pathway respectively, and wherein $w_p$ and $w_h$ are weighting coefficients representing a correlation between the activity of the PI3K cellular signaling pathway and the HH cellular signaling pathway respectively to the risk of a clinical event occurring. In one embodiment, the additional cellular signaling pathway is Wnt cellular signaling pathway, the ER cellular signaling pathway, and the HH cellular signaling pathway, and wherein the MPS is calculated by the following equation:

$$MPS = w_p \cdot P_p + w_w \cdot P_w + w_e \cdot P_e + w_h \cdot P_h$$

wherein $P_p$, $P_w$, $P_e$, and $P_h$ denote the calculated activity of the PI3K cellular signaling pathway, the Wnt cellular signaling pathway, the ER cellular signaling pathway, and the HH cellular signaling pathway respectively, and wherein $w_p$, $w_w$, $w_e$ and $w_h$ are weighting coefficients representing a correlation between the activity of the PI3K cellular signaling pathway, the Wnt cellular signaling pathway, the ER cellular signaling pathway, and the HH cellular signaling pathway respectively to the risk of the clinical event occurring. In one embodiment, the weighting coefficients $w_p$ and $w_w$ are calculated using a Cox's proportional hazard model, wherein the Cox's proportional hazard model is fitted to a training set of samples with calculated activities $P_p$ and $P_w$ and survival data. In one embodiment, the weighting coefficients $w_p$ and $w_e$ are calculated using a Cox's proportional hazard model, wherein the Cox's proportional hazard model is fitted to a training set of samples with calculated activities $P_p$ and $P_e$ and survival data. In one embodiment, the weighting coefficients $w_p$ and $w_h$ are calculated using a Cox's proportional hazard model, wherein the Cox's proportional hazard model is fitted to a training set of samples with calculated activities $P_p$ and $P_h$ and survival data In one embodiment, the weighting coefficients $w_p$, $w_w$, $w_e$ and $w_h$ are calculated using a Cox's proportional hazard model, wherein the Cox's proportional hazard model is fitted to a training set of samples with calculated activities $P_p$, $P_w$, $P_e$, and $P_h$ and survival data. In one embodiment, the risk score is the MPS.

D) A kit for identifying a subject at risk of experiencing a clinical event associated with a disease within a defined period of time comprising:
  a one or more components capable of measuring the expression levels of at least three PI3K cellular signaling pathway target genes; and,
  b. one or more components capable of measuring the expression levels of a set of at least one other cellular signaling pathway target genes, wherein the other cellular signaling pathway target genes are selected from Wnt cellular signaling pathway target genes. ER cellular signaling pathway target genes, and HH cellular signaling pathway target genes; and,
  c. a non-transitory computer readable storage medium having computer readable program code embodied therewith, the computer readable program code executable by at least one processor to:
    i. calculate activity level of a PI3K cellular signaling pathway in a sample isolated from the subject, wherein the PI3K cellular signaling pathway activity is calculated by:
      1. calculating an activity level of a PI3K transcription factor elements in the sample, wherein the activity level of the PI3K transcription factor element in the sample is calculated by:
        a. receiving data on the expression levels of at least three PI3K target genes derived from the sample, wherein the PI3K transcription factor element controls transcription of the at least three PI3K target genes,
        b. calculating the activity levels of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and,
      2. calculating the activity level of the PI3K cellular signaling pathway in the sample based on the calculated activity level of the PI3K transcription factor element in the sample; and,
    ii. calculate an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity levels of the additional cellular signaling pathways is calculated by:
      1. calculating an activity level of a transcription factor element from the additional cellular signaling pathway in the sample, wherein the activity level of the transcription factor element of the additional cellular signaling pathway is calculated by:

a. receiving data on the expression levels of at least three target genes of the additional cellular signaling pathway derived from the sample, wherein the transcription factor element of the additional cellular signaling pathway controls transcription of the at least three target genes of the additional cellular signaling pathway, b. calculating the activity levels of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and, 2. calculating the activity level of the additional cellular signaling pathway in the sample based on the calculated activity level of the transcription factor element of the additional cellular signaling pathway in the sample; and, iii. calculate a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event.

In one embodiment, the kit comprises one or more components capable of measuring the expression levels of at least three PI3K signaling target genes selected from ATP8A1, BCL2L11, BNIP3, BTG1, C10orf10, CAT, CBLB, CCND1, CCND2, CDKN1B, DDB1, DYRK2, ERBB3, EREG, ESR1, EXT1, FASLG, FGFR2, GADD45A, IGF1R, IGFBP1, IGFBP3. INSR, LGMN, MXI1, PPM1D. SEMA3C, SEPP1, SESN1, SLC5A3, SMAD4, SOD2, TLE4, and TNFSF10. In one embodiment, the kit comprises one or more components capable of measuring the expression levels of at least three PI3K signaling target genes selected from wherein the at least three PI3K target genes are selected from AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10. In one embodiment, the kit comprises one or more components capable of measuring the expression levels of the PI3K target genes FBXO32, BCL2L11, SOD2, TNFSF10, BCL6, BTG1, CCNG2, CDKN1B, BNIP3, GADD45A, INSR, and MXI1. In one embodiment, the kit comprises one or more components capable of measuring the expression levels of at least three Wnt target genes are selected from ADRA2C, ASCL2, AXIN2, BMP7, CCND1, CD44, COL18A1, DEFA6, DKK1, EPHB2, EPHB3, FAT1, FZD7, GLUL, HNF1A, CXCL8, CEMIP, KLF6, LECT2, LEF1, LGR5, MYC, NKD1, OAT, PPARG, REG1B, RNF43, SLC1A2, SOX9, SP5, TBX3, TCF7L2, TDGF1, and ZNRF3. In one embodiment, the kit comprises one or more components capable of measuring the expression levels of at least three Wnt target genes are selected from CEMIP, AXIN2, CD44, RNF43, MYC, TBX3, TDGF1, SOX9, ASCL2, CXCL8, SP5, ZNRF3, EPHB2, LGR5, EPHB3, KLF6, CCND1, DEFA6, and FZD7. In one embodiment, the kit comprises one or more components capable of measuring the expression levels of the Wnt target genes AXIN2, CD44, LGR5, CEMIP, MYC, CXCL8, SOX9, EPHB3, RNF43, TDGF1, ZNRF3, and DEFA6. In one embodiment, the kit comprises one or more components capable of measuring the expression levels of at least three ER target genes are selected from AP1B1, ATP5J, COL18A1, COX7A2L, CTSD, DSCAM, EBAG9, ESR1, HSPB1, KRT19, NDUFV3, NR1P1, PGR, PISD, PRDM15, PTMA, RARA, SOD1, TFF1. TRIM25, XBP1, GREB1, IGFBP4. MYC, SGK3, WISP2, ERBB2, CA12, CDH26, and CELSR2. In one embodiment, the kit comprises one or more components capable of measuring the expression levels of at least three ER target genes are selected from CDH26, SGK3, PGR, GREB1, CA12, XBP1, CELSR2, WISP2, DSCAM, ERBB2, CTSD, TFF1, PDZK1, IGFBP4, ESR1, SOD1, AP1B1, and NRIP1. In one embodiment, the kit comprises one or more components capable of measuring the expression levels of the ER target genes TFF1, GREB1, PGR, SGK3, PDZK1, IGFBP4, NRIP1, CA12, XBP1, ERBB2, ESR1, and CELSR2. In one embodiment, the kit comprises one or more components capable of measuring the expression levels of at least three HH target genes are selected from GLI1, PTCH1, PTCH2, HHIP, SPP1, TSC22D1, CCND2, H19, IGFBP6, TOM1, JUP, FOXA2, MYCN, NKX2-2, NKX2-8, RAB34, MIF, GLI3, FST, BCL2, CTSL1, TCEA2, MYLK, FYN, PITRM1, CFLAR, IL1R2, S100A7, S100A9, CCND1, JAG2, FOXM1, FOXF1, and FOXL1. In one embodiment, the kit comprises one or more components capable of measuring the expression levels of at least three HH target genes are selected from GLI1, PTCH1, PTCH2, IGFBP6. SPP1, CCND2, FST, FOXL1, CFLAR, TSC22D1, RAB34, S100A9, S100A7, MYCN, FOXM1, GLI3, TCEA2, FYN, and CTSL1. In one embodiment, the kit comprises one or more components capable of measuring the expression levels of the HH target genes GLI1, PTCH1, PTCH2, CCND2, IGFBP6, MYCN, FST, RAB34, GLI3, CFLAR, S100A7, and S100A9 In one embodiment, the kit comprises one or more components capable of measuring the expression levels of:

a. at least three PI3K signaling target genes selected from FBXO32, BCL2L11. SOD2, TNFSF10, BCL6, BTG1, CCNG2, CDKN1B, BNIP3, GADD45A, INSR, and MXI1;

b. at least three Wnt target genes selected from AXIN2, CD44, LGR5, CEMIP, MYC, CXCL8, SOX9, EPHB3, RNF43, TDGF1, ZNRF3, and DEFA6;

c. at least three ER target genes selected from TFF1, GREB1, PGR. SGK3, PDZK1, IGFBP4, NRIP1, CA12, XBP1, ERBB2, ESR1, and CELSR2; and, d. at least three HH target genes selected from GLI1, PTCH1, PTCH2, CCND2, IGFBP6, MYCN, FST, RAB34, GLI3, CFLAR, S100A7, and S100A9.

In one embodiment, the kit comprises one or more components capable of measuring the expression levels of:

a. PI3K signaling target genes FBXO32, BCL2L11, SOD2, TNFSF10, BCL6, BTG1, CCNG2, CDKN1B, BNIP3, GADD45A, INSR, and MXI1;

b. Wnt target genes AXIN2, CD44, LGR5, CEMIP, MYC, CXCL8, SOX9, EPHB3, RNF43, TDGF1, ZNRF3, and DEFA6;

c. ER target genes TFF1, GREB1, PGR, SGK3, PDZK1, IGFBP4, NRIP1, CA12, XBP1, ERBB2, ESR1, and CELSR2; and, d. HH target genes GLI1, PTCH1, PTCH2, CCND2, IGFBP6, MYCN, FST, RAB34, GL13, CFLAR, S100A7, and S100A9.

B) A kit for measuring the expression levels of cellular signaling target genes in a sample isolated from a subject comprising:
  a. a set of polymerase chain reaction primers directed to at least three PI3K cellular signaling pathway target genes from a sample isolated from a subject;
  b. a set of probes directed to the at least three PI3K cellular signaling pathway target genes;
  c. a set of polymerase chain reaction primers directed to a set of at least three target genes from at least one other cellular signaling pathways, wherein the other cellular signaling pathway genes are selected from Wnt cellular signaling pathway target genes, ER cellular signaling pathway target genes, and HH cellular signaling pathway target genes; and,
  d. a set of probes directed to the at least one other cellular signaling pathway target genes.

In one embodiment, the kit comprises primers and probes directed to at least three PI3K signaling target genes selected from ATP8A1, BCL2L11, BNIP3, BTG1, C10orf10, CAT, CBLB, CCND1, CCND2, CDKN1B, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10. In one embodiment, the kit comprises primers and probes directed to at least three PI3K signaling target genes selected from wherein the at least three PI3K target genes are selected from AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10. In one embodiment, the kit comprises primers and probes directed to the PI3K target genes FBXO32, BCL2L11, SOD2, TNFSF10, BCL6, BTG1, CCNG2, CDKN1B, BNIP3, GADD45A, INSR, and MXI1. In one embodiment, the kit comprises primers and probes directed to at least three Wnt target genes are selected from ADRA2C, ASCL2, AXIN2, BMP7, CCND1, CD44, COL18A1, DEFA6, DKK1, EPHB2, EPHB3, FAT1, FZD7, GLUL, HNF1A, CXCL8, CEMIP, KLF6, LECT2, LEF1, LGR5, MYC, NKD1, OAT, PPARG, REG1B, RNF43, SLC1A2, SOX9, SP5, TBX3, TCF7L2, TDGF1, and ZNRF3. In one embodiment, the kit comprises primers and probes directed to at least three Wnt target genes are selected from CEMIP, AXIN2, CD44, RNF43, MYC, TBX3, TDGF1, SOX9, ASCL2, CXCL8, SP5, ZNRF3, EPHB2, LGR5, EPHB3, KLF6, CCND1, DEFA6, and FZD. In one embodiment, the kit comprises primers and probes directed to the Wnt target genes AXIN2, CD44, LGR5, CEMIP, MYC, CXCL8, SOX9, EPHB3, RNF43, TDGF1. ZNRF3, and DEFA6. In one embodiment, the kit comprises primers and probes directed to at least three ER target genes are selected from AP1B1, ATP5J, COL18A1, COX7A2L, CTSD, DSCAM, EBAG9, ESR1, HSPB1, KRT19, NDUFV3, NRIP1, PGR. PISD, PRDM15, PTMA, RARA, SOD1, TFF1, TRIM25, XBP1, GREB1, IGFBP4, MYC, SGK3, WISP2, ERBB2, CA12, CDH26, and CELSR2. In one embodiment, the kit comprises primers and probes directed to at least three ER target genes are selected from CDH26, SGK3, PGR, GREB1, CA12. XBP1, CELSR2, WISP2, DSCAM, ERBB2, CTSD. TFF1, PDZK1, IGFBP4, ESR1, SOD1, AP1B1, and NRIP1. In one embodiment, the kit comprises primers and probes directed to the ER target genes TFF1, GREB1, PGR, SGK3, PDZK1, IGFBP4, NRIP1, CA12, XBP1, ERBB2, ESR1, and CELSR2. In one embodiment, the kit comprises primers and probes directed to at least three HH target genes are selected from GLI1, PTCH1, PTCH2, HHIP, SPP1, TSC22D1, CCND2, H19, IGFBP6, TOM1, JUP, FOXA2, MYCN, NKX2-2, NKX2-8, RAB34, MIF, GLI3, FST, BCL2, CTSL1, TCEA2, MYLK, FYN, PITRM1, CFLAR, IL1R2, S100A7, S100A9, CCND1, JAG2, FOXM1, FOXF1, and FOXL1. In one embodiment, the kit comprises primers and probes directed to at least three HH target genes are selected from GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1. In one embodiment, the kit comprises primers and probes directed to the HH target genes GLI1, PTCH1, PTCH2, CCND2, IGFBP6, MYCN, FST, RAB34, GLI3, CFLAR, S100A7, and S100A9. In one embodiment, the kit comprises primers and probes directed to:
  a. at least three PI3K signaling target genes selected from FBXO32, BCL2L11, SOD2, TNFSF10, BCL6, BTG1, CCNG2, CDKN1B, BNIP3, GADD45A, INSR, and MXI1;
  b. at least three Wnt target genes selected from AXIN2, CD44, LGR5, CEMIP, MYC, CXCL8, SOX9, EPHB3, RNF43, TDGF1, ZNRF3, and DEFA6;
  c. at least three ER target genes selected from TFF1, GREB1, PGR, SGK3, PDZK1, IGFBP4. NRIP1, CA12, XBP1, ERBB2, ESR1, and CELSR2;
  d. at least three HH target genes selected from GLI1, PTCH1, PTCH2, CCND2, IGFBP6, MYCN, FST, RAB34, GL13, CFLAR, S100A7, and S100A9.

In one embodiment the kit comprises primers and probes directed to:
  a. PI3K signaling target genes FBXO32, BCL2L11, SOD2, TNFSF10, BCL6, BTG1, CCNG2, CDKN1B, BNIP3, GADD45A, INSR, and MXI1;
  b. Wnt target genes AXIN2, CD44, LGR5, CEMIP, MYC, CXCL8, SOX9, EPHB3, RNF43, TDGF1, ZNRF3, and DEFA6:
  c. ER target genes TFF1, GREB1, PGR, SGK3, PDZK1, IGFBP4, NRIP1, CA12, XBP1, ERBB2, ESR1, and CELSR2; and,
  d. HH target genes GLI1. PTCH1, PTCH2, CCND2, IGFBP6, MYCN, FST, RAB34, GLI3, CFLAR, S100A7, and S100A9.

In one embodiment, the kit further comprises a non-transitory computer readable storage medium having computer readable program code embodied therewith, the computer readable program code executable by at least one processor to:
  a. calculate activity level of a PI3K cellular signaling pathway in a sample isolated from the subject, wherein the PI3K cellular signaling pathway activity is calculated by:
    i. calculating an activity level of a PI3K transcription factor element in the sample, wherein the activity level of the PI3K transcription factor element in the sample is calculated by:
      1. receiving data on the expression levels of at least three PI3K target genes derived from the sample, wherein the PI3K transcription factor element controls transcription of the at least three PI3K target genes,
      2. calculating the activity levels of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and, ii. calculating the activity level of the PI3K cellular signaling pathway in the sample based on the calculated activity level of the PI3K transcription factor elements in the sample, and, b. calculate an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity levels of the additional cellular signaling pathways is calculated by:

i. calculating an activity level of a transcription factor element from the additional cellular signaling pathway in the sample, wherein the activity level of the transcription factor element of the additional cellular signaling pathway is calculated by:

1. receiving data on the expression levels of at least three target genes of the additional cellular signaling pathway derived from the sample, wherein the transcription factor element of the additional cellular signaling pathway controls transcription of the at least three target genes of the additional cellular signaling pathway, 2. calculating the activity levels of the transcription factor element of the additional cellular signaling pathway in the sample using a calibrated pathway model, wherein the calibrated pathway model compares the expression levels of the at least three target genes from the additional cellular signaling pathway in the sample with expression levels of the at least three target genes from the additional cellular signaling pathway in the calibrated pathway model which define an activity level of the transcription factor element of the additional cellular signaling pathway; and, ii. calculating the activity level of the additional cellular signaling pathway in the sample based on the calculated activity level of the transcription factor element of the additional cellular signaling pathway in the sample; and, c. calculate a risk score using a calibrated Multi-Pathway Score (MPS) model, wherein the calibrated MPS model compares the calculated activity level of the PI3K cellular signaling pathway and the calculated activity level of the additional cellular signaling pathway in the sample with an activity level of a PI3K cellular signaling pathway and activity level of the additional cellular signaling pathway determinative of the occurrence of the clinical event.

Generalized Workflow for Determining the Activity Level of PI3K, Wnt, ER, and HH Cellular Signaling The present disclosure provides new and improved methods and apparatuses as disclosed herein, to assess the functional state or activity of the PI3K, Wnt, ER, and HH cellular signaling pathways in order to calculate a risk score of a subject experiencing a particular clinical event.

Figure 12:
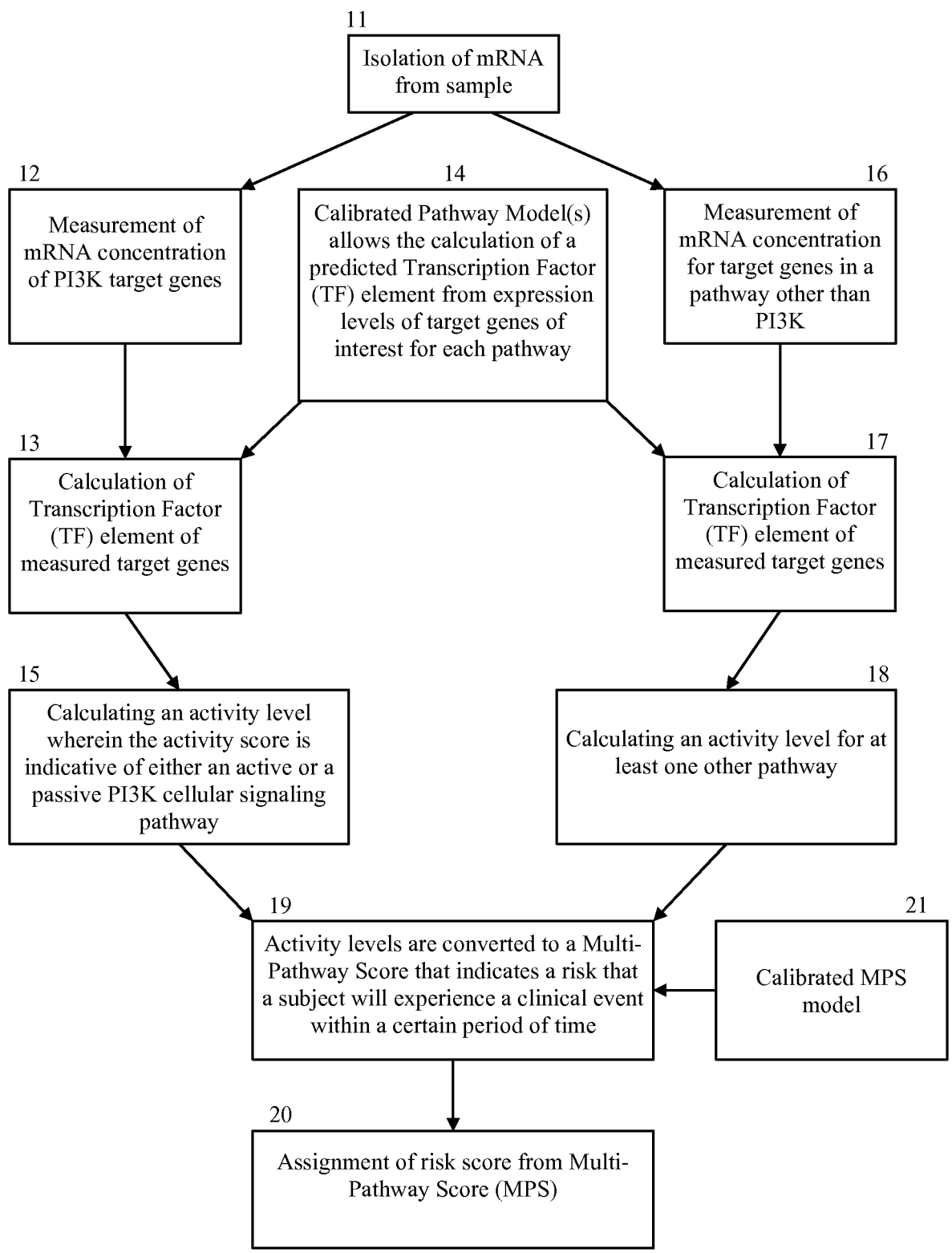
FIG. 12 shows a non-limiting exemplary flow chart for calculating the risk score based on the measurement of the expression levels of target genes of the PI3K cellular signaling pathway and additional cellular signaling pathways.

An example flow chart illustrating an exemplary calculation of the activity level of PI3K cellular signaling and other cellular signaling from a sample isolated from a subject is provided in FIG. 12. First, the mRNA from a sample is isolated (11). Second, the mRNA expression levels of a unique set of at least three or more PI3K target genes, as described herein, are measured (12) using methods for measuring gene expression that are known in the art. Next, the calculation of a transcription factor element (13) is calculated using a calibrated pathway model (14), wherein the calibrated pathway model compares the expression levels of the at least three or more target genes in the sample with expression levels of the at least three target genes in the calibrated pathway model which have been correlated with a level of a PI3K transcription factor element. Next, the activity level of the PI3K cellular signaling pathway is calculated in the sample based on the calculated levels of the PI3K transcription factor element in the sample (15).

As shown on the right hand side of FIG. 12, after calculating the PI3K transcription factor element, a transcription factor element for at least one additional cellular signaling pathways (i.e. Wnt, ER, and HH) are determined. As an example, the mRNA expression levels of a unique set of at least three or more target genes from the additional cellular signaling pathways, as described herein, are measured (16) using methods for measuring gene expression that are known in the art. Next, the calculation of the transcription factor element (17) is calculated using a calibrated pathway model (14), wherein the calibrated pathway model compares the expression levels of the at least three or more target genes in the sample with expression levels of the at least three target genes in the calibrated pathway model which have been correlated with a level of the transcription factor element of the particular cellular signaling pathway being analyzed. Next, the activity level of other cellular signaling pathways (i.e. Wnt, ER, and HH) is calculated in the sample based on the calculated level of the transcription factor element in the sample (18) specific to the particular cellular signaling pathway. Next, the activity level of the PI3K and the other cellular signaling pathways is converted to a Multi-Pathway Score (MPS) using a calibrated MPS model (21) that indicates a risk that a subject will experience a clinical event within a certain period of time (19). Finally, the sample is assigned a risk score for experiencing a clinical event based on the calculated MPS (20).

Target Genes

The present disclosure utilizes the analyses of the expression levels of unique sets of target genes. Particularly suitable target genes are described in the following text passages as well as the examples below (see, e.g., Tables 1-13 below).

Thus, in one embodiment the target gene(s) is/are selected from the group consisting of the target genes listed in Table 1, Table 2, Table 3, Table 4, Table 5, Table 6, Table 7, Table 8, Table 9, Table 10, Table 11, Table 12, or Table 13.

Provided herein is a method of identifying a subject at risk of experiencing a clinical event associated with a disease within a defined period of time comprising the steps of:

determining the activity of the PI3K pathway in the subject based at least on expression levels of one or more (i.e. one or more, two or more, three or more, four or more, five or more, six or more, seven or more, eight or more, nine or more, ten or more, eleven or more, twelve or more, etc.) target gene(s) of the PI3K pathway measured in the sample of the subject selected from the group consisting of: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10, and/or determining the activity of the Wnt pathway in the subject based at least on expression levels of one or more (i.e. one or more, two or more, three or more, four or more, five or more, six or more, seven or more, eight or more, nine or more, ten or more, eleven or more, twelve or more, etc.) target gene(s) of the Wnt pathway measured in the sample of the subject selected from the group consisting of: KIAA1199 (CEMIP), AXIN2, CD44, RNF43, MYC, TBX3, TDGF1, SOX9, ASCL2, 1L8 (CXCL8), SP5, ZNRF3, EPHB2, LGR5, EPHB3, KLF6, CCND1, DEFA6, and FZD7, and/or determining the activity of the ER pathway in the subject based at least on expression levels of one or more (i.e. one or more, two or more, three or more, four or more, five or more, six or more, seven or more, eight or more, nine or more, ten or more, eleven or more, twelve or more, etc.) target gene(s) of the ER pathway measured in the sample of the subject selected from the group consisting of; GREB1, PGR. XBP1, CA12, SOD1, CTSD. IGFBP4, TFF1, SGK3, NRIP1, CELSR2, WISP2, AP1B1, PDZK1, ERBB2, and ESR1, and/or determining the activity of the HH pathway in the subject based at least on expression levels of one or more (i.e. one or more, two or more, three or more, four or more, five or more, six or more, seven or more, eight or more, nine or more, ten or more, eleven or more, twelve or more, etc.) target gene(s) of the HH pathway measured in the sample of the subject selected from the group consisting of; GLI1. PTCH1, PTCH2. IGFBP6, SPP1, CCND2, FST, FOXL1, CFLAR, TSC22D1, RAB34, S100A9, SI00A7, MYCN, FOXM1, GLI3, TCEA2, FYN, and CTSL1.

Provided herein is a method of identifying a subject at risk of experiencing a clinical event associated with a disease within a defined period of time comprising the steps of: determining the activity of the PI3K pathway in the subject based at least on expression levels of one or more, two or more, or at least three, target gene(s) of the PI3K pathway measured in the sample of the subject selected from the group consisting of: BCL2L11, BCL6, BNIP3, BTG1, CCNG2, CDKN1B, FBXO32, GADD45A, INSR, MXI1, SOD2, and TNFSF10, and/or determining the activity of the Wnt pathway in the subject based at least on expression levels of one or more, two or more, or at least three, target gene(s) of the Wnt pathway measured in the sample of the subject selected from the group consisting of: KIAA1199 (CEMIP), AXIN2, CD44, RNF43, MYC, TDGF1, SOX9, IL8 (CXCL8), ZNRF3, LGR5, EPHB3, and DEFA6, and/or determining the activity of the ER pathway in the subject based at least on expression levels of one or more, two or more, or at least three, target gene(s) of the ER pathway measured in the sample of the subject selected from the group consisting of: GREB1, PGR, XBP1, CA12, IGFBP4, TFF1, SGK3, NRIP1, CELSR2, PDZK1, ERBB2, and ESR1, and/or determining the activity of the HH pathway in the subject based at least on expression levels of one or more, two or more, or at least three, target gene(s) of the HH pathway measured in the sample of the subject selected from the group consisting of: GLI1, PTCH1, PTCH2, IGFBP6, CCND2, FST, CFLAR. RAB34, S100A9, S100A7, MYCN, and GL13.

Provided herein is a method which comprises:

calculating the activity of the two or more cellular signaling pathways based at least on the expression levels of one or more target gene(s) of the cellular signaling pathways measured in a sample of the subject.

Provided herein is a method wherein the calculating comprises:

calculating the activity of the PI3K pathway in the subject based at least on expression levels of one or more, two or more, or at least three, target gene(s) of the PI3K pathway measured in the sample of the subject selected from the group consisting of: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10, and/or calculating the activity of the Wnt pathway in the subject based at least on expression levels of one or more, two or more, or at least three, target gene(s) of the Wnt pathway measured in the sample of the subject selected from the group consisting of; KIAA1199. AXIN2, CD44, RNF43, MYC, TBX3, TDGF1, SOX9, ASCL2, IL8, SP5, ZNRF3, EPHB2, LGR5, EPHB3, KLF6, CCND1, DEFA6, and FZD7, and/or calculating the activity of the ER pathway in the subject based at least on expression levels of one or more, two or more, or at least three, target gene(s) of the ER pathway measured in the sample of the subject selected from the group consisting of: GREB1, PGR, XBP1, CA12, SOD1, CTSD, IGFBP4, TFF1, SGK3, NRIP1, CELSR2, WISP2, and AP1B1, and/or calculating the activity of the HH pathway in the subject based at least on expression levels of one or more, two or more, or at least three, target gene(s) of the HH pathway measured in the sample of the subject selected from the group consisting of: GLI1, PTCH1, PTCH2, IGFBP6, SPP1, CCND2, FST, FOXL1, CFLAR, TSC22D1, RAB34, SI00A9, S100A7, MYCN, FOXM1, GLI3, TCEA2, FYN, and CTSL1.

In one embodiment, the calculating is further based on:

(i) expression levels of at least one target gene of the PI3K pathway measured in the sample of the subject selected from the group consisting of: ATP8A1, C10orf10, CBLB, DDB1, DYRK2, ERBB3, EREG, EXT1, FGFR2, IGF1R, IGFBP1, IGFBP3, LGMN, PPM1D, SEMA3C, SEPP1, SESN1, SLC5A3, SMAD4, and TLE4, and/or (ii) expression levels of at least one target gene of the PI3K pathway measured in the sample of the subject selected from the group consisting of: ATG14, BIRC5, IGFBP1, KLF2, KLF4, MYOD1, PDK4, RAG1, RAG2, SESN1, SIRT1, STK11 and TXNIP, and/or expression levels of at least one target gene of the Wnt pathway measured in the sample of the subject selected from the group consisting of; NKD1, OAT, FAT1, LEF1, GLUL, REG1B, TCF7L2, COL18A1, BMP7, SLC1A2, ADRA2C, PPARG, DKK1, HNF1A, and LECT2, and/or expression levels of at least one target gene of the ER pathway measured in the sample of the subject selected from the group consisting of: RARA, MYC, DSCAM, EBAG9, COX7A2L, ERBB2, PISD, KRT19, HSPB1, TRIM25, PTMA, COL18A1, CDH26, NDUFV3, PRDM15, ATP5J, and ESR1, and/or expression levels of at least one target gene of the HH pathway measured in the sample of the subject selected from the group consisting of; BCL2, FOXA2, FOXF1, H19, HHIP, IL1R2, JAG2, JUP, MIF, MYLK, NKX2.2, NKX2.8, PITRM1, and TOM1.

In one embodiment, the PI3K target genes are selected from the group consisting of: ATP8A1, BCL2L11, BNIP3, BTG1, C10orf10, CAT, CBLB, CCND1, CCND2, CDKN1B, DDB1, DYRK2, ERBB3, EREG, ESR1, EXT1, FASLG, FGFR2, GADD45A, IGF1R, IGFBP1, IGFBP3, INSR, LGMN, MXI1, PPM1D, SEMA3C, SEPP1, SESN1, SLC5A3, SMAD4, SOD2, TLE4, and TNFSF10.

In one embodiment, the Wnt target genes are selected from the group consisting of: ADRA2C, ASCL2, AXIN2, BMP7, CCND1, CD44, COL18A1, DEFA6, DKK1, EPHB2, EPHB3, FAT1, FZD7, GLUL, HNF1A, 1L8, KIAA1199 (CEMIP), KLF6, LECT2, LEF1, LGR5, MYC, NKD1, OAT, PPARG, REG1B, RNF43, SLC1A2, SOX9, SP5, TBX3, TCF7L2, TDGF1, and ZNRF3.

In one embodiment, the ER target genes are selected from the group consisting of: AP1B1, ATP5J, COL18A1, COX7A2L, CTSD, DSCAM, EBAG9, ESR1, HSPB1, KRT19, NDUFV3, NR1P1, PGR, PISD, PRDM15, PTMA, RARA, SOD1, TFF1, TRIM25, XBP1, GREB1, IGFBP4, MYC, SGK3, WISP2. ERBB2, CA12, CDH26, and CELSR2.

In one embodiment, the HH target genes are selected from the group consisting of: GLI1, PTCH1, PTCH2, HHIP, SPP1, TSC22D1, CCND2, H19, IGFBP6, TOM1, JUP, FOXA2, MYCN. NKX2-2, NKX2-8, RAB34, MIF, GLI3, FST, BCL2, CTSL1, TCEA2, MYLK. FYN, PITRM1, CFLAR, IL1R2, S100A7, SI00A9, CCND1, JAG2, FOXM1, FOXF1, and FOXL1.

If the calculating of the activity of the PI3K pathway is further based both on expression levels of at least one target gene of the PI3K pathway selected from the group (i) and on expression levels of at least one target gene of the PI3K pathway selected from the group (ii), the target genes IGFBP1 and SESN1, which are mentioned above with respect to both groups, may only be contained in one of the groups.

The "target gene(s)" are for example "direct target genes" and/or "indirect target genes" (as described herein).

Measuring Levels of Gene Expression

Data derived from the unique set of target genes described herein is further utilized to determine the activity level of the cellular signaling pathways using the methods described herein.

Methods for analyzing gene expression levels in isolated samples are generally known. For example, methods such as Northern blotting, the use of PCR, nested PCR, quantitative real-time PCR (qPCR). RNA-seq, or microarrays can all be used to derive gene expression level data. All methods known in the art for analyzing gene expression of the target genes are contemplated herein.

Methods of determining the expression product of a gene using PCR based methods may be of particular use. In order to quantify the level of gene expression using PCR, the amount of each PCR product of interest is typically estimated using conventional quantitative real-time PCR (qPCR) to measure the accumulation of PCR products in real time after each cycle of amplification. This typically utilizes a detectible reporter such as an intercalating dye, minor groove binding dye, or fluorogenic probe whereby the application of light excites the reporter to fluoresce and the resulting fluorescence is typically detected using a CCD camera or photomultiplier detection system, such as that disclosed in U.S. Pat. No. 6,713,297 which is hereby incorporated by reference.

In some embodiments, the probes used in the detection of PCR products in the quantitative real-time PCR (qPCR) assay can include a fluorescent marker. Numerous fluorescent markers are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™.

Additional fluorescent markers can include IDT ZEN Double-Quenched Probes with traditional 5' hydrolysis probes in qPCR assays. These probes can contain, for example, a 5' FAM dye with either a 3' TAMRA Quencher, a 3' Black Hole Quencher (BHQ, Biosearch Technologies), or an internal ZEN Quencher and 3' Iowa Black Fluorescent Quencher (IBFQ).

Fluorescent dyes useful according to the disclosure can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference.

Another useful method for determining target gene expression levels includes RNA-seq, a powerful analytical tool used for transcriptome analyses, including gene expression level difference between different physiological conditions, or changes that occur during development or over the course of disease progression.

Another approach to determine gene expression levels includes the use of microarrays for example RNA and DNA microarray, which are well known in the art. Microarrays can be used to quantify the expression of a large number of genes simultaneously.

Calibration of Multi-Pathway Score (MPS) Model and Calculation of Multi-Pathway Risk Score (MPS)

As contemplated herein, a risk score corresponding to the risk that a clinical event will occur can be determined using a calibrated Multi-Pathway Score (MPS) model containing activity levels of the cellular signaling pathways associated with the clinical event, as further described below. The calibrated MPS model compares the calculated activity level of the PI3K cellular signaling pathway and the calculated activity levels of one or more of the Wnt cellular signaling pathway, ER cellular signaling pathway, or HH cellular signaling pathway in the sample with an activity level of the PI3K cellular signaling pathway and an activity level of one or more of Wnt, ER, or HH cellular signaling pathway determinative of the occurrence of the clinical event.

A calibrated Multi-Pathway Score (MPS) model as used in the present disclosure can be calibrated with readily available clinical data on the clinical event of interest and the calculated pathway activities. A non-limiting exemplary flow chart for calibrating a MPS model with survival data is shown in FIG. 12. As an initial step, relevant pathway activities calculated using calibrated pathway models are retrieved from a pathway activities database (201). The pathway activities database contains PI3K pathway activities (205) and the pathway activities for at least one additional pathway. For example, the pathway activities database contains ER pathway activities (202), Wnt pathway activities (203), HH pathway activities (204), and PI3K pathway activities (205). The IDs of a particular training set of samples (218) is then employed to receive the relevant pathway activities (219) and, for example, survival data (220) (if survival is the clinical event being analyzed) which is received from a survival data database (221). The pathway activities are then selected (222) with an output of $P_e$, $P_w$, $P_h$, and $P_p$ in case of ER pathway activities, Wnt pathway activities, HH pathway activities, and PI3K pathway activities. The survival data is converted to the variables Surv and cens (223) reflecting the survival time and censoring data within a given time period that the MPS will be used for. The pathway activities and survival data are then fit to a Cox's proportional hazard model (224) which results in a fitted Cox's proportional hazard model (225). From the Cox's proportional hazard model the Cox's coefficients are collected (226) and then assigned to weights (227) with the output $w_e$, $w_w$, $w_h$, and $w_p$. The MPS structure (228) and weights are taken together to calibrate the MPS model (229) outputting a calibrated MPS model (210)

Figure 13:
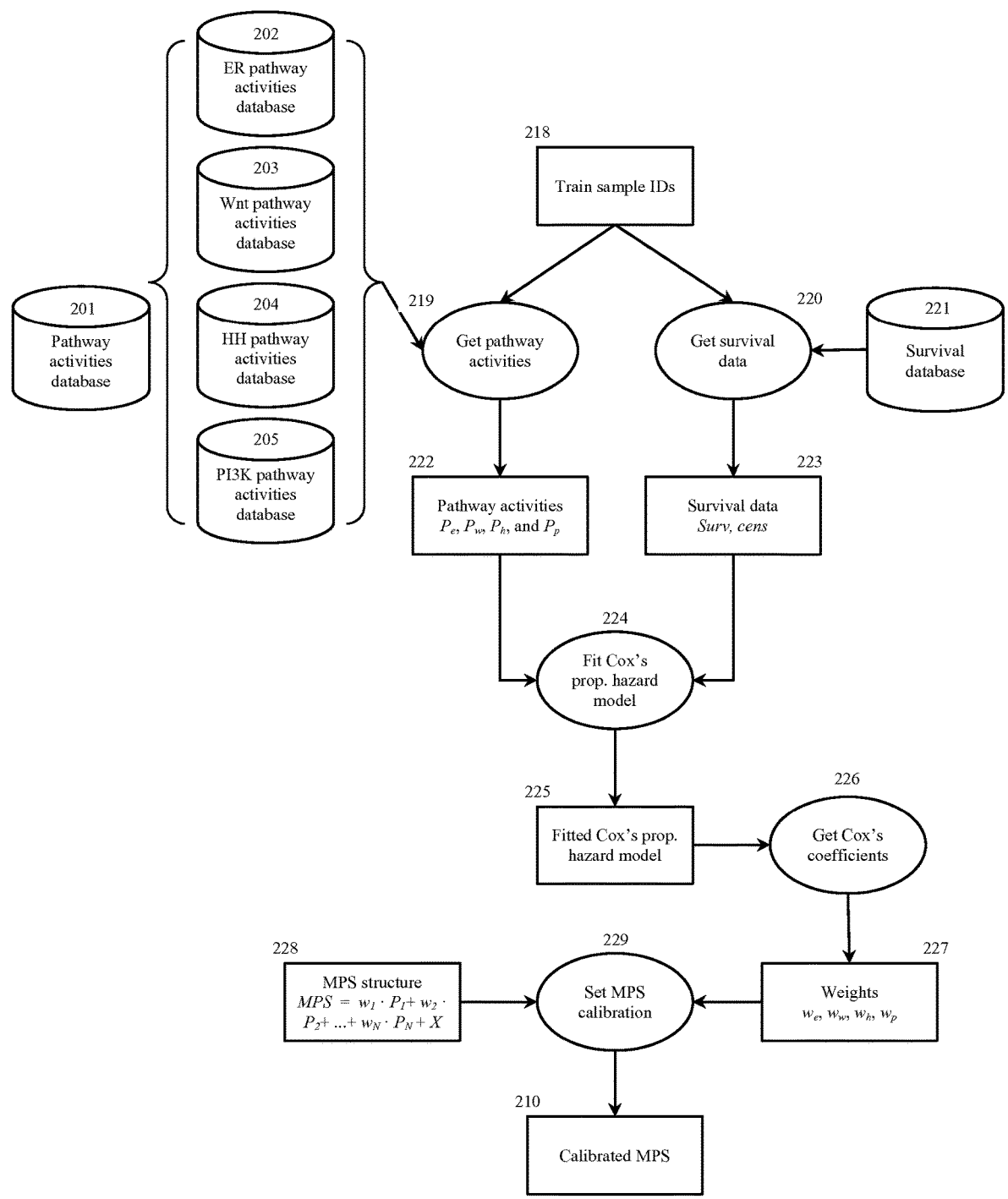
FIG. 13 is a non-limiting exemplary flow chart for calibrating a Multi-Pathway Score (MPS) model with survival data.
Figure 14:
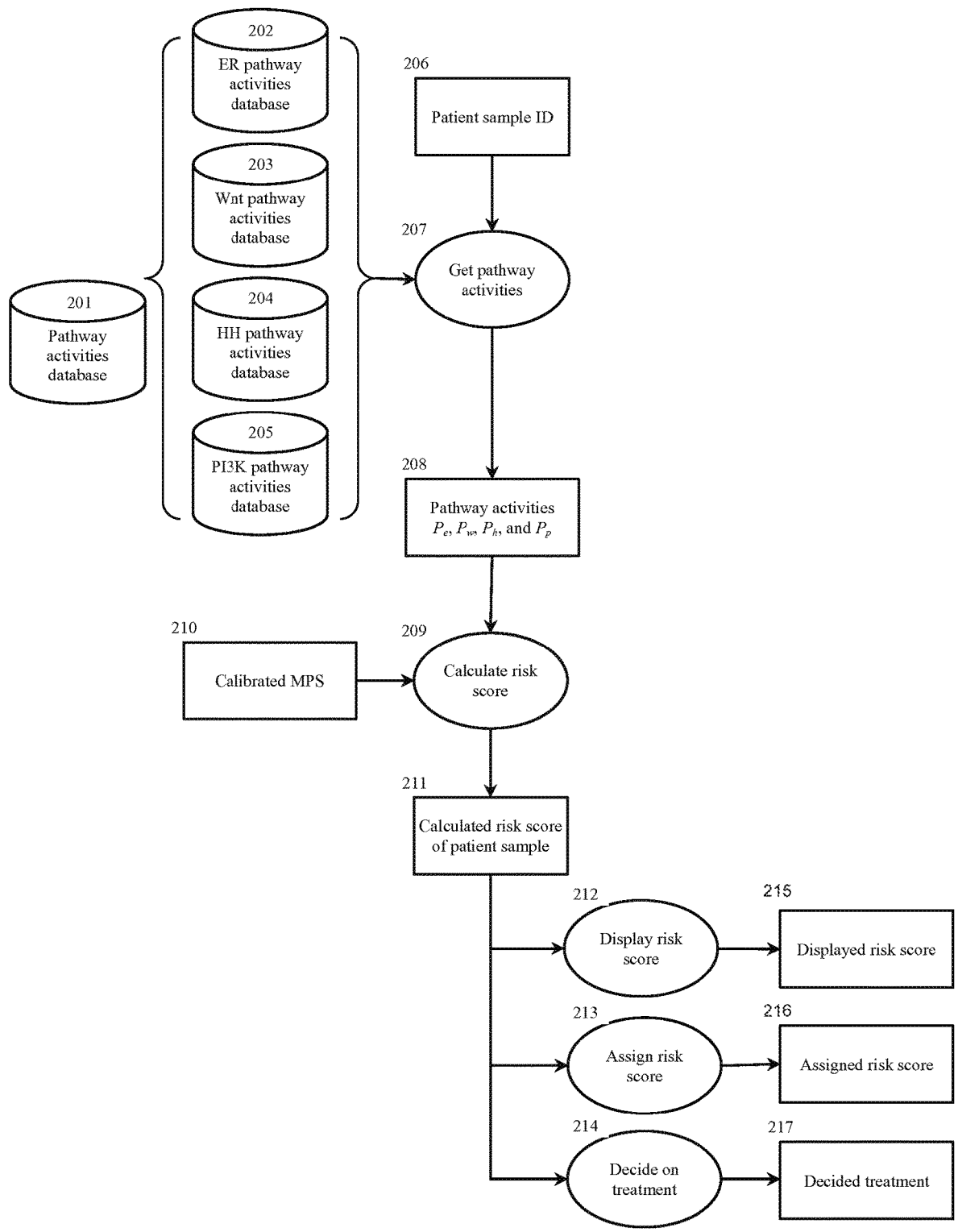
FIG. 14 is a non-limiting exemplary flow chart for calculating a risk score from a calibrated Multi-Pathway Score (MPS) model.

A non-limiting exemplary flow chart for calculating a risk score from a calibrated MPS model is shown in FIG. 13. As an initial step, relevant pathway activities calculated using calibrated pathway models are retrieved from a pathway activities database (201). The pathway activities database contains PI3K pathway activities (205) and the pathway activities for at least one additional pathway. For example, the pathway activities database contains ER pathway activities (202), Wnt pathway activities (203). HH pathway activities (204), and PI3K pathway activities (205). The patients sample is then identified (206) and initial pathway activities are collected from the sample and database as either a measurement of transcription factors or gene expression levels, for the relevant pathways (207). Total activity levels of each of the relevant pathways are then calculated (208) with an output of $P_e$, $P_w$, $P_h$, and $P_p$. These activities are then converted to a risk score (209) using a calibrated MPS model (210). This initial risk score can be further adjusted with other relevant data to produce a final risk score for the patient (211), which can then be used to display (212), assign (213), or decide on a treatment (214), producing the outcomes of a displayed risk score (215), an assigned risk score (216), or a decided treatment (217) respectively.

The calculating of the activity of the cellular signaling pathways in the subject may be performed, for example, by (i) evaluating at least a portion of a probabilistic model, for example a Bayesian network, representing the cellular signaling pathways for a set of inputs including at least the expression levels of the one or more target gene(s) of the cellular signaling pathways measured in a sample of the subject, (ii) estimating a level in the subject of at least one transcription factor (TF) element, the at least one TF element controlling transcription of the one or more target gene(s) of the cellular signaling pathways, the estimating being based at least in part on conditional probabilities relating the at least one TF element and the expression levels of the one or more target gene(s) of the cellular signaling pathway measured in the sample of the subject, and (iii) calculating the activity of the cellular signaling pathways based on the estimated level of the transcription factor in the sample of the subject. This is described in detail in the published international patent application WO 2013/011479 A2 ("Assessment of cellular signaling pathway activity using probabilistic modeling of target gene expression"), the contents of which are herewith incorporated in their entirety.

In an exemplary alternative, the calculating of the activity of one or more of the cellular signaling pathways in the subject may be performed by, for example, (i) determining a level of a transcription factor (TF) element in the sample of the subject, the TF element controlling transcription of the one or more target gene(s) of the cellular signaling pathway, the determining being based at least in part on evaluating a mathematical model relating expression levels of the one or more target gene(s) of the cellular signaling pathway to the level of the TF element, the model being based at least in part on one or more linear combination(s) of expression levels of the one or more target gene(s), and (ii) calculating the activity of the cellular signaling pathway in the subject based on the determined level of the TF element in the sample of the subject. This is described in detail in the published international patent application WO 2014/102668 A2 ("Assessment of cellular signaling pathway activity using linear combination(s) of target gene expressions").

One embodiment provides a method wherein the cellular signaling pathways comprise the PI3K pathway and/or the Wnt pathway and/or the ER pathway and/or the HH pathway, and wherein the risk score is defined such that the indicated risk that the subject will experience the clinical event within the certain period of time monotonically increases with an increasing inferred activity of the PI3K pathway and/or an increasing inferred activity of the Wnt pathway and/or an increasing inferred activity of the HH pathway and/or monotonically decreases with an increasing inferred activity of the ER pathway.

In one embodiment, a method is provided wherein the risk score is defined such that the indicated risk that the subject will experience the clinical event within the certain period of time monotonically increases with an increasing inferred activity of the PI3K pathway.

In one embodiment, the combination of the inferred activities comprises a sum that includes the term $w_p \cdot P_p$ and one or more of the terms $w_w \cdot P_w$, $w_e \cdot P_e$, and $w_h \cdot P_h$, wherein $P_p$, $P_w$, $P_e$, and $P_h$ denote the inferred activity of the PI3K pathway, the Wnt pathway, the ER pathway, and the HH pathway, respectively, $w_p$, $w_w$, and $w_h$ are positive constant weighting coefficients, $w_e$ is a negative constant weighting coefficient, and the indicated risk that the subject will experience the clinical event within the certain period of time monotonically increases with an increasing value of the sum.

In certain embodiments, the constant weighting coefficients $w_p$, $w_w$, $w_e$, and $w_h$ are or have each been determined based on the value of the Cox's coefficient resulting from fitting a Cox proportional hazard model for the respective cellular signaling pathway to clinical data. For example, the sign of the coefficient estimate indicates whether the pathway activity is either protective for the clinical event in case of a negative coefficient or predicts a poorer or worse prognosis in case of a positive coefficient. The modulus of the coefficient indicates the strength of the risk score with respect to prognosis.

In one embodiment, the clinical event is cancer metastasis and $w_p$, $w_w$ and $w_h$ are non-negative constant weighting coefficients, and $w_e$ is a non-positive constant weighting coefficient. With these coefficients the MPS show the indicated risk that the subject will experience the clinical event within the certain period of time monotonically increases with an increasing value of the sum.

Transcription Factor Elements

Each of the PI3K pathway, the Wnt pathway, the ER pathway, and the HH pathway is defined as the cellular signaling pathway that ultimately leads to transcriptional activity of the transcription factor (TF) complexes associated with the pathway. These consist of a FOXO family member, β-catenin/TCF4, the ERα dimer, and a GLI family member, respectively.

The present disclosure concentrates on the PI3K pathway and the FOXO TF family, the activity of which is substantially correlated with the activity of the PI3K pathway, i.e., the activity of the FOXO TF complex is substantially correlated with the activity of the PI3K pathway, whereas the inactivity of the FOXO TF complex is substantially correlated with the inactivity of the PI3K pathway.

As a non-limiting generalized example, FIG. 1 provides an exemplary flow diagram used to determine activity level of cellular signaling pathways based on a computer implemented mathematical model constructed of three layers of nodes: (a) a transcription factor (TF) element (for example, but not limited to being, discretized into the states "absent" and "present" or as a continuous observable) in a first layer 1; (b) target gene(s) $TG_1$, $TG_2$, $TG_n$ (for example, but not limited to being, discretized into the states "down" and "up" or as a continuous observable) in a second layer 2, and; (c) measurement nodes linked to the expression levels of the target gene(s) in a third layer 3. The expression levels of the target genes can be determined by, for example, but not limited to, microarray probesets $PS_{1,1}$, $PS_{1,2}$, $PS_{1,3}$, $PS_{2,1}$, $PS_{n,1}$, $PS_{n,m}$ (for example, but limited to being, discretized into the states "low" and "high" or as a continuous observable), but could also be any other gene expression measurements such as, for example, RNAseq or RT-qPCR. The expression of the target genes depends on the activation of the respective transcription factor element, and the measured intensities of the selected probesets depend in turn on the expression of the respective target genes. The calibrated model is used to calculate pathway activities by first determining probeset intensities, i.e., the expression level of the target genes, and calculating backwards in the model what the probability is that the transcription factor element must be present.

Kits for Calculating PI3K, Wnt, ER, and/or HH Signaling Pathway Activity

In some embodiments, the present disclosure utilizes kits comprising one or more components for determining or measuring target gene expression levels in a sample, for example, primer and probe sets for the analyses of the expression levels of unique sets of target genes (See Target Gene discussion above). Particularly suitable oligo sequences for use as primers and probes for inclusion in a kit are described in the following text passages and, for example, Tables 16, Table 17, Table 18, Table 19, and Table 20.

Also contemplated herein is a kit comprising one or more components for measuring a set of unique target genes as described further below.

In one non-limiting embodiment, the kit includes one or more components for measuring the expression levels of:
one or more, two or more, or at least three, target gene(s) of the PI3K pathway selected from the group consisting of: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10.

and/or one or more, two or more, or at least three, target gene(s) of the Wnt pathway selected from the group consisting of: KIAA1199 (CEMIP), AXIN2, CD44, RNF43, MYC, TBX3, TDGF1, SOX9, ASCL2, IL8 (CXCL8), SP5, ZNRF3, EPHB2, LGR5. EPHB3, KLF6, CCND1, DEFA6, and FZD7, and/or one or more, two or more, or at least three, target gene(s) of the ER pathway selected from the group consisting of: GREB1, PGR, XBP1, CA12, SOD1, CTSD, IGFBP4, TFF1, SGK3, NRIP1, CELSR2, WISP2, AP1B1, PDZK1, ERBB2, and ESR1, and/or one or more, two or more, or at least three, target gene(s) of the HH pathway selected from the group consisting of: GLI1, PTCH1, PTCH2, IGFBP6, SPP1, CCND2, FST, FOXL1, CFLAR. TSC22D1, RAB34, S100A9, S100A7, MYCN, FOXM1, GLI3, TCEA2, FYN, and CTSL1.

In an additional non-limiting embodiment, the kit includes one or more components for measuring the expression levels of:
one or more, two or more, or at least three, target gene(s) of the PI3K pathway selected from the group consisting of: BCL2L11, BCL6, BNIP3, BTG1, CCNG2, CDKN1B, FBXO32, GADD45A, INSR, MXI1, SOD2, and TNFSF10, and/or one or more, two or more, or at least three, target gene(s) of the Wnt pathway selected from the group consisting of: KIAA1199 (CEMIP), AXIN2, CD44, RNF43, MYC, TDGF1, SOX9, IL8 (CXCL8), ZNRF3, LGR5, EPHB3, and DEFA6, and/or one or more, two or more, or at least three, target gene(s) of the ER pathway selected from the group consisting of: GREB1, PGR, XBP1, CA12, IGFBP4, TFF1, SGK3, NRIP1, CELSR2, PDZK1, ERBB2, and ESR1, and/or one or more, two or more, or at least three, target gene(s) of the HH pathway selected from the group consisting of: GLI1, PTCH1, PTCH2, IGFBP6, CCND2, FST, CFLAR, RAB34, S100A9, S100A7, MYCN, and GLI3.

In one non-limiting embodiment, the kit includes one or more components for measuring the expression levels of one or more, two or more, or at least three, PI3K target genes selected from the group consisting of: AGRP, BCL2L11, BCL6, BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3. RBL2, SOD2, and TNFSF10. In another embodiment, the PI3K target genes are selected from the group consisting of: BCL2L11, BCL6, BNIP3, BTG1, CCNG2, CDKN1B, FBXO32, GADD45A, INSR, MXI1, SOD2, and TNFSF10. In one embodiment, the one or more components are selected from the primers and probes listed in Table 16.

In one non-limiting embodiment, the kit includes one or more components for measuring the expression levels of one or more, two or more, or at least three, Wnt target genes selected from the group consisting of: CEMIP, AXIN2, CD44. RNF43, MYC, TBX3, TDGF1, SOX9, ASCL2, CXCL8, SP5, ZNRF3, EPHB2, LGR5, EPHB3, KLF6, CCND1, DEFA6, and FZD7. In another embodiment, the Wnt target genes are selected from the group consisting of: CEMIP, AXIN2, CD44, RNF43, MYC, TDGF1, SOX9, CXCL8, ZNRF3, LGR5, EPHB3, and DEFA6. In one embodiment, the one or more components are selected from the primers and probes listed in Table 17.

In one non-limiting embodiment, the kit includes one or more components for measuring the expression levels of one or more, two or more, or at least three, ER target genes selected from the group consisting of: GREB1, PGR, XBP1, CA12, SOD1, CTSD, IGFBP4, TFF1, SGK3, NRIP1, CELSR2, WISP2, AP1B1, PDZK1, ERBB2, and ESR1. In another embodiment, the ER target genes are selected from the group consisting of: GREB1, PGR, XBP1, CA12, IGFBP4, TFF1, SGK3, NRIP1, CELSR2, PDZK1, ERBB2, and ESR1. In one embodiment, the one or more components are selected from the primers and probes listed in Table 18.

In one non-limiting embodiment, the kit includes one or more components for measuring the expression levels of one or more, two or more, or at least three, HH target genes selected from the group consisting of; GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN, and CTSL1. In another embodiment, the HH target genes are selected from the group consisting of: GLI1, PTCH1, PTCH2, IGFBP6, CCND2, FST, CFLAR, RAB34, S100A9, S100A7, MYCN, and GLI3. In one embodiment, the one or more components are selected from the primers and probes listed in Table 19.

In one embodiment, the kit comprises an apparatus comprising a digital processor. In another embodiment, the kit comprises a non-transitory storage medium storing instructions that are executable by a digital processing device. In yet another embodiment, the kit comprises a computer program comprising program code means for causing a digital processing device to perform the methods described herein.

In an additional embodiment, the kit contains one or more components that are selected from the group consisting of: a DNA array chip, an oligonucleotide array chip, a protein array chip, an antibody, a plurality of probes, RNA sequencing and a set of primers. In one embodiment, the kit contains a plurality of probes. In one embodiment, the kit contains a set of primers. In one embodiment, the kit contains a 6, 12, 24, 48, 96, or 384-well PCR plate. In one embodiment, the kit includes a 96 well PCR plate. In one embodiment, the kit includes a 384 well PCR plate.

In one embodiment, the kit further includes a non-transitory storage medium containing instructions that are executable by a digital processing device to perform a method according to the present disclosure as described herein. In one embodiment, the kit includes an identification code that provides access to a server or computer network for analyzing the activity level of the PI3K, Wnt, ER, and HH cellular signaling pathways based on the expression levels of the target genes and the methods described herein.

In one embodiment, provided herein is a kit for identifying a subject at risk of experiencing a clinical event associated with a disease within a defined period of time comprising: a) one or more components capable of measuring the expression levels of at least three PI3K signaling target genes selected from ATP8A1, BCL2L111, BNIP3, BTG1, C10orf10, CAT, CBLB, CCND1, CCND2, CDKN1B, DDB1, DYRK2, ERBB3, EREG, ESR1, EXT1, FASLG, FGFR2, GADD45A, IGF1R, IGFBP1, IGFBP3, INSR, LGMN, MXI1, PPMID, SEMA3C, SEPP1, SESN1, SLC5A3, SMAD4, SOD2, TLE4, and TNFSF10; b) one or more components capable of measuring the expression levels of a set of at least one other cellular signaling pathway target genes, wherein the other cellular signaling pathway target genes are selected from Wnt cellular signaling pathway target genes, ER cellular signaling pathway target genes, and HH cellular signaling pathway target genes; and, c) a non-transitory computer readable storage medium having computer readable program code embodied therewith, the computer readable program code executable by at least one processor.

In one embodiment, provided herein is a kit comprising one or more components (e.g., primers and probes) capable of measuring the expression levels of: a) PI3K cellular signaling target genes selected from FBXO32, BCL2L11, SOD2, TNFSF10, BCL6, BTG1, CCNG2, CDKN1B, BNIP3, GADD45A, INSR, and MXI1b) Wnt target genes AXIN2, CD44, LGR5, CEMIP, MYC, CXCL8, SOX9, EPHB3, RNF43, TDGF1, ZNRF3, and DEFA6; c) ER target genes CDH26, SGK3, PGR, GREB1, CA12, XBP1, CELSR2, WISP2, DSCAM, ERBB2, CTSD, TFF1, and NRIP; and, d) HH target genes TFF1, GREB1, PGR, SGK3, PDZK1, IGFBP4, NRIP1, CA12, XBP1, ERBB2, ESR1, and CELSR2.

In another embodiment, provided herein is a kit comprising one or more components (e.g., primers and probes) capable of measuring the expression levels of: a) at least three PI3K signaling target genes selected from FBXO32, BCL2L11, SOD2, TNFSF10, BCL6, BTG1, CCNG2, CDKN1B, BNIP3, GADD45A, INSR, and MXI1; b) at least three Wnt target genes selected from AXIN2, CD44, LGR5, CEMIP, MYC, CXCL8, SOX9, EPHB3, RNF43, TDGF1, ZNRF3, and DEFA6; c) at least three ER target genes selected from CDH26, SGK3, PGR, GREB1, CA12, XBP1, CELSR2, WISP2, DSCAM, ERBB2, CTSD, TFF1, and NRIP; and, d) at least three HH target genes selected from TFF1, GREB1, PGR, SGK3, PDZK1, IGFBP4, NRIP1, CA12, XBP1, ERBB2, ESR1, and CELSR2.

In one embodiment, provided herein is a kit for measuring the expression levels of cellular signaling target genes in a sample isolated from a subject comprising: a) a set of polymerase chain reaction primers directed to at least three PI3K cellular signaling pathway target genes from a sample isolated from a subject; b) a set of probes directed to the at least three PI3K cellular signaling pathway target genes; c) a set of polymerase chain reaction primers directed to a set of at least three target genes from at least one other cellular signaling pathways, wherein the other cellular signaling pathway genes are selected from Wnt cellular signaling pathway target genes, ER cellular signaling pathway target genes, and HH cellular signaling pathway target genes; and, d) a set of probes directed to the at least one other cellular signaling pathway target genes.

Target Gene Expression Level Determination Procedure

Figure 15:
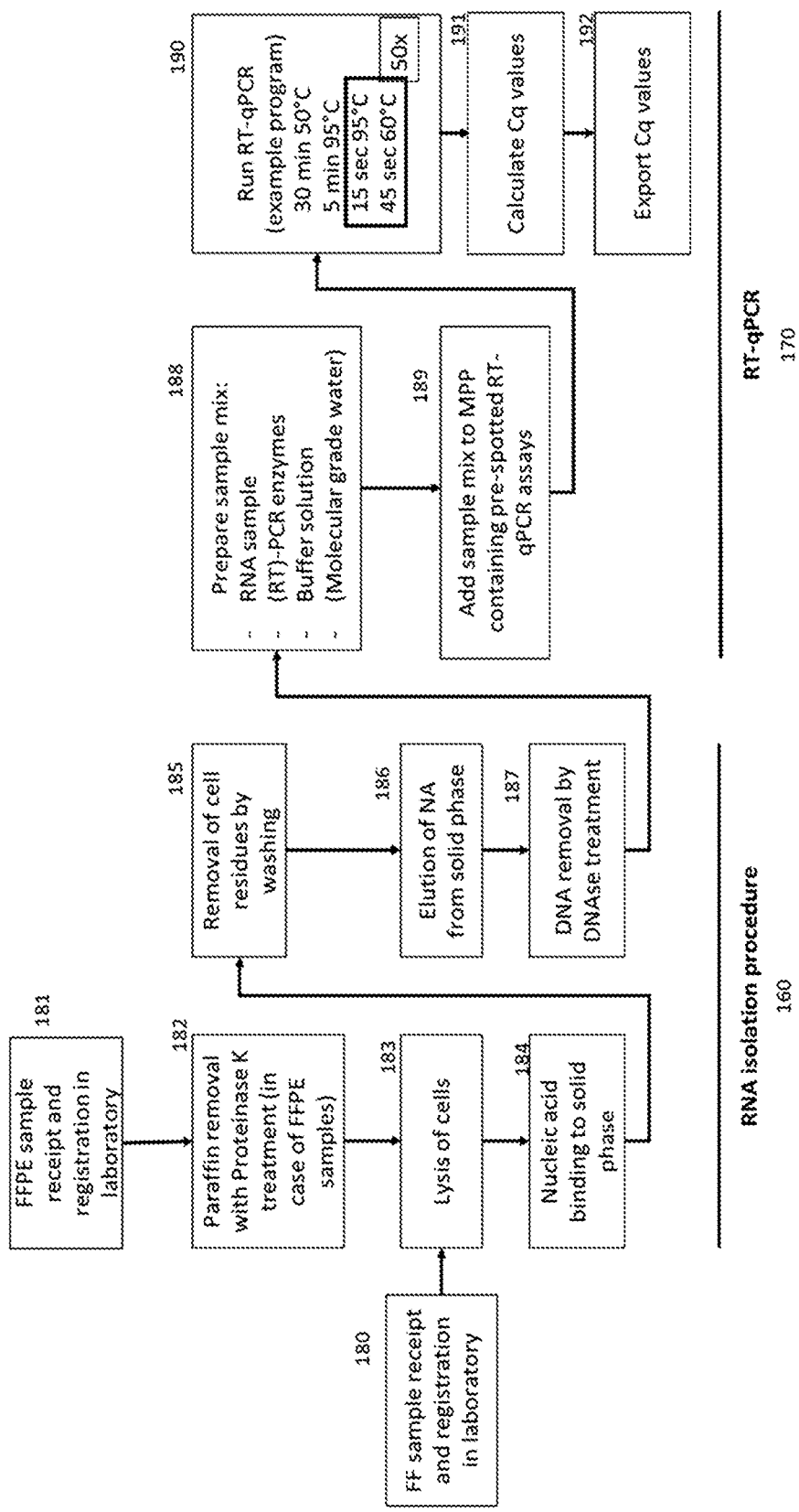
FIG. 15 shows a non-limiting exemplary flow chart for determining Cq values from RT-qPCR analysis of the target genes of the cellular signaling pathways.

A non-limiting exemplary flow chart for deriving target gene expression levels from a sample isolated from a subject is shown in FIG. 15, which shows an RNA isolation procedure (160) and an RT-qPCR (170). In one exemplary embodiment, samples are received and registered in a laboratory. Samples can include, for example, Formalin-Fixed, Paraffin-Embedded (FFPE) samples (181) or fresh frozen (FF) samples (180). FF samples can be directly lysed (183). For FFPE samples, the paraffin can be removed with a heated incubation step upon addition of Proteinase K (182).

Cells are then lysed (183), which destroys the cell and nuclear membranes which makes the nucleic acid (NA) available for further processing. The nucleic acid is bound to a solid phase (184) which could for example, be beads or a filter. The nucleic acid is then washed with washing buffers to remove all the cell debris which is present after lysis (185). The clean nucleic acid is then detached from the solid phase with an elution buffer (186). The DNA is removed by DNAse treatment to ensure that only RNA is present in the sample (187). The nucleic acid sample can then be directly used in the RT-qPCR sample mix (188). The RT-qPCR sample mixes contains the RNA sample, the RT enzyme to prepare cDNA from the RNA sample and a PCR enzyme to amplify the cDNA, a buffer solution to ensure functioning of the enzymes and can potentially contain molecular grade water to set a fixed volume of concentration. The sample mix can then be added to a multiwell plate (i.e., 96 well or 384 well plate) which contains dried RT-qPCR assays (189).

The RT-qPCR can then be run in a PCR machine according to a specified protocol (190). An example PCR protocol includes i) 30 minutes at 50° C.; ii) 5 minutes at 95° C.; iii) 15 seconds at 95° C.; iv) 45 seconds at 60° C.: v) 50 cycles repeating steps iii and iv. The Cq values are then determined with the raw data by using the second derivative method (191). The Cq values are exported for analysis (192).

Computer Programs, Computer Implemented Methods, and Clinical Decision Support (CDS) Systems As contemplated herein, the calculation of cellular pathway signaling activity in the sample is performed on a computerized device having a processor capable of executing a readable program code for calculating the cellular signaling pathway activity in the sample according to the methods described above.

In accordance with another disclosed aspect, an apparatus comprises a digital processor configured to perform a method according to the disclosure as described herein.

In accordance with another disclosed aspect, a non-transitory storage medium stores instructions that are executable by a digital processing device to perform a method according to the disclosure as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, an apparatus comprises a digital processor configured to perform a method according to the present disclosure as described herein.

In accordance with another disclosed aspect, a computer program comprises program code means for causing a digital processing device to perform a method according to the disclosure as described herein. The digital processing device may be a handheld device (e.g., a personal data assistant or smartphone), a notebook computer, a desktop computer, a tablet computer or device, a remote network server, or so forth.

In one embodiment, a computer program or system is provided for predicting the activity status of a transcription factor element in a human cancer sample that includes a means for receiving data corresponding to the expression level of one or more target genes in a sample from a host. In some embodiments, a means for receiving data can include, for example, a processor, a central processing unit, a circuit, a computer, or the data can be received through a website.

In one embodiment, a computer program or system is provided for predicting the activity status of a transcription factor element in a human cancer sample that includes a means for displaying the pathway signaling status in a sample from a host. In some embodiments, a means for displaying can include a computer monitor, a visual display, a paper print out, a liquid crystal display (LCD), a cathode ray tube (CRT), a graphical keyboard, a character recognizer, a plasma display, an organic light-emitting diode (OLED) display, or a light emitting diode (LED) display, or a physical print out.

In accordance with another disclosed aspect, a signal represents a risk score that indicates a risk that a clinical event will occur within a certain period of time, wherein the risk score resulted from performing a method according to the disclosure as described herein. The signal may be an analog signal or it may be a digital signal.

Figure 11:
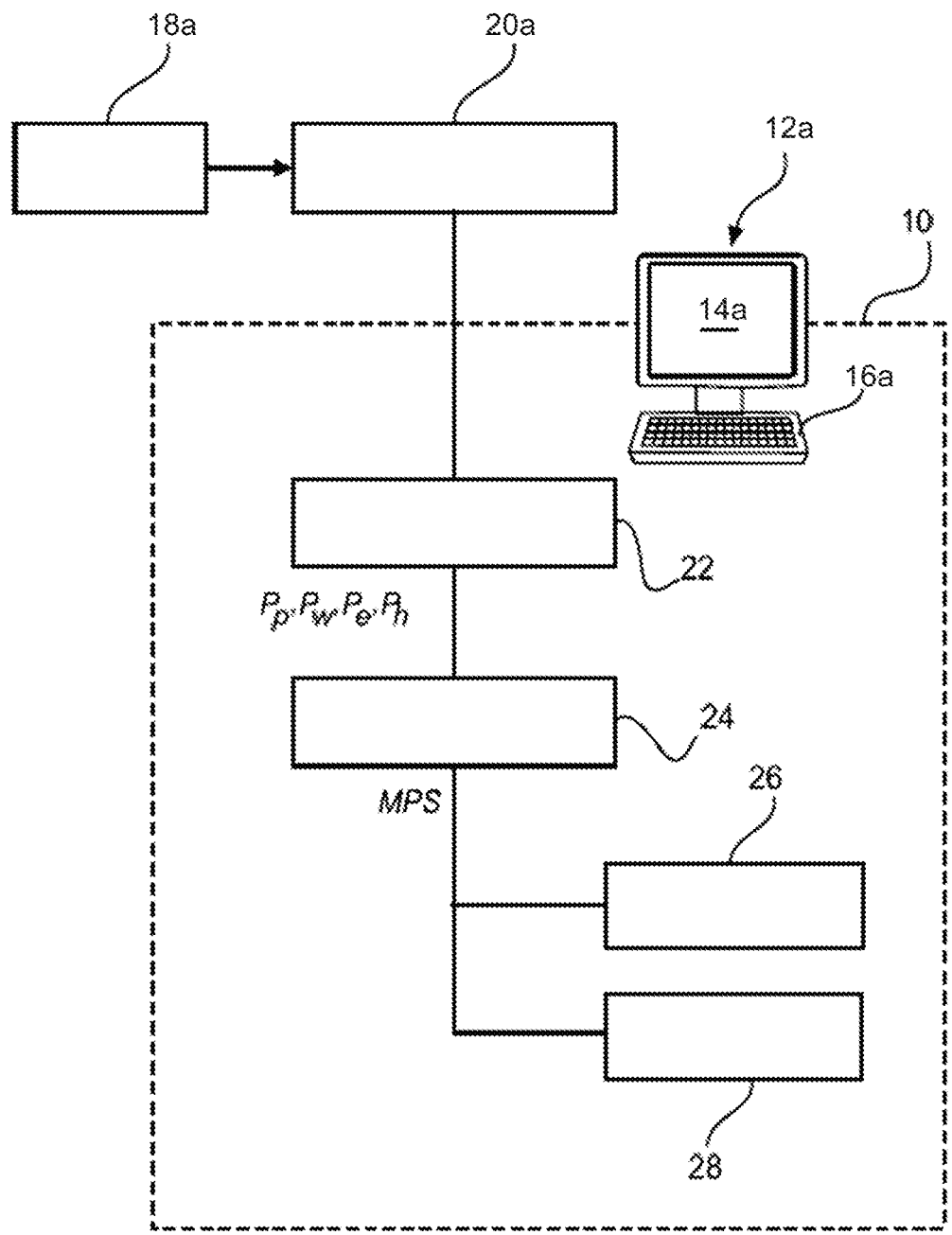
FIG. 11 diagrammatically shows a clinical decision support (CDS) system configured to determine a risk score that indicates a risk that a subject will experience a clinical event within a certain period of time, as disclosed herein.

One advantage resides in a clinical decision support (CDS) system as illustrated in FIG. 11, described in more detail in Example 3 below, that is adapted to provide clinical recommendations, e.g., by deciding a treatment for a subject, based on an analysis of two or more cellular signaling pathways, for example, using a probabilistic or another mathematical model of the PI3K pathway, the Wnt pathway, the ER pathway, and the HH pathway, in particular, based on a risk that the subject will experience a clinical event, e.g., cancer, in particular, breast cancer, within a certain period of time, as indicated by a risk score that is based at least in part on a combination of inferred activities of the cellular signaling pathways.

Another advantage resides in a CDS system that is adapted to assign a subject to at least one of a plurality of risk groups associated with different risks that the subject will experience a clinical event, e.g., cancer, in particular, breast cancer, within a certain period of time, as indicated by a risk score that is based at least in part on a combination of inferred activities of two or more cellular signaling pathways.

Another advantage resides in combining a risk score that indicates a risk that a subject will experience a clinical event within a certain period of time and that is based at least in part on a combination of inferred activities of two or more cellular signaling pathways with one or more additional risk scores obtained from one or more additional prognostic tests.

Diseases, Disorders, and Methods of Treatment

As contemplated herein, the methods and apparatuses of the present disclosure can be utilized to assess PI3K, Wnt, ER, and/or HH cellular signaling pathway activity in a subject, for example a subject suspected of having, or having, a disease or disorder wherein the status of one of the signaling pathways is probative, either wholly or partially, of disease presence or progression. In one embodiment, provided herein is a method of treating a subject comprising receiving information regarding the activity status of a PI3K, Wnt, ER, and/or HH cellular signaling pathways derived from a sample isolated from the subject using the methods described herein and administering to the subject an inhibitor of PI3K, Wnt, ER, and/or HH if the information regarding the level of the cellular signaling pathways is indicative of an active PI3K, Wnt, ER, and/or HH signaling pathway.

PI3K inhibitors that may be used in the present disclosure are well known. Examples of PI3K include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2, 4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate: or Methyl(oxo) {[(2R)-1-phenoxy-2-butanyl] oxy}phosphonium)), BYL-719 ((2S)-N1-[4-Methyl-5-[2-(2, 2,2-trifluoro-1,1-dimethylethyl)-4-pyridinyl]-2-thiazolyl]-1, 2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S])-1-[9H-purin-6-ylamino]-propyl)-3H-quinazolin-4-one), AMG-319, GSK-2269557, SAR245409 (N-(4-(N-(3-((3,5-dimethoxyphenyl) amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide). Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-I-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N'-[4-(4, 6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4, 5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidinedione), PX886 ([(3aR,6E, 9S,9aR,10R,11aS)-6-[[bis(prop-2-enyl)amino] methylidene]-5-hydroxy-9-(methoxymethyl)-9a,11a-dimethyl-1,4,7-trioxo-2,3,3a,9,10,]]-hexahydroindeno[4,5h] isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-1 15, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structures described in WO2014/071109. Alternatively, inhibitors of the mTOR complex downstream of PI3K are valuable inhibitors of aberrant PI3K activity. Examples of mTOR inhibitors include but are not limited to everolimus, temsirolimus, ridaforolimus. Alternatively, inhibitors of the HER2 complex upstream of PI3K are valuable inhibitors of aberrant PI3K activity. Examples of HER2 inhibitors include but are not limited to trastuzumab, lapatinib, pertuzmab.

Endocrine therapy can be administered in breast cancers that are estrogen receptor positive. Endocrine therapy treatments that may be used in the present disclosure are well known. Endocrine therapy consists of administration of i) ovarian function suppressors, usually obtained using gonadotropin-releasing hormone agonists (GnRHa), ii) selective estrogen receptor modulators or down-regulators (SERMs or SARDs), or iii) aromatase inhibitors (AIs), or a combination thereof. Ovarian function suppressors include, for example, gonadotropin-releasing hormone agonists (GnRHa). Examples of gonadotropin-releasing hormone agonists (GnRHa) can include buserelin, deslorelin, gonadorelin, goserelin, histrelin, leuprorelin, nafarelin, and triptorelin. Selective estrogen receptor modulators (SERMs) include, for example, tamoxifen, toremifene, raloxifene, lasofoxifene, bazedoxifene, clomifene, ormeloxifene, ospemifene, afimoxifene, and arzoxifene. Selective estrogen receptor down-regulators (SERDs) include, for example, fulvestrant. SR16234, and ZK191703. Aromatase inhibitors include, for example, anastrozole, letrozole, vorozole, exemestane, aminoglutethimide, testolactone, formestane, fadrozole, androstenedione, 4-hydroxyandrostenedione, 1,4, 6-androstatrien-3,17-dione, or 4-androstene-3,6,17-trione. In one embodiment, the aromatase inhibitor is a non-steroidal aromatase inhibitor.

Wnt inhibitors are well known and include, but are not limited to, pyrvinium, IWR-1-endo, IWP-2, FH535, WIKI4, IWP-L6, KY02111, LGK-974, Wnt-C59, XAV929, 3289-8625, FJ9, NSC 668036, PFK115-584, CGP049090, iCRT3, iCRT5, iCRT14, ICG-001, demethoxy curcumin, CCT036477, KY02111, PNU-74654, or PRI-724.

HH inhibitors are well known and include, but are not limited to, cyclopiamine, SANT1-SANT4, CUR-61414, HhAntag-691, GDC-0449, MK4101, IPI-926, BMS-833923, robotnikinin, itraconazole, Erivedge, Odomzo, Calcitriol, Cholecalciferol, IPI-906, RU-SKI 39, or KAAD-cyclopamine. NVP-LDE225, TAK-441, XL-139, LY2940680, NVP-LEQ506, Itraconazole, MRT-10, MRT 83, PF-04449913, GANT-61, GANT-58, HPI-1, HPI-3, or HPI-4.

In one embodiment, the cellular signaling pathways comprise at least one cellular signaling pathway that plays a role in cancer.

In one embodiment, the disease or disorder is one of an auto-immune and other immune disorders, cancer, bronchial asthma, heart disease, diabetes, hereditary hemorrhagic telangiectasia. Marfan syndrome, Vascular Ehlers-Danlos syndrome, Loeys-Dietz syndrome, Parkinson's disease, Chronic kidney disease, Multiple Sclerosis, fibrotic diseases such as liver, lung, or kidney fibrosis, Dupuytren's disease, or Alzheimer's disease.

In a particular embodiment, the subject is suffering from, or suspected to have, a cancer, for example, but not limited to, a primary tumor or a metastatic tumor, a solid tumor, for example, melanoma, lung cancer (including lung adenocarcinoma, basal cell carcinoma, squamous cell carcinoma, large cell carcinoma, bronchioloalveolar carcinoma, bronchiogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma): anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer: bladder carcinoma; carcinoma of the uterus (including endometrial adenocarcinoma, ocular, uterine papillary serous carcinoma, uterine clear-cell carcinoma, uterine sarcomas and leiomyosarcomas, mixed mullerian tumors); glioma, glioblastoma, medulloblastoma, and other tumors of the brain: kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor): testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, libromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma. Islet cell carcinoma, malignant carcinoid, malignant paraganglioma, melanoma, Merkel cell neoplasm, cystosarcoma phylloide, salivary cancers, thymic carcinomas, and cancers of the vagina among others.

In one embodiment, the methods described herein are useful for treating a host suffering from a lymphoma or lymphocytic or myelocytic proliferation disorder or abnormality. For example, the subject suffering from a Hodgkin Lymphoma of a Non-Hodgkin Lymphoma. For example, the subject can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma: Burkitt's Lymphoma; Burkitt-like Lymphoma (Small Non-Cleaved Cell Lymphoma): Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma: Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the subject may be suffering from a Hodgkin Lymphoma, such as, but not limited to: Nodular Sclerosis Classical Hodgkin's Lymphoma (CHL); Mixed Cellularity CHL: Lymphocyte-depletion CHL; Lymphocyte-rich CHL; Lymphocyte Predominant Hodgkin Lymphoma; or Nodular Lymphocyte Predominant HL.

In one embodiment, the subject may be suffering from a specific T-cell, a B-cell, or a NK-cell based lymphoma, proliferative disorder, or abnormality. For example, the subject can be suffering from a specific T-cell or NK-cell lymphoma, for example, but not limited to: Peripheral T-cell lymphoma, for example, peripheral T-cell lymphoma and peripheral T-cell lymphoma not otherwise specified (PTCL-NOS); anaplastic large cell lymphoma, for example anaplastic lymphoma kinase (ALK) positive. ALK negative anaplastic large cell lymphoma, or primary cutaneous anaplastic large cell lymphoma; angioimmunoblastic lymphoma; cutaneous T-cell lymphoma, for example mycosis fungoides, Sdzary syndrome, primary cutaneous anaplastic large cell lymphoma, primary cutaneous CD30+ T-cell lymphoproliferative disorder: primary cutaneous aggressive epidermotropic CD8+ cytotoxic T-cell lymphoma: primary cutaneous gamma-delta T-cell lymphoma; primary cutaneous small/medium CD4+ T-cell lymphoma, and lymphomatoid papulosis: Adult T-cell Leukemia/Lymphoma (ATLL): Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia: T-cell large granular lymphocytic leukemia; Chronic lymphoproliferative disorder of NK-cells: Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

Alternatively, the subject may be suffering from a specific B-cell lymphoma or proliferative disorder such as, but not limited to: multiple myeloma: Diffuse large B cell lymphoma; Follicular lymphoma: Mucosa-Associated Lymphatic Tissue lymphoma (MALT); Small cell lymphocytic lymphoma; Mantle cell lymphoma (MCL); Burkitt lymphoma: Mediastinal large B cell lymphoma; Waldenstrom macroglobulinemia; Nodal marginal zone B cell lymphoma (NMZL); Splenic marginal zone lymphoma (SMZL); Intravascular large B-cell lymphoma; Primary effusion lymphoma; or Lymphomatoid granulomatosis: Chronic lymphocytic leukemia/small lymphocytic lymphoma; B-cell prolymphocytic leukemia: Hairy cell leukemia: Splenic lymphoma/leukemia, unclassifiable; Splenic diffuse red pulp small B-cell lymphoma: Hairy cell leukemia-variant; Lymphoplasmacytic lymphoma: Heavy chain diseases, for example, Alpha heavy chain disease, Gamma heavy chain disease, Mu heavy chain disease; Plasma cell myeloma; Solitary plasmacytoma of bone; Extraosseous plasmacytoma: Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma: Large B-cell lymphoma arising in HHV8-associated multicentric: Castleman disease; B-cell lymphoma, unclassifiable, with features intermediate between diffuse large B-cell lymphoma and Burkitt lymphoma; B-cell lymphoma, unclassifiable, with features intermediate between diffuse large B-cell lymphoma and classical Hodgkin lymphoma; Nodular sclerosis classical Hodgkin lymphoma; Lymphocyte-rich classical Hodgkin lymphoma; Mixed cellularity classical Hodgkin lymphoma; or Lymphocyte-depleted classical Hodgkin lymphoma.

In one embodiment, the subject is suffering from a leukemia For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL): Chronic myelogenous leukemia (CML): juvenile myelomonocytic leukemia (JMML); hairy cell leukemia (HCL): acute promyelocytic leukemia (a subtype of AML); T-cell prolymphocytic leukemia (TPLL); large granular lymphocytic leukemia: or Adult T-cell chronic leukemia; large granular lymphocytic leukemia (LGL). In one embodiment, the patient suffers from an acute myelogenous leukemia, for example an undifferentiated AML (M0): myeloblastic leukemia (M1; with/without minimal cell maturation): myeloblastic leukemia (M2: with cell maturation); promyelocytic leukemia (M3 or M3 variant [M3V]); myelomonocytic leukemia (M4 or M4 variant with eosinophilia [M4E]); monocytic leukemia (M5): erythroleukemia (M6); or megakaryoblastic leukemia (M7).

In a particular embodiment, the subject is suffering, or suspected to be suffering from, a breast cancer, lung cancer, a colon cancer, pancreatic cancer, or brain cancer. In a particular embodiment, the subject is suffering from, or suspected to be suffering from, a breast cancer.

In the particular embodiment of cancer, patients at high risk of experiencing the clinical event may receive chemotherapy or targeted therapy in addition to standard of care treatment modalities such as, but not limited to, surgery, radiotherapy, (targeted) drug therapy. Alternatively, patients at low risk of experiencing the clinical event may refrain from standard of care modalities such as, but not limited to, surgery, radiotherapy, chemotherapy.

In one embodiment, the determination of whether to administer a therapeutic, or refrain from administering a therapeutic, can be based on a threshold MPS score, for example a threshold established for assigning a patient to a low risk group or a threshold established for assigning a patient to a high risk group. For example, in one embodiment, the threshold for assigning patients to the low risk group may be based on the risk of the clinical event at 5, 6, 7, 8, 9, 10, or more years being smaller than or equal 5%, 10%, 15%, 20%, whereas the threshold for assigning patients to the high risk group may be based on the risk of the clinical event at 5, 6, 7, 8, 9, 10, or more years being larger or equal to 20%, 25%, 30%, 35%, 40%, 45%, 50%, or greater. For example, using the illustration above, in the particular case of MPStpweh this results in a threshold for the low risk patient group being −0.5, −0.4, −0.3, −0.2, −0.1, 0 and the threshold for the high risk patient group being 0, 0.1, 0.2, 0.3, 0.4, 0.5, 0.6, 0.7, 0.8, 0.9, 1, 1.1, 1.2.

In one aspect of the present disclosure, the clinical event for which a subject may be assigned into a low risk or high risk group may include a cancer recurrence, progression, metastasis, death due to cancer, or a clinical event as described elsewhere herein.

In the particular embodiment, the assignment of a high risk or low risk is for a subject with breast cancer, patients with a ER+ or HR+ tumor or luminal A or luminal B subtype and at high risk of experiencing the clinical event may receive (neo)adjuvant chemotherapy in addition to hormone treatment such as, but not limited to, tamoxifen or aromatase inhibitors. ER+ tumor or luminal A or luminal B subtype and at low risk of experiencing the clinical event may receive (neo)adjuvant hormone treatment (and refrain from chemotherapy). Patients with a HER2+/HR− tumor or HER2 enriched subtype and at high risk of experiencing the clinical event may receive (neo)adjuvant chemotherapy in addition to anti-HER2 treatment such as, but not limited to, trastuz.umab, whereas HER2+/HR− tumor or HER2 enriched subtype and at low risk of experiencing the clinical event may receive (neo)adjuvant anti-HER2 treatment (and refrain from chemotherapy). Patients with a HER2+/HR+ tumor and at a high risk of experiencing the clinical event may receive (neo)adjuvant chemotherapy with anti-HER2 treatment in addition to hormone treatment such as, but not limited to, tamoxifen or aromatase inhibitors, whereas patients with a HER2+/HR+ tumor and a low risk of experiencing the clinical event may receive (neo)adjuvant hormone treatment (and refrain from chemotherapy and/or anti-HER2 treatment). Patients with a triple negative (HER2−/ER−/PR− or HER2−/HR−) tumor or basal subtype and at a high risk of experiencing the clinical event may receive (neo)adjuvant chemotherapy in addition to targeted therapy such as, but not limited to, described herein, whereas patients with a triple negative tumor or basal subtype and a low risk of experiencing the clinical event may receive (neo)adjuvant targeted therapy (and refrain from chemotherapy).

The sample(s) to be used in accordance with the present disclosure can be an extracted sample, that is, a sample that has been extracted from the subject. Examples of the sample include, but are not limited to, a tissue, cells, blood and/or a body fluid of a subject. It can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, a body fluid of which a sample is extracted may be urine, gastrointestinal contents, or an extravasate.

In one embodiment, provided herein is a method that further comprises combining the risk score and/or at least one of the inferred activities with one or more additional risk scores obtained from one or more additional prognostic tests to obtain a combined risk score, wherein the combined risk score indicates a risk that the subject will experience the clinical event within the certain period of time. The one or more additional prognostic tests may comprise, in particular, the Oncotype DX® breast cancer test, the Mammostrat® breast cancer test, the MammaPrint® breast cancer test, the EndoPredict® breast cancer test, the BluePrint™ breast cancer test, the CompanDx®, breast cancer test, the Breast Cancer Index$^{SM}$ (HOXB13/IL17BR), the OncotypeDX® colon cancer test, and/or a proliferation test performed by measuring expression of gene/protein Ki67.

In one embodiment, the clinical event is one of recurrence of cancer, progression of cancer, occurrence of cancer, and death caused by cancer, wherein, in particular, the cancer is breast cancer. The risk that the clinical event will occur within the certain period of time is then preferentially the risk of recurrence, i.e., the return, of cancer, either after a given treatment (also called "cancer therapy response prediction") or without any treatment (also called "cancer prognosis"). The recurrence can be either local (i.e., at the side of the original tumor), or distant (i.e., metastasis, beyond the original side). In other alternatives, the risk that the clinical event will occur within the certain period of time is the risk of progression of cancer, the risk of occurrence of cancer, or the risk of death caused by cancer. In one embodiment, the clinical event is death. In one embodiment, the clinical event is disease recurrence. In one embodiment, the clinical event is disease progression. In one embodiment, the clinical event is death. In one embodiment, the clinical event is survival.

In one embodiment, the risk monotonically increases with an increasing activity level of the PI3K cellular signaling pathway, the Wnt cellular signaling pathway, and the HH cellular signaling pathway in the sample, and monotonically decreases with an increasing activity level of the ER cellular signaling pathway in the sample.

Another aspect of the present disclosure relates to a method (as described herein), further comprising:

assigning the subject to at least one of a plurality of risk groups associated with different indicated risks that the subject will experience the clinical event within the certain period of time, and/or deciding a treatment recommended for the subject based at least in part on the indicated risk that the subject will experience the clinical event within the certain period of time.

The present disclosure also relates to a method (as described herein), comprising:

calculating the activity of the PI3K pathway in the subject based at least on expression levels of two, three or more target genes of a set of target genes of the PI3K pathway measured in the sample of the subject, and/or calculating the activity of the Wnt pathway in the subject based at least on expression levels of two, three or more target genes of a set of target genes of the Wnt pathway measured in the sample of the subject, and/or calculating the activity of the ER pathway in the subject based at least on expression levels of two, three or more target genes of a set of target genes of the ER pathway measured in the sample of the subject, and/or calculating the activity of the HH pathway in the subject based at least on expression levels of two, three or more target genes of a set of target genes of the HH pathway measured in the sample of the subject.

In one embodiment, the set of target genes of the PI3K pathway includes at least nine, or in an alternative, all target genes selected from the group consisting of: AGRP, BCL2L11, BCL6. BNIP3, BTG1, CAT, CAV1, CCND1, CCND2, CCNG2, CDKN1A, CDKN1B, ESR1, FASLG, FBXO32, GADD45A, INSR, MXI1, NOS3, PCK1, POMC, PPARGC1A, PRDX3, RBL2, SOD2, and TNFSF10, and/or the set of target genes of the Wnt pathway includes at least nine, or in an alternative, all target genes selected from the group consisting of: KIAA1199 (CEMIP), AXIN2, CD44, RNF43, MYC, TBX3, TDGF1, SOX9, ASCL2, IL8 (CXCL8). SP5, ZNRF3, EPHB2, LGR5, EPHB3, KLF6, CCND1, DEFA6, and FZD7, and/or the set of target genes of the ER pathway includes at least nine, or in an alternative, all target genes selected from the group consisting of: GREB1, PGR, XBP1, CA12, SOD1, CTSD, IGFBP4, TFF1, SGK3, NRIP1, CELSR2, WISP2, and AP1B1, and/or the set of target genes of the HH pathway includes at least nine, or in an alternative, all target genes selected from the group consisting of: GLI1, PTCH1, PTCH2, IGFBP6, SPP1, CCND2, FST, FOXL1, CFLAR, TSC22D1, RAB34, S100A9, S100A7, MYCN, FOXM1, GLI3. TCEA2, FYN, and CTSL1.

In one embodiment, provided herein is a method wherein the set of target genes of the PI3K pathway further includes:

(i) at least one target gene selected from the group consisting of: ATP8A1, C10orf10, CBLB, DDB1, DYRK2, ERBB3, EREG, EXT1, FGFR2, IGF1R, IGFBP1, IGFBP3, LGMN, PPM1D, SEMA3C, SEPP1, SESN1, SLC5A3, SMAD4, and TLE4, and/or (ii) at least one target gene selected from the group consisting of: ATG14, BIRC5, IGFBP1, KLF2, KLF4, MYOD1, PDK4, RAG1, RAG2, SESN1, SIRT1, STK11 and TXNIP, and/or the set of target genes of the Wnt pathway further includes at least one target gene selected from the group consisting of: NKD1, OAT, FAT1, LEF1, GLUL, REG1B, TCF7L2, COL18A1, BMP7. SLC1A2, ADRA2C, PPARG, DKK1, HNF1A, and LECT2, and/or the set of target genes of the ER pathway further includes at least one target gene selected from the group consisting of: RARA, MYC, DSCAM, EBAG9, COX7A2L, ERBB2, PISD, KRT19, HSPB1, TRIM25, PTMA, COL18A1, CDH26, NDUFV3, PRDM15, ATP5J, and ESR1, and/or the set of target genes of the HH pathway further includes at least one target gene selected from the group consisting of: BCL2, FOXA2, FOXF1, H19, HHIP, IL1R2, JAG2, JUP, MIF, MYLK, NKX2.2, NKX2.8, PITRM1, and TOM1.

If the set of target genes of the PI3K pathway further includes both at least one target gene of the PI3K pathway selected from the group (i) and at least one target gene of the PI3K pathway selected from the group (ii), the target genes IGFBP1 and SESN1, which are mentioned above with respect to both groups, may only be contained in one of the groups.

The present disclosure as described herein can, e.g., also advantageously be used in connection with prognosis and/or prediction based at least in part on a combination of inferred activities of two or more cellular signaling pathways, and/or prediction of drug efficacy of e.g. chemotherapy and/or hormone treatment and/or targeted treatment such as, but not limited to, trastuzumab, everolimus, lapatinib and/or pertuzumab based at least in part on a combination of inferred activities of two or more cellular signaling pathways, and/or monitoring of drug efficacy based at least in part on a combination of inferred activities of two or more cellular signaling pathways, and/or deciding on the frequency of monitoring or more particularly on the frequency of therapy response monitoring, and/or drug development based at least in part on a combination of inferred activities of two or more cellular signaling pathways, and/or assay development based at least in part on a combination of inferred activities of two or more cellular signaling pathways, and/or cancer staging based at least in part on a combination of inferred activities of two or more cellular signaling pathways.

wherein in each case, the cellular signaling pathways comprise a PI3K pathway and one or more of a Wnt pathway, an ER pathway, and an HH pathway.

Further advantages will be apparent to those of ordinary skill in the art upon reading and understanding the attached figures, the following description and, in particular, upon reading the detailed examples provided herein below.

EXAMPLES

The following examples merely illustrate exemplary methods and selected aspects in connection therewith. The teaching provided therein may be used for constructing several tests and/or kits, e.g., to detect, predict and/or diagnose the abnormal activity of the PI3K pathway and one or more of a Wnt pathway, an ER pathway, and an HH pathway and a risk score based thereon. These tests and/or kits can identify a subject at risk of experiencing a clinical event associated with a disease within a defined period of time. Furthermore, upon using methods as described herein drug prescription can advantageously be guided, drug response prediction and monitoring of drug efficacy (and/or adverse effects) can be made, and drug resistance can be predicted and monitored, e.g., to select subsequent test(s) to be performed (like a companion diagnostic test). The following examples are not to be construed as limiting the scope of the present disclosure.

Example 1: Calculating Activity of Two or More Cellular Signaling Pathways

As described in detail in the published international patent application WO 2013/011479 A2 ("Assessment of cellular signaling pathway activity using probabilistic modeling of target gene expression"), by constructing a probabilistic model, e.g., a Bayesian model, and incorporating conditional probabilistic relationships between expression levels of a number of different target genes and the activity of the cellular signaling pathway, such a model can be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

When using this approach, the target genes of the Wnt pathway, the ER pathway, and the HH pathway are selected according to the methods described in "Example 3: Selection of target genes" of WO 2013/011479 A2 and the probabilistic model can be trained according to the methods described in "Example 5: Training and using the Bayesian network" of WO 2013/011479 A2. A suitable choice of the target gene(s) that are used for determining the activity of the Wnt pathway, the ER pathway, and the AR pathway is defined in the appended claims.

In another easy to comprehend and interpret approach described in detail in the published international patent application WO 2014/102668 A2 ("Assessment of cellular signaling pathway activity using linear combination(s) of target gene expressions"), the activity of a certain cellular signaling pathway is determined by constructing a mathematical model (e.g., a linear or (pseudo-)linear model) incorporating relationships between expression levels of one or more target gene(s) of a cellular signaling pathway and the level of a transcription factor (TF) element, the TF element controlling transcription of the one or more target gene(s) of the cellular signaling pathway, the model being based at least in part on one or more linear combination(s) of expression levels of the one or more target gene(s).

When using this approach, the target genes of the Wnt pathway, the ER pathway, and the HH pathway are selected according to the methods described in sections "Example 2: Selection of target genes" and "Example 3: Comparison of evidence curated list and broad literature list" of WO 2014/102668 A2 and the mathematical model can be trained according to the methods described in "Example 4: Training and using the mathematical model" of WO 2014/102668 A2. The choice of the target gene(s) defined in the appended claims is also useful for determining the activity of the Wnt pathway, the ER pathway, and the HH pathway with this later approach.

With respect to the two different approaches, the expression levels of the one or more target gene(s) may, for example, be measurements of the level of mRNA, which can be the result of, e.g., (RT)-PCR and microarray techniques using probes associated with the target gene(s) mRNA sequences, and of RNA-sequencing. In another embodiment the expression levels of the one or more target gene(s) can be measured by protein levels, e.g., the concentrations of the proteins encoded by the target genes.

The aforementioned expression levels may optionally be converted in many ways that might or might not suit the application better. For example, four different transformations of the expression levels, e.g., microarray-based mRNA levels, may be:

"continuous data", i.e., expression levels as obtained after preprocessing of microarrays using well known algorithms such as MAS5.0 and fRMA, "z-score", i.e., continuous expression levels scaled such that the average across all samples is 0 and the standard deviation is 1, "discrete", i.e., every expression above a certain threshold is set to 1 and below it to 0 (e.g., the threshold for a probeset may be chosen as the median of its value in a set of a number of positive and the same number of negative clinical samples).

"fuzzy", i.e., the continuous expression levels are converted to values between 0 and 1 using a sigmoid function of the following format: $1/(1+\exp((thr-expr)/se))$, with expr being the continuous expression levels, thr being the threshold as mentioned before and se being a softening parameter influencing the difference between 0 and 1.

One of the simplest models that can be constructed is a model having a node representing the transcription factor (TF) element in a first layer and weighted nodes representing direct measurements of the target gene(s) expression intensity levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probe with the lowest p-value is by definition the probe with the least likely probability that the expression levels of the (known) active and passive samples overlap. Another selection method is based on odds-ratios. In such a model, one or more expression level(s) are provided for each of the one or more target gene(s) and the one or more linear combination(s) comprise a linear combination including for each of the one or more target gene(s) a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the one or more target gene(s) and the one or more linear combination(s) comprise a linear combination of all expression levels of the one or more expression level(s) provided for the one or more target gene(s). In other words, for each of the one or more target gene(s), each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels.

After the level of the TF element has been determined by evaluating the respective model, the determined TF element level can be thresholded in order to infer the activity of the cellular signaling pathway. A method to calculate such an appropriate threshold is by comparing the determined TF element level wlc of training samples known to have a passive pathway and training samples with an active pathway. A method that does so and also takes into account the variance in these groups is given by using a threshold $$thr = \frac{\sigma_{wlc_{pas}} \mu_{wlc_{act}} + \sigma_{wlc_{act}} \mu_{wlc_{pas}}}{\sigma_{wlc_{pas}} + \sigma_{wlc_{act}}} \quad (1)$$

where $\sigma$ and $\mu$ are the standard deviation and the mean of the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\,\tilde{v} + (n_{act} - 1)v_{wlc_{act}}}{x + n_{act} - 1}$$

$$\tilde{v}_{wlc_{pas}} = \frac{x\,\tilde{v} + (n_{pas} - 1)v_{wlc_{pas}}}{x + n_{pas} - 1}$$

where v is the variance of the determined TF element levels wlc of the groups, x is a positive pseudocount, e.g., 1 or 10, and nact and npas are the number of active and passive samples, respectively. The standard deviation $\sigma$ can next be obtained by taking the square root of the variance v.

The threshold can be subtracted from the determined level of the TF element wlc for ease of interpretation, resulting in the cellular signaling pathway's activity score, such that negative values corresponds to a passive cellular signaling pathway and positive values to an active cellular signaling pathway.

As an alternative to the described "single-layer" models, a "two-layer" model representing the experimental determination of active signaling of a pathway can be used. For every target gene a summary level is calculated using a linear combination based on the measured intensities of its associated probesets ("first (bottom) layer"). The calculated summary value is subsequently combined with the summary values of the other target genes of the pathway using a further linear combination ("second (upper) layer"). The weights can be either learned from a training data set or based on expert knowledge or a combination thereof. Phrased differently, in the "two-layer" model, one or more expression level(s) are provided for each of the one or more target gene(s) and the one or more linear combination(s) comprise for each of the one or more target gene(s) a first linear combination of all expression levels of the one or more expression level(s) provided for the respective target gene ("first (bottom) layer"). The model is further based at least in part on a further linear combination including for each of the one or more target gene(s) a weighted term, each weighted term being based on the first linear combination for the respective target gene ("second (upper) layer").

The calculation of the summary values can, in an exemplary version of the "two-layer" model, include defining a threshold for each target gene using the training data and subtracting the threshold from the calculated linear combination, yielding the gene summary. Here, the threshold may be chosen such that a negative gene summary level corresponds with a downregulated target gene and that a positive gene summary level corresponds with an upregulated target gene. Also, it is possible that the gene summary values are transformed using e.g. one of the above-mentioned transformations (fuzzy, discrete, etc.) before they are combined in the "second (upper) layer".

After the level of the TF element has been determined by evaluating the "two-layer" model, the determined TF element level can be thresholded in order to infer the activity of the cellular signaling pathway, as described above.

Herein, the models described above with reference to WO 2014/102668 A2 are collectively denoted as "(pseudo-) linear models".

While the above description regarding the mathematical model construction also applies to the inferring of the activity of the PI3K pathway, the selection of the target genes and the training and use of the mathematical model was modified to some extend for the PI3K pathway compared to the Wnt pathway, the ER pathway, and the HH pathway. These steps will therefore be described for the PI3K pathway in more detail in the following:

(A) PI3K Pathway (i) Selection of target genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the transcription complex is herein referred to as a "direct target gene" (of the transcription factor). Cellular signaling pathway activation may also result in more secondary gene transcription, referred to as "indirect target genes". In the following, Bayesian network models (as exemplary mathematical models) comprising or consisting of direct target genes as direct links between cellular signaling pathway activity and mRNA level, are exemplified, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, two repositories of currently available scientific literature were employed to generate two lists of target genes.

The first list of target genes was generated based on scientific literature retrieved from the MEDLINE database of the National Institute of Health accessible at "ncbi.nlm.nih.gov/pubmed" and herein further referred to as "Pubmed". Publications containing putative FOXO target genes were searched for by using queries such as (FOXO AND "target gene") in the period of the first quarter of 2013. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a target gene, like for example an mRNA increasing on an microarray of an cell line in which it is known that the PI3K cellular signaling axis is active, other evidence can be very strong, like the combination of an identified cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a cellular signaling pathway-TF to its binding site on the genome is shown. Example: By using chromatin immunoprecipitation (ChIP) technology subsequently putative functional FOXO TF binding sites in the DNA of cell lines with and without active induction of the PI3K pathway were identified, as a subset of the binding sites recognized purely based on nucleotide sequence. Putative functionality was identified as ChIP-derived evidence that the TF was found to bind to the DNA binding site.

2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.

3. Stimulation of the cellular signaling pathway and measuring mRNA profiles on a microarray or using RNA sequencing, using cellular signaling pathway-inducible cell lines and measuring mRNA profiles measured several time points after induction—in the presence of cycloheximide, which inhibits translation to protein, thus the induced mRNAs are assumed to be direct target genes.

4. Similar to 3, but using quantitative PCR to measure the amounts of mRNAs.

5. Identification of TF binding sites in the genome using a bioinformatics approach. Example for the FOXO TF element: Using the conserved FOXO binding motif 5'-TTGTTTAC-3', a software program was run on the human genome sequence, and potential binding sites were identified, both in gene promoter regions and in other genomic regions.

6. Similar as 3, only in the absence of cycloheximide.

7. Similar to 4, only in the absence of cycloheximide.

8. mRNA expression profiling of specific tissue or cell samples of which it is known that the cellular signaling pathway is active, however in absence of the proper negative control condition.

In the simplest form one can give every potential target mRNA 1 point for each of these experimental approaches in which the target mRNA was identified.

Alternatively, points can be given incrementally, meaning one technology one point, a second technology adds a second point, and so on. Using this relatively simple ranking strategy, one can make a list of most reliable target genes.

Alternatively, ranking in another way can be used to identify the target genes that are most likely to be direct target genes, by giving a higher number of points to the technology that provides most evidence for an in vivo direct target gene, in the list above this would mean 8 points for experimental approach 1), 7 for 2), and going down to 1 point for experimental approach 8). Such a list may be called a "general target gene list".

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the PI3K pathway that can be applied to samples coming from different tissue sources.

The following will illustrate exemplary how the selection of an evidence curated target gene list specifically was constructed for the PI3K pathway.

For the purpose of selecting PI3K target genes used as input for the "model", the following three criteria were used:

1. Gene promoter/enhancer region contains a FOXO binding motif:
  a. The FOXO binding motif should be proven to respond to an activity of the PI3K pathway, e.g., by means of a transient transfection assay in which the specific FOXO motif is linked to a reporter gene, and
  b. The presence of the FOXO motif should be confirmed by, e.g., an enriched motif analysis of the gene promoter/enhancer region.

2. FOXO (differentially) binds in vivo to the promoter/enhancer region of the gene in question, demonstrated by, e.g., a ChIP/CHIP experiment or another chromatin immunoprecipitation technique:
- a. FOXO is proven to bind to the promoter/enhancer region of the gene when the PI3K pathway is not active, and
- b. (preferably) does not bind (or weakly binds) to the gene promoter/enhancer region of the gene when the PI3K pathway is active.
3. The gene is differentially transcribed when the activity of the PI3K pathway is changed, demonstrated by, e.g.,
- a. fold enrichment of the mRNA of the gene in question through real time PCR, or microarray experiment, or
- b. the demonstration that RNA Pol II binds to the promoter region of the gene through an immunoprecipitation assay.

The selection was performed by defining as target genes of the PI3K pathway the genes for which enough and well documented experimental evidence was gathered proving that all three criteria mentioned above were met. A suitable experiment for collecting evidence of PI3K differential binding is to compare the results of, e.g., a ChIP-Seq experiment in a cancer cell line that expresses activity of the PI3K pathway in response to tamoxifen (e.g., a cell line transfected with a tamoxifen-inducible FOXO construct, such as FOXO.A3.ER), when exposed or not exposed to tamoxifen. The same holds for collecting evidence of mRNA transcription.

The foregoing discusses the generic approach and a more specific example of the target gene selection procedure that has been employed to select a number of target genes based upon the evidence found using the above mentioned approach. The lists of target genes used in the Bayesian network models for the PI3K pathway is shown in Table 1.

TABLE 1

"Evidence curated list of target genes" of the PI3K pathway used in the PI3K pathway models and associated probesets used to measure the mRNA expression level of the target genes.

| Target gene | Probeset |
|---|---|
| ATP8A1 | 1569773_at |
|  | 210192_at |
|  | 213106_at |
| BCL2L11 | 1553088_a_at |
|  | 1553096_s_at |
|  | 1555372_at |
|  | 1558143_a_at |
|  | 208536_s_at |
|  | 222343_at |
|  | 225606_at |
| BNIP3 | 201848_s_at |
|  | 201849_at |
| BTG1 | 1559975_at |
|  | 200920_s_at |
|  | 200921_s_at |
| C10orf10 | 209182_s_at |
|  | 209183_s_at |
| CAT | 201432_at |
|  | 211922_s_at |
|  | 215573_at |
| CBLB | 208348_s_at |
|  | 209682_at |
| CCND1 | 208711_s_at |
|  | 208712_at |
|  | 214019_at |
| CCND2 | 200951_s_at |
|  | 200952_s_at |
|  | 200953_s_at |
|  | 231259_s_at |
|  | 1555056_at |
|  | 202769_at |
|  | 202770_s_at |
|  | 211559_s_at |

TABLE 1-continued

"Evidence curated list of target genes" of the PI3K pathway used in the PI3K pathway models and associated probesets used to measure the mRNA expression level of the target genes.

| Target gene | Probeset |
|---|---|
| CDKN1B | 209112_at |
| DDB1 | 208619_at |
| DYRK2 | 202968_s_at |
|  | 202969_at |
|  | 202970_at |
|  | 202971_s_at |
| ERBB3 | 1563252_at |
|  | 1563253_s_at |
|  | 202454_s_at |
|  | 215638_at |
|  | 226213_at |
| EREG | 1569583_at |
|  | 205767_at |
| ESR1 | 205225_at |
|  | 211233_x_at |
|  | 211234_x_at |
|  | 211235_s_at |
|  | 211627_x_at |
|  | 215551_at |
|  | 215552_s_at |
|  | 217190_x_at |
|  | 207672_at |
| EXT1 | 201995_at |
| FASLG | 210865_at |
|  | 211333_s_at |
| FGFR2 | 203638_s_at |
|  | 203639_s_at |
|  | 208225_at |
|  | 208228_s_at |
|  | 208229_at |
|  | 208234_x_at |
|  | 211398_at |
|  | 211399_at |
|  | 211400_at |
|  | 211401_s_at |
|  | 240913_at |
| GADD45A | 203725_at |
| IGF1R | 203627_at |
|  | 203628_at |
|  | 208441_at |
|  | 225330_at |
|  | 243358_at |
| IGFBP1 | 205302_at |
| IGFBP3 | 210095_s_at |
|  | 212143_s_at |
| INSR | 207851_s_at |
|  | 213792_s_at |
|  | 226212_s_at |
|  | 226216_at |
|  | 226450_at |
| LGMN | 201212_at |
| MXI1 | 202364_at |
| PPM1D | 204566_at |
|  | 230330_at |
| SEMA3C | 203788_s_at |
|  | 203789_s_at |
| SEPP1 | 201427_s_at |
|  | 231669_at |
| SESN1 | 218346_s_at |
| SLC5A3 | 1553313_s_at |
|  | 212944_at |
|  | 213167_s_at |
|  | 213164_at |
| SMAD4 | 1565702_at |
|  | 1565703_at |
|  | 202526_at |
|  | 202527_s_at |
|  | 235725_at |
| SOD2 | 215078_at |
|  | 215223_s_at |
|  | 216841_s_at |
|  | 221477_s_at |

TABLE 1-continued

"Evidence curated list of target genes" of the PI3K pathway used in the PI3K pathway models and associated probesets used to measure the mRNA expression level of the target genes.

| Target gene | Probeset |
|---|---|
| TLE4 | 204872_at |
|  | 214688_at |
|  | 216997_x_at |
|  | 233575_s_at |
|  | 235765_at |
| TNFSF10 | 202687_s_at |
|  | 202688_at |
|  | 214329_x_at |

The second list of target genes was generated using the manually-curated database of scientific publications provided within Thomson-Reuters' Metacore (last accessed May 14, 2013). The database was queried for genes that are transcriptionally regulated directly downstream of the family of human FOXO transcription factors (i.e., FOXO1, FOXO3A, FOXO4 and FOXO6). This query resulted in 336 putative FOXO target genes that were further analyzed as follows. First all putative FOXO target genes that only had one supporting publication were pruned. Next a scoring function was introduced that gave a point for each type of experimental evidence, such as ChIP, EMSA, differential expression, knock down/out, luciferase gene reporter assay, sequence analysis, that was reported in a publication. The same experimental evidence is sometimes mentioned in multiple publications resulting in a corresponding number of points, e.g., two publications mentioning a ChIP finding results in twice the score that is given for a single ChIP finding. Further analysis was performed to allow only for genes that had diverse types of experimental evidence and not only one type of experimental evidence, e.g., differential expression. Finally, an evidence score was calculated for all putative FOXO target genes and all putative FOXO target genes with an evidence score of 6 or more were selected (shown in Table 2). The cut-off level of 6 was chosen heuristically as it was previously shown that approximately 30 target genes suffice largely to determine pathway activity.

A list of these target genes may be called a "database-based list of target genes". Such a curated target gene list has been used to construct computational models that can be applied to samples coming from different tissue sources.

TABLE 2

"Database-based list of target genes" of the PI3K pathway used in the Bayesian network models and associated probesets used to measure the mRNA expression level of the target genes.

| Target gene | Probeset |
|---|---|
| AGRP | 207193_at |
| ATG14 | 204568_at |
| BCL2L11 | 1553088_a_at |
|  | 1553096_s_at |
|  | 1555372_at |
|  | 1558143_a_at |
|  | 208536_s_at |
|  | 222343_at |
|  | 225606_at |
| BCL6 | 203140_at |
|  | 215990_s_at |
| BIRC5 | 202094_at |
|  | 202095_s_at |
|  | 210334_x_at |
| BNIP3 | 201848_s_at |
|  | 201849_at |

TABLE 2-continued

"Database-based list of target genes" of the PI3K pathway used in the Bayesian network models and associated probesets used to measure the mRNA expression level of the target genes.

| Target gene | Probeset |
|---|---|
| CAT | 201432_at |
|  | 211922_s_at |
|  | 215573_at |
| CAV1 | 203065_s_at |
|  | 212097_at |
| CCNG2 | 1555056_at |
|  | 202769_at |
|  | 202770_s_at |
|  | 211559_s_at |
|  | 228081_at |
| CDKN1A | 1555186_at |
|  | 202284_s_at |
| CDKN1B | 209112_at |
| FASLG | 210865_at |
|  | 211333_s_at |
| FBXO32 | 225801_at |
|  | 225803_at |
|  | 225345_s_at |
|  | 225328_at |
| GADD45A | 203725_at |
| IGFBP1 | 205302_at |
| KLF2 | 219371_s_at |
|  | 226646_at |
| KLF4 | 220266_s_at |
|  | 221841_s_at |
| MYOD1 | 206656_s_at |
|  | 206657_s_at |
| NOS3 | 205581_s_at |
| PCK1 | 208383_s_at |
| PDK4 | 1562321_at |
|  | 205960_at |
|  | 225207_at |
| POMC | 205720_at |
| PPARGC1A | 1569141_a_at |
|  | 219195_at |
| PRDX3 | 201619_at |
|  | 209766_at |
| RAG1 | 1554994_at |
|  | 206591_at |
| RAG2 | 215117_at |
| RBL2 | 212331_at |
|  | 212332_at |
| SESN1 | 218346_s_at |
| SIRT1 | 218878_s_at |
| SOD2 | 215078_at |
|  | 215223_s_at |
|  | 216841_s_at |
|  | 221477_s_at |
| STK11 | 204292_x_at |
|  | 231017_at |
|  | 41657_at |
| TNFSF10 | 202687_s_at |
|  | 202688_at |
|  | 214329_x_at |
| TXNIP | 201008_s_at |
|  | 201009_s_at |
|  | 201010_s_at |

The third list of target genes was generated on the basis of the two aforementioned lists, i.e., the evidence curated list (see Table 1) and the database-based list (see Table 2). Three criteria have been used to further select genes from these two lists. The first criterion is related to the function attributed to the target genes. Functions attributed to genes can be found in scientific literature, but are often available in public databases such as the OMIM database of the NIH (accessible via "ncbi.nlm.nih.gov/omim"). Target genes from the evidence curated list in Table 1 and the database-based list in Table 2 that were found to be attributed to be involved in processes essential to cancer, such as apoptosis, cell cycle, tumor suppression/progression, DNA repair, differentiation, were selected in the third list. Lastly, target genes that were found to have a high differential expression in cell line experiments with known high PI3K/low FOXO activity versus known low PI3K/high FOXO activity were selected. Herein, target genes that had a minimum expression difference of $2^{0.5}$ (herein: on a probeset level) between the "on" and "off" state of FOXO transcription averaged over multiple samples were included in the third list. The third criterion was especially aimed at selecting the most discriminative target genes. Based on the expression levels in cell line experiments with multiple samples with known high PI3K/low FOXO activity and multiple samples with known low PI3K/high FOXO activity, an odds ratio (OR) was calculated. Herein, the odds ratio was calculated per probeset using the median value as a cut-off and a soft boundary representing uncertainty in the measurement. Target genes from the evidence curated list and the database-based list were ranked according to the "soft" odds ratio and the highest ranked (OR>2) and lowest ranked (OR<1/2, i.e., negatively regulated target genes) target genes were selected for the third list of target genes.

Taking into account the function of the gene, the differential expression in "on" versus "off" signaling and a higher odds ratio, a set of target genes was found (shown in Table 3) that was considered to be more probative in determining the activity of the PI3K signaling pathway. Such a list of target genes may be called a "shortlist of target genes". Hence, the target genes reported in Table 3 are useful according to the present disclosure. Nonetheless, given the relative ease with which acquisition technology such as microarrays can acquire expression levels for large sets of genes, it is contemplated to utilize some or all of the target genes of Table 3, and optionally additionally use on, two, some, or all of the remaining target genes of Table 1 and Table 2.

TABLE 3

"Shortlist of target genes" of the PI3K pathway based on the evidence curated list of target genes and the database-based list of target genes.
Target gene AGRP
BCL2L11
BCL6
BNIP3
BTG1
CAT
CAV1
CCND1
CCND2
CCNG2
CDKN1A
CDKN1B
ESR1
FASLG
FBXO32
GADD45A
INSR
MXI1
NOS3
PCK1
POMC
PPARGC1A
PRDX3
RBL2
SOD2
TNFSF10

A further selection of the evidence curated list of target genes was made by the inventors. The target genes of the evidence curated list that were proven to be more probative in determining the activity of the PI3K pathway from the training samples were selected. Target genes were selected based on the "soft" odds ratio with the top 12 genes selected for the "12 target genes shortlist".

TABLE 4

"12 target genes shortlist" of target genes of the PI3K pathway based on the evidence curated list of target genes.
Target gene

FBXO32
BCL2L11
SOD2
TNFSF10
BCL6
BTG1
CCNG2
CDKN1B
BNIP3
GADD45A
INSR
MXI1

(ii) Training and Using the Mathematical Model Before the mathematical model can be used to infer the activity of the cellular signaling pathway, here, the PI3K pathway, in a subject, the model must be appropriately trained.

If the mathematical model is a probabilistic model. e.g., a Bayesian network model, based at least in part on conditional probabilities relating the FOXO TF element and expression levels of the one or more target gene(s) of the PI3K pathway measured in the sample of the subject, the training may, for example, be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the one or more target gene(s) of the PI3K pathway measured in the sample of the subject, the training may, for example, be performed as described in detail in the unpublished US provisional patent application U.S. 61/745,839 ("Assessment of cellular signaling pathway activity using linear combination(s) of target gene expressions").

Herein, an exemplary Bayesian network model as shown in FIG. 1 was used to model the transcriptional program of the PI3K pathway in a simple manner. The model consists of three types of nodes: (a) a transcription factor (TF) element (with states "absent" and "present") in a first layer 1; (b) target gene(s) $TG_1$, $TG_2$, $TG_n$ (with states "down" and "up") in a second layer 2, and, in a third layer 3; (c) measurement nodes linked to the expression levels of the target gene(s). These can be microarray probesets $PS_{1,1}$, $PS_{1,2}$, $PS_{1,3}$, $PS_{2,1}$, $PS_{n,1}$, $PS_{n,m}$ (with states "low" and "high"), as, for example, used herein, but could also be other gene expression measurements such as RNAseq or RT-qPCR.

A suitable implementation of the mathematical model, herein, the exemplary Bayesian network model, is based on microarray data. The model describes (i) how the expression levels of the target gene(s) depend on the activation of the TF element, and (ii) how probeset intensities, in turn, depend on the expression levels of the respective target gene(s). For the latter, probeset intensities may be taken from fRMA pre-processed Affymetrix HG-U133Plus2.0 microarrays, which are widely available from the Gene Expression Omnibus (GEO, ncbi.nlm.nih.gov/geo) and ArrayExpress (ebi.ac.uk/arrayexpress).

As the exemplary Bayesian network model is a simplification of the biology of a cellular signaling pathway, herein, the PI3K pathway, and as biological measurements are typically noisy, a probabilistic approach was opted for, i.e., the relationships between (i) the TF element and the target gene(s), and (ii) the target gene(s) and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and inferring backwards in the model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This latter probability is hence the primary read-out that may be used to indicate activity of the cellular signaling pathway, herein, the PI3K pathway, which can next be translated into the odds of the cellular signaling pathway being active by taking the ratio of the probability of being active vs. being inactive (i.e., the odds are given by p./(1−p) if p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target gene(s) have been carefully hand-picked. If the TF element is "absent", it is most likely that the target gene is "down", hence a probability of 0.95 is chosen for this, and a probability of 0.05 for the target gene being "up". The latter (non-zero) probability is to account for the (rare) possibility that the target gene is regulated by other factors or accidentally observed "up" (e.g. because of measurement noise). If the TF element is "present", then with a probability of 0.70 the target gene is considered "up", and with a probability of 0.30 the target gene is considered "down". The latter values are chosen this way, because there can be several reasons why a target gene is not highly expressed even though the TF element is present, for instance, because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target gene(s) and their respective probesets have been calibrated on experimental data. For the latter, in this example, microarray data was used from cell line experiments with defined active and inactive pathway settings, but this could also be performed using patient samples with known cellular signaling pathway activity status. The resulting conditional probability tables are given by:

A: For Upregulated Target Genes

|  | $PS_{i,j}$ = low | $PS_{i,j}$ = high |
|---|---|---|
| $TG_i$ = down | $\dfrac{AL_{i,j}+1}{AL_{i,j}+AH_{i,j}+2}$ | $\dfrac{AH_{i,j}+1}{AL_{i,j}+AH_{i,j}+2}$ |
| $TG_i$ = up | $\dfrac{PL_{i,j}+1}{PL_{i,j}+PH_{i,j}+2}$ | $\dfrac{PH_{i,j}+1}{PL_{i,j}+PH_{i,j}+2}$ |

B: For Downregulated Target Genes

|  | $PS_{i,j}$ = low | $PS_{i,j}$ = high |
|---|---|---|
| $TG_i$ = down | $\dfrac{PL_{i,j}+1}{PL_{i,j}+PH_{i,j}+2}$ | $\dfrac{PH_{i,j}+1}{PL_{i,j}+PH_{i,j}+2}$ |
| $TG_i$ = up | $\dfrac{AL_{i,j}+1}{AL_{i,j}+AH_{i,j}+2}$ | $\dfrac{AH_{i,j}+1}{AL_{i,j}+AH_{i,j}+2}$ |

In these tables, the variables $AL_{i,j}$, $AH_{i,j}$, $PL_{i,j}$, and $PH_{i,j}$ indicate the number of calibration samples with an "absent" (A) or "present" (P) transcription complex that have a "low" (L) or "high" (H) probeset intensity, respectively. Dummy counts have been added to avoid extreme probabilities of 0 and 1.

To discretize the observed probeset intensities, for each probeset $PS_{i,j}$ a threshold $t_{i,j}$ was used, below which the observation is called "low", and above which it is called "high". This threshold has been chosen to be the (weighted) median intensity of the probeset in the used calibration dataset. Due to the noisiness of microarray data, a fuzzy method was used when comparing an observed probeset intensity to its threshold, by assuming a normal distribution with a standard deviation of 0.25 (on a log 2 scale) around the reported intensity, and determining the probability mass below and above the threshold.

If instead of the exemplary Bayesian network described above, a (pseudo-)linear model as described above was employed, the weights indicating the sign and magnitude of the correlation between the nodes and a threshold to call whether a node is either "absent" or "present" would need to be determined before the model could be used to infer cellular signaling pathway activity in a test sample. One could use expert knowledge to fill in the weights and the threshold a priori, but typically the model would be trained using a representative set of training samples, of which, for example, the ground truth is known, e.g., expression data of probesets in samples with a known "present" transcription factor complex (=active cellular signaling pathway) or "absent" transcription factor complex (=passive cellular signaling pathway).

Known in the field are a multitude of training algorithms (e.g., regression) that take into account the model topology and changes the model parameters, here, the weights and the threshold, such that the model output, here, a weighted linear score, is optimized. Alternatively, it is also possible to calculate the weights directly from the expression observed levels without the need of an optimization algorithm.

A first method, named "black and white"-method herein, boils down to a ternary system, in which each weight is an element of the set {−1, 0, 1}. If this is put in a biological context, the −1 and 1 correspond to target genes or probesets that are down- and up-regulated in case of cellular signaling pathway activity, respectively. In case a probeset or target gene cannot be statistically proven to be either up- or down-regulated, it receives a weight of 0. In one example, a left-sided and right-sided, two sample t-test of the expression levels of the active cellular signaling pathway samples versus the expression levels of the samples with a passive cellular signaling pathway can be used to determine whether a probe or gene is up- or down-regulated given the used training data. In cases where the average of the active samples is statistically larger than the passive samples, i.e., the p-value is below a certain threshold, e.g., 0.3, the target gene or probeset is determined to be up-regulated. Conversely, in cases where the average of the active samples is statistically lower than the passive samples, the target gene or probeset is determined to be down-regulated upon activation of the cellular signaling pathway. In case the lowest p-value (left- or right-sided) exceeds the aforementioned threshold, the weight of the target gene or probeset can be defined to be 0.

A second method, named "log odds"-weights herein, is based on the logarithm (e.g., base e) of the odds ratio. The odds ratio for each target gene or probeset is calculated based on the number of positive and negative training samples for which the probeset/target gene level is above and below a corresponding threshold, e.g., the (weighted) median of all training samples. A pseudo-count can be added to circumvent divisions by zero. A further refinement is to count the samples above/below the threshold in a somewhat more probabilistic manner, by assuming that the probeset/target gene levels are, e.g., normally distributed around its observed value with a certain specified standard deviation (e.g., 0.25 on a 2-log scale), and counting the probability mass above and below the threshold. Herein, an odds ratio calculated in combination with a pseudo-count and using probability masses instead of deterministic measurement values is called a "soft" odds ratio.

Further details regarding the inferring of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

Herein, publically available data on the expression of a HUVEC cell line with a stable transfection of a FOXO construct that is inducible upon stimulation with 4OHT (GSE16573 available from the Gene Expression Omnibus, last accessed Oct. 6, 2014) was used as an example to train the PI3K pathway model. The cell lines with the inducible FOXO construct that were stimulated for 12 hours with 4OHT were considered as the FOXO active samples (n=3), whereas the passive FOXO samples were the cell lines with the construct without 4OHT stimulation (n=3).

(B) Wnt Pathway

The selection of target genes of the Wnt pathway was previously described in WO 2013/011479 A2 and WO 2014/102668 A2. The "Evidence curated list of target genes" for the Wnt pathway was used as described in this Example above for PI3K target genes in order to generate the "Shortlist of target genes" for the Wnt pathway and the "12 target genes shortlist" of target genes of the Wnt pathway.

TABLE 5

"Evidence curated list of target genes" of the Wnt pathway used in the Bayesian network models and associated probesets used to measure the mRNA expression level of the target genes.
Target gene ADRA2C
ASCL2
AXIN2
BMP7
CCND1
CD44
COL18A1
DEFA6
DKK1
EPHB2
EPHB3
FAT1
FZD7
GLUL
HNF1A
IL8
KIAA1199
KLF6
LECT2
LEF1
LGR5
MYC
NKD1
OAT
PPARG
REG1B
RNF43
SLC1A2
SOX9
SP5
TBX3
TCF7L2
TDGF1
ZNRF3

TABLE 6

"Shortlist of target genes" of the Wnt pathway based on the evidence curated list of target genes.
Target gene KIAA1199
AXIN2
CD44
RNF43
MYC
TBX3
TDGF1
SOX9
ASCL2
IL8
SP5
ZNRF3
EPHB2
LGR5
EPHB3
KLF6
CCND1
DEFA6
FZD7

TABLE 7

"12 target genes shortlist" of target genes of the Wnt pathway based on the evidence curated list of target genes.
Target gene

AXIN2
CD44
LGR5

TABLE 7-continued

"12 target genes shortlist" of target genes of the Wnt pathway based on the evidence curated list of target genes.
Target gene

CEMIP (KIAA1199)
MYC
CXCL8 (IL8)
SOX9
EPHB3
RNF43
TDGF1
ZNRF3
DEFA6

(C) ER Pathway

Please note that with respect to WO 2013/011479 A2 and WO 2014/102668 A2, herein, the rank order of the ER target genes is slightly changed because new literature evidence was added. The ER target genes were selected and ranked in a similar way as described in Example 3 of WO 2014/102668 A2. The genes were ranked by combining the literature evidence score and the individual ability of each gene to differentiate between an active and inactive pathway within the model. This ranking was based on a linear combination of weighted false positive and false negative rates obtained for each gene when training the model with a training set of MCF7 cell line samples, which were depleted of estrogen and subsequently remained depleted or were exposed to 1 nM estrogen for 24 hours (GSE35428), and testing the model with the training set and two other training sets in which MCF7 cells were depleted of estrogen and subsequently remained depleted or were exposed to 10 nM or 25 nM estrogen (GSE11352 and GSE8597, respectively).

(Note that a combination of weighted false positives and false negatives (instead of odds ratios) was used to account for the different experimental conditions used in the various sets. The different weights were set according with the inventor's confidence that the false positives (negatives) were a consequence of the model and not of the different experimental condition the sample had been subjected to. For example, in all experiments the MCF7 cell line samples were first depleted of estrogen for a period of time before being exposed to estrogen or further depleted for another 24 hours. A shorter depletion time could cause the pathway to still being active despite the estrogen depletion, in this case a false positive would have less weight than when both the test and training samples were depleted for the same amount of time.).

Based on additional literature review and the examination of the magnitude of differential expression between active and inactive samples as discussed in more detail below, PDZK1 was selected as a direct target gene of the ER pathway. After manually evaluating the additional scientific papers for experimental evidence of putative target genes of the ER pathway using an analogous methodology as described in this example (for PI3K), a number of additional putative ER target genes were identified.

Putative ER target genes were analyzed for the presence of a gene promoter/enhancer region containing an estrogen response element (ERE) motif. The ERE motif should be proven to respond to estrogen. e.g., by means of a transient transfection assay in which the specific ERE motif is linked to a reporter gene. The presence of the ERE motif should be confirmed by, e.g., an enriched motif analysis of the gene promoter/enhancer region. In addition, ER (differentially) binds in vivo to the promoter/enhancer region of the gene in question, demonstrated by, e.g., a ChIP/CHIP experiment or a chromatin immunoprecipitation assay. For example, ER should be proven to bind to the promoter/enhancer region of the gene when the ER pathway is active, and, for example, does not bind (or weakly binds) to the gene promoter/enhancer region of the gene if the ER pathway is not active. Finally, the gene is differentially transcribed when the ER pathway is active, demonstrated by, e.g., fold enrichment of the mRNA of the gene in question through real time PCR, or microarray experiment, or the demonstration that RNA Pol II binds to the promoter region of the gene through an immunoprecipitation assay.

The selection was done by defining as ER target genes the genes for which enough and well documented experimental evidence was gathered from literature proving that all three criteria mentioned above were met. A suitable experiment for collecting evidence of ER differential binding is to compare the results of, e.g., a ChIP/CHIP experiment in a cancer cell line that responds to estrogen (e.g., the MCF-7 cell line), when exposed or not exposed to estrogen. After evaluating all additional scientific papers, a new ranking for all putative target genes was based on the strength of experimental evidence found in the literature. Consequently, one putative ER target gene, PDZK1, achieved an experimental evidence score above the set threshold. Therefore, PDZK1 was considered to be a bona fide direct target gene of the ER pathway.

In the original selection of ER target genes, only the capacity of differentiating active vs. inactive samples, calculated using the 'soft' odds ratio, was considered. In the current analysis, the magnitude of differential expression was also included in the evaluation. Since the magnitude of differential expression signal is next to the 'soft' odds ratio as an important feature of a well-designed assay, this new selection method is anticipated to be an improvement over the original criteria. Differential gene expression magnitude was estimated by averaging the difference of mean gene expression between ER active (on) samples and ER inactive (off) samples on a selection of Affymetrix HG1133Plus2 data sets, namely GSE35427, GSE11352, GSE21618, GSE8597 and two in-house generated datasets including multiple breast cancer cell lines stimulated with estradiol (E2) or a control. Mean gene expression was computed separately for each Affymetrix probeset related to the gene for each dataset. Only probesets that were significantly differentially expressed were taken into account in the average. The average differential expression between samples stimulated with estradiol, i.e. ER active samples, and control/unstimulated samples, i.e. ER passive samples, of PDZK1 was 2.08. This differential expression is exceptionally high (average over all up-regulated gens is 0.88) and is comparable to the target genes with the highest differential expression, e.g. PGR with an average differential expression of 2.14. In addition, the 'soft' odds ratio of PDZK1 (average 26.6) is also higher than average (19.03).

In the following examples we compare the original 13 ER target gene list (GREB1, PGR, XBP1, CA12, SOD1, CTSD, IGFBP4, TFF1, SGK3, NRIP1, CELSR2, WISP2, and AP1B1) model (hereafter called short list model) to a new 14 ER target gene model constructed using PDZK1 and the original 13 ER target gene list (hereafter called short list+ PDZK1 model). Both Bayesian network models were trained in the exact same way (using the Affymetrix HGU133Plus2 GSE8597 dataset) with the only difference being the list of ER target genes.

In example 1 the ER pathway activity was computed for a selection of Affymetrix HGU133Plus2 datasets that exemplify typical breast cancer and normal breast tissue samples (public datasets GSE12276, GSE10870, and GSE21653) containing 256 ER positive breast cancer samples, 195 ER negative breast cancer samples, 27 normal breast tissue samples, and 94 unknown ER status breast cancer samples. While the ER pathway is expected to be inactive in ER negative breast cancer and normal breast, about 50 to 70% of ER positive breast cancers are expected to be active, based on response to hormone therapy data. The proportion of ER positive breast cancer samples predicted to be active by the short list model (74%) and by the short list+PDZK1 model (73%) is comparable and similar to the proportion of ER positive cancer patients to respond to Hormone therapy. Furthermore, the average of the probability of ER activation, over all ER positive samples, computed by the short list+PDZK1 (average log 2 odds ratio: 2.73) list model is slightly higher that the average probability of activation predicted by the short list model (average log 2 odds ratio: 2.70, with a difference of 0.03 in the log 2 odds ratio scale) making them comparable for this type of sample. An unexpected beneficial technical effect of including PDZK1 occurs when analyzing ER negative breast cancer and normal tissue samples: the average of the probability of ER activation computed by the short list+PDZK1 list model (average log 2 odds ratio: −7.3) is considerably lower than the average probability of activation predicted by the short list model (average log 2 odds ratio: 6.8, with a difference of 0.5 in the log 2 odds ratio scale, Wilcoxon rank test 2-sided pv=0.02), making the short list+PDZK1 model technically better than the short model in this situation. Furthermore, this improvement is more than a minute scaling of the predicted pathway activity levels which is anticipated in case one more target genes is added to the model, therefore the addition of PDZK1 renders an unexpected, advantageous technical effect.

In example 2 the ER pathway activity was computed for public Affymetrix HGU133Plus2 datasets GSE8597, GSE35428, GSE11352, that exemplify experiments where estrogen sensitive breast cell lines (in this case MCF7) are exposed to or deprived of estrogen stimulation. It is well known that exposure the estrogen activates the ER pathway in MCF7 cell lines and deprivation of estrogen shuts the ER pathway down in MCF7 cell lines. Also, in this case the short list+PDZK1 model seems to be technically superior to the short list model, both for the case where MCF7 cell lines are exposed to estrogen, where the predicted activity computed by the short list+PDKZ1 model (average log 2 odds ratio: 14.7) is higher than predicted activity computed by the short list model (average log 2 odds ratio: 14.0, a difference of 0.7 on the log 2 odds ratio scale). The predicted activity computed for all samples deprived of estrogen stimulation by the short list+PDKZI model (average log 2 odds ratio: −7.7) is lower than predicted activity computed by the short list model (average log 2 odds ratio: −7.3, a difference of 0.4 on the log 2 odds ratio scale) for 85% of the 27 samples that were deprived of estrogen. Also this improvement is more than a minute scaling of the predicted pathway activity levels which is anticipated in case one more target genes is added to the model, therefore the addition of PDZK1 renders an unexpected, advantageous technical effect.

To probe the effect of the new gene in PCR assays, in the following examples we compare a 11 ER target gene list (GREB1, PGR, XBP1, CA12, SOD1, CTSD, IGFBP4, TFF1, SGK3, NRIP1, CELSR2, ERBB2, and ESR1) model (hereafter called PCR list model) to a new 12 ER target gene model constructed using PDZK1 and the above mentioned 11 ER target gene list (hereafter called PCR list+PDZK1 model). Both Bayesian network models were trained in exactly the same way (using a gene expression data generated by RT-qPCR, from an in-house estrogen deprivation/stimulation experiment in MCF7 cell lines) with the only difference being the addition of the PDZK1 ER target gene in the PCR list+PDZK1 model. The ER pathway activity was computed for a total of 12 samples: 6 deprived from estrogen and 6 stimulated with estrogen. Here again the model containing PDZK1 (PCR list+PDZK1 model) seems to be technically superior to the model without PDZK1 (PCR list model), both for the case of exposed to estrogen, where the predicted activity computed by the PCR list+PDKZ1 model (average log 2 odds ratio: 4.7) is higher than predicted activity computed by the PCR list model (average log 2 odds ratio: 3.9, a difference of 0.8 on the log 2 odds ratio scale). The predicted activity for the estrogen deprived samples computed by the PCR list+PDZK1 model (average log 2 odds ratio: −5.1) is lower than predicted activity computed by the short list model (average log 2 odds ratio: −4.5, a difference of 0.6 on the log 2 odds ratio scale). This difference is very important in models that use a small amount of "probes" to measure the sample ER target gene profile, since they usually have less discrimination power (note the low average predicted activities). In conclusion, this improvement is more than a minute scaling of the predicted pathway activity levels which is anticipated in case one more target genes is added to the model, therefore the addition of PDZK1 renders an unexpected, advantageous technical effect.

As discussed above, the selection of target genes of the ER pathway was previously described in WO 2013/011479 A2 and WO 2014/102668 A2. The "Evidence curated list of target genes" for the HH pathway was used as described in this Example above for PI3K target genes in order to generate the "Shortlist of target genes" for the HH pathway and the "12 target genes shortlist" of target genes of the HH pathway, based on the additional literature review and inclusion of the PDZK1 target gene.

TABLE 8

"Evidence curated list of target genes" of the ER pathway used in the Bayesian network models and associated probesets used to measure the mRNA expression level of the target genes.
Target gene AP1B1
ATP5J
COL18A1
COX7A2L
CTSD
DSCAM
EBAG9
ESR1
HSPB1
KRT19
NDUFV3
NRIP1
PGR
PISD
PRDM15
PTMA
RARA
SOD1
TFF1
TRIM25
XBP1
GREB1
IGFBP4
MYC
SGK3
WISP2
ERBB2
CA12
CDH26
CELSR2

TABLE 9

"Shortlist of target genes" of the ER pathway based on the evidence curated list of target genes.
Target gene CDH26
SGK3
PGR
GREB1
CA12
XBP1
CELSR2
WISP2
DSCAM
ERBB2
CTSD
TFF1
NRIP1
PDZK1
IGFBP4
ESR1
SOD1
AP1B1

TABLE 10

"12 target genes shortlist" of target genes of the ER pathway based on the evidence curated list of target genes.
Target gene

TFF1
GREB1
PGR
SGK3
PDZK1
IGFBP4
NRIP1
CA12
XBP1
ERBB2
ESR1
CELSR2

(D) HH Pathway

The selection of target genes of the HH pathway was previously described in WO 2013/011479 A2 and WO 2014/102668 A2. The "Evidence curated list of target genes" for the HH pathway was used as described in this Example above for PI3K target genes in order to generate the "Shortlist of target genes" for the HH pathway and the "12 target genes shortlist" of target genes of the HH pathway.

TABLE 11

"Evidence curated list of target genes" of the HH pathway used in the Bayesian network models and associated probesets used to measure the mRNA expression level of the target genes.
Target gene GLI1
PTCH1
PTCH2
HHIP
SPP1
TSC22D1
CCND2
H19
IGFBP6
TOM1
JUP
FOXA2
MYCN
NKX2_2
NKX2_8
RAB34
MIF

TABLE 11-continued

"Evidence curated list of target genes" of the HH pathway used in the Bayesian network models and associated probesets used to measure the mRNA expression level of the target genes.
Target gene GLI3
FST
BCL2
CTSL1
TCEA2
MYLK
FYN
PITRM1
CFLAR
IL1R2
S100A7
S100A9
CCND1
JAG2
FOXM1
FOXF1
FOXL1

TABLE 12

"Shortlist of target genes" of the HH pathway based on the evidence curated list of target genes.
Target gene GLI1
PTCH1
PTCH2
IGFBP6
SPP1
CCND2
FST
FOXL1
CFLAR
TSC22D1
RAB34
S100A9
S100A7
MYCN
FOXM1
GLI3
TCEA2
FYN
CTSL1

TABLE 13

"12 target genes shortlist" of target genes of the HH pathway based on the evidence curated list of target genes.
Target gene

GLI1
PTCH1
PTCH2
CCND2
IGFBP6
MYCN
FST
RAB34
GLI3
CFLAR
S100A7
S100A9

Example 2: Determining Risk Score

In general, many different formulas can be devised for determining a risk score that indicates a risk that a subject will experience a clinical event within a certain period of time and that is based at least in part on a combination of inferred activities of two or more cellular signaling pathways in a subject, i.e.:

$$MPS = F(P_i) + X, \text{ with } i = 1 \ldots N, \quad (3)$$

wherein MPS denotes the risk score (the term "MPS" is used herein as an abbreviation for "Multi-Pathway Score" in order to denote that the risk score is influenced by the inferred activities of two or more cellular signaling pathways), $P_i$ denotes the activity of cellular signaling pathway i, N denotes the total number of cellular signaling pathways used for calculating the risk score, and X is a placeholder for possible further factors and/or parameters that may go into the equation. Such a formula may be more specifically a polynomial of a certain degree in the given variables, or a linear combination of the variables. The weighting coefficients and powers in such a polynomial may be set based on expert knowledge, but typically a training data set with known ground truth, e.g., survival data, is used to obtain estimates for the weighting coefficients and powers of Eq. (3). The inferred activities are combined using Eq. (3) and will subsequently generate an MPS. Next, the weighting coefficients and powers of the scoring function are optimized such that a high MPS correlates with a higher probability that the patient will experience the clinical event, and vice versa. Optimizing the scoring function's correlation with survival data can be done using a multitude of analysis techniques. e.g., a Cox proportional hazards test (as exemplified herein), a log-rank test, a Kaplan-Meier estimator in conjunction with standard optimization techniques, such as gradient-descent or manual adaptation, and so on.

In their experiments, the inventors found no reason to anticipate a power law response between the activities of the cellular signaling pathways and the recurrence risk, hence Eq. (3) can be simplified:

$$MPS = w_1 \cdot P_1 + w_2 \cdot P_2 + \ldots + w_N \cdot P_N + X, \quad (4)$$

wherein $w_1, \ldots, w_N$ denote weighting coefficients.

In this example, the clinical event is cancer, in particular, breast cancer, and the inferred activities of the PI3K pathway, the Wnt pathway, the ER pathway, the HH pathway are considered, as discussed in detail herein as well as in the published international patent application WO 2013/011479 A2 ("Assessment of cellular signaling pathway activity using probabilistic modeling of target gene expression") and/or in the published international patent application WO 2014/102668 A2 ("Assessment of cellular signaling pathway activity using linear combination(s) of target gene expressions").

The formulas that are exemplified herein take into account the activities of the PI3K pathway and one or more of the Wnt pathway, the ER pathway, and the HH pathway. These formulas are based on the inventors' observations derived from cancer biology research as well as from correlations discovered by the inventors in publically available datasets between survival and the activities of the PI3K pathway, the Wnt pathway, the ER pathway, and the HH pathway. Early developmental pathways, like the Wnt pathway and the HH pathway, are thought to play a role in metastasis caused by cancer cells which have reverted to a more stem cell like phenotype, called cancer stem cells. Indeed, the inventors' believe that sufficient indications are available for the early developmental pathways, such as the Wnt pathway, to play a role in cancer metastasis, enabling metastatic cancer cells to start dividing in the seeding location into another organ or tissue. Metastasis is associated with worse prognosis and represents a form of cancer recurrence, thus activity of early developmental pathways, such as the Wnt pathway and the HH pathway, in cancer cells is expected by the inventors to be predictive for worse prognosis. The presumed role of the Wnt pathway and the HH pathway in cancer progression and metastasis is based on pre-clinical research, and has not been shown in subjects, since no methods for measuring their activity have been available. In addition, the inventors discovered sufficient indications in publically available datasets that show a correlation between activity of the ER pathway being a (relatively) protective mechanism for survival and activity of the PI3K pathway, which is correlated with a worse prognosis. Accordingly, passivity of the ER pathway and activity of the PI3K pathway were found by the inventors to be correlated with a poor outcome in breast cancer patients.

These inventors' observations from biology research and the clinical correlations that the activities of the PI3K pathway, the Wnt pathway, and the HH pathway may play a role in cancer recurrence and overall survival and that activity of the ER pathway seems to be linked to a good clinical outcome are combined herein in the following exemplary formula, which is a special case of Eq. (4):

$$MPS = w_p \cdot P_p + w_w \cdot P_w + w_e \cdot P_e + w_h \cdot P_h + X, \quad (5)$$

wherein $P_p$, $P_w$, $P_e$, and $P_h$ denote the inferred activity of the PI3K pathway, the Wnt pathway, the ER pathway, and the HH pathway, respectively (e.g., in the range between 0 and 1), $w_p$ is a positive constant weighting coefficient, $w_w$ and $w_h$ are non-negative constant weighting coefficients, and $w_e$ is a non-positive constant weighting coefficient. With this formula, the indicated risk that the subject will experience the clinical event within the certain period of time monotonically increases with an increasing value of the sum.

In the following examples, the inventors have exemplarily used the inferred activities from the Bayesian networks of the PI3K pathway using the shortlist of target genes shown in Table 3 and the training as discussed herein, the Wnt pathway using the evidence curated list of target genes shown in Table 1 of WO 2013/011479 A2 and the training as discussed therein, the ER pathway using the evidence curated list of target genes shown in Table 2 of WO 2013/011479 A2 and the training discussed therein, and the HH pathway using the evidence curated list of target genes shown in Table 3 of WO 2013/011479 A2 and the training discussed therein. Alternatively, the pathway activities can be inferred by means of alternative methods such as using (pseudo-)linear models as discussed herein and in more detail in WO 2014/102668 A2 or alternatively the herein exemplarily used lists of target genes can be replaced by a further selection of the target genes from the evidence curated lists based on their probative nature that were proven to obtain comparable results with respect to the inferred pathway activities. The alternative lists are discussed herein for the PI3K pathway (see Tables 1 and 2) and discussed in WO 2013/011479 A2 for the Wnt pathway (see Table 6 of WO 2013/011479 A2), the ER pathway (see Table 7 of WO 2013/011479 A2), and the HH pathway (see Table 8 of WO 2013/011479 A2).

Herein, we describe an exemplary method to infer appropriate values for the weighting coefficients $w_p$, $w_w$, $w_e$, and $w_h$ using Cox's proportional hazards models. A Cox's proportional hazard model is fitted to a training set consisting of a suitable number (for example >100, representing the diverse subsets of cancer types) of samples with inferred activities $P_p$, $P_w$, $P_e$, and $P_h$ and survival data, i.e., the survival time and censoring information using, for example MATLAB, (MATLAB R2014a, The MathWorks Inc., Natick, Mass.) or R (v3.0.3, R Core Team (2014). R: A language and environment for statistical computing. R Foundation for Statistical Computing, Vienna, Austria). Exemplarily, the publically available breast cancer samples from GSE6532 originating from the Guy's hospital (n=87) and the samples from GSE9195 (n=77), accessible at ncbi.nlm.nih.gov/geo/, last accessed Jul. 20, 2014, were used as training dataset. A Cox's proportional hazards regression model is fitted for the activity of every pathway, resulting in a Cox's coefficient per pathway activity, its associated standard error (SE) of the coefficient estimate, a hazard ratio (HR), which is the exponent of the Cox's coefficient, a 95% confidence interval of the hazard ratio and a p-value derived from the Cox's coefficient and the standard error as can be seen in Table 14. The sign of the coefficient estimate indicates whether the pathway activity is either protective for the clinical event in case of a negative coefficient or predict worse prognosis in case of a positive coefficient. The modulus of the coefficient indicates the strength of the risk score with respect to prognosis.

TABLE 14

Results of Cox's proportional hazard regression on the combined training sets GSE6532 and GSE9195.

| Risk score | Cox's coefficient | SE | HR | HR 95% CI | | p-value |
|---|---|---|---|---|---|---|
| $P_p$ | 0.80 | 0.41 | 2.24 | 1.00 | 5.01 | 2.53e−02 |
| $P_w$ | 1.30 | 0.85 | 3.67 | 0.69 | 19.38 | 6.30e−02 |
| $P_e$ | −1.02 | 0.52 | 0.36 | 0.13 | 0.99 | 2.39e−02 |
| $P_h$ | 0.83 | 0.54 | 2.29 | 0.79 | 6.61 | 6.37e−02 |

It has been found by the inventors that the Cox's coefficients fitted for the activities of the respective cellular signaling pathways on a training data set, as shown, for example, in Table 14, are good values to use as linear weighting coefficients for the risk scores. Therefore these Cox's coefficients are, in one embodiment, used as the weighting coefficients in Eq. (5). Their suitability for use in determining a risk score has been evaluated in great detail, as described in the following:

First the activity of the PI3K pathway was combined with the activity of the Wnt pathway, the ER pathway, and the HH pathway, respectively, resulting in the following equations:

$$MPS_{pw}=0.80(\pm 0.41)\cdot P_p+1.30(\pm 0.85)\cdot P_w \quad (6)$$

$$MPS_{pe}=0.80(\pm 0.41)\cdot P_p+(-1.02(\pm 0.52))\cdot P_e \quad (7)$$

$$MPS_{ph}=0.80(\pm 0.41)\cdot P_p+0.83(\pm 0.54)\cdot P_h \quad (8)$$

Next the activity of the PI3K pathway was combined with the activities of two other pathways from the group consisting of the Wnt pathway, the ER pathway, and the HH pathway, resulting in the following equations:

$$MPSP_{pwe}=0.80(\pm 0.41)\cdot P_p+1.30(\pm 0.85)\cdot P_w+(-1.02(\pm 0.52))\cdot P_e \quad (9)$$

$$MPSP_{pwh}=0.80(\pm 0.41)\cdot P_p+1.30(\pm 0.85)\cdot P_w+0.83(\pm 0.54)\cdot P_h \quad (10)$$

$$MPSP_{peh}=0.80(\pm 0.41)\cdot P_p+(-1.02(\pm 0.52))\cdot P_e+0.83(\pm 0.54)\cdot P_h \quad (11)$$

In one embodiment, the Cox's coefficients are used to parameterize the linear combination of the activities of the PI3K pathway, the Wnt pathway, the ER pathway, and the HH pathway listed in Eq. (5), which resulted in the following equation:

$$MPSP_{pweh}=0.80(\pm 0.41)\cdot P_p+1.30(\pm 0.85)\cdot P_w+(-1.02(\pm 0.52))\cdot P_e+0.83(\pm 0.54)\cdot P_h \quad (12)$$

wherein the standard errors of the coefficients are listed between the parentheses.

Alternatively, one can use (pseudo-)linear models to infer the pathway activity as described herein and in more detail in WO 2014/102668 A2 ("Assessment of cellular signaling pathway activity using linear combination(s) of target gene expressions") and use these inferred activities in a similar fashion as discussed above with pathway activities inferred with a probabilistic model. Inserting these linear models for pathway activity in Eqs. (6) to (12) eventually culminates, after expansion of the summations, into a linear combination that can be generalized into an equation with a single summation:

$$MPS_{probesets}=\Sigma w_{ij}\cdot E_{ij} \quad (13)$$

wherein $\Sigma$ is the sum of all i probesets of all j pathways, here the pathways are exemplarily PI3K, Wnt, ER and HH, $w_{ij}$ is the weight associated with the probeset, which equals the product of the weight associated with the pathway and the probeset or pathway, target gene and probeset, for the "single-layer" and "two-layer" linear models, respectively. Herein, the weight $w_{ij}$ is exemplarily chosen equal to the Cox's coefficient estimated from the training data set, of the i-th probeset of the j-th pathway, and $E_{ij}$ is the i-th probeset of the j-th pathway. A person skilled in the art will be able to adapt this equation to other measuring platforms such as (RT-q)PCR, sequencing, mRNA fish, and other suitable methods to detect expression levels of the target genes instead of the probesets originating from the Affymetrix HG-U133Plus2.0 exemplarily used herein.

Next the risk scores as described herein were tested on a combination of three other datasets: GSE20685 and GSE21653 are available at the gene expression omnibus, accessible at ncbi.nlm.nih.gov/geo/, last accessed Jul. 20, 2014, whereas E-MTAB-365 is available at ArrayExpress, accessible at ebi.ac.uk/arrayexpress/experiments/, last accessed Jul. 20, 2014. The three datasets combine a diverse set of in total 1005 breast cancer patients with complete survival time and censoring data. The risk scores for these patients were calculated according to Eqs. (6) to (13) and then the prognostic value of the risk scores was investigated using two methods that quantize such a prognostic value. These are Cox's proportional hazard regression models and Kaplan-Meier plots in conjunction with the log-rank statistical test:

The first method fits a Cox's proportional hazard model to the survival data with one or more covariates. In short, such a hazard model explains the variation in survival (clinical event) within the population based on the (numerical) value of the covariates. As a result of the fit, each included covariate will be assigned a hazard ratio (HR), which is the exponent of the Cox's coefficient, which quantifies the associated risk of the clinical event based on the covariate's value, e.g., a HR of two corresponds with a two times higher risk of the clinical event of interest for patients with an increase of one in the covariate's value. In detail, a value of HR=1 means that this covariate has no impact on survival, whereas for HR<1, an increase in the covariate number signifies a lower risk and a decrease in the covariate number signifies a higher risk, and for HR>1, an increase in the covariate number signifies a higher risk and a decrease in the covariate number signifies a lower risk. Along with the hazard ratios, the 95% confidence interval and p-values are reported (i.e., the one-sided probability that the hazard ratio is significantly less or greater than one). All risk scores are scaled such that the scale (minimum to maximum value) of the risk score is one in order to make a direct comparison of hazard ratios straightforward.

The latter method involves plotting a Kaplan-Meier curve that represents the probability of surviving the clinical event as a function of time. For example, by plotting the Kaplan-Meier curves for different risk groups in the population based on an exemplary prognostic test, one can visualize the quality of the separation of risk of the exemplary clinical event. That is, more diverging risk groups indicate that a risk score is better at stratifying risky patients. This quality can be further quantized by means of a log-rank test, which calculates the probability (p-value) that two survival curves are equal taking into account the complete follow-up period.

The results of the risk scores using at least the inferred activity of the PI3K pathway and one or more of the Wnt pathway, the ER pathway, and the HH pathway, as presented herein, were benchmarked compared to the individual inferred activities $P_p$, $P_w$, $P_e$, and $P_h$, i.e., the inferred activities of the PI3K pathway, the Wnt pathway, the ER pathway, and the HH pathway, respectively, and as described herein, a non-linear combination of $P_e$, $P_w$, $P_h$, and the breast cancer Oncotype DX® test from Genomic Health. The non-linear combination of $P_e$, $P_w$, and $P_h$ is calculated as follows:

$$MPS_{ewh} = -P_e + \max(P_w, P_h). \quad (14)$$

The $MPS_{ewh}$ was shown to be a good predictor for recurrence in breast cancer patients. It was calculated using Eq. (14) and patients were stratified into low risk, intermediate risk and high risk patients using thresholds for the $MPS_{ewh}$ as described therein, i.e., at −0.1 and 0.1, respectively. The Oncotype DX® test was shown to be a good predictor for recurrence in ER positive breast cancer patients. The Oncotype DX® test returns a risk or recurrence score (RS) between 0 and 100, which is scaled here between 0 and 1 for direct comparison of the hazard ratios, that is calculated based on a combination of expression levels measured for a panel of genes (see S. Paik et al.: "A multi-gene assay to predict recurrence of Tamoxifen-treated, node-negative breast cancer", The New England Journal of Medicine, Vol. 351, No. 27, (2004), pages 2817 to 2826; C. Fan et al.: "Concordance among gene-expression-based predictors for breast cancer", The New England Journal of Medicine, Vol. 355, No. 6, (2006), pages 560 to 569). The RS is optimized with respect to 10-year survival in ER positive, HER2 negative (protein staining or FISH), node negative breast cancer patients. The RS was calculated using the microarray expression data reported in the mentioned datasets following the procedure reported by Fan et al. (see C. Fan et al. (2006)) and patients were subsequently divided into low risk, intermediate risk, and high risk patients according to the Oncotype DX® risk stratification algorithm (see S. Paik et al. (2004)).

At first Cox's proportional hazards regression was performed on the scaled risk scores using the breast cancer patients from E-MTAB365, GSE20685 and GSE21653. The calculated univariate Cox's coefficient, its standard error, hazard ratios, associated 95% confidence interval and p-value are shown in Table 15. Strikingly, all risk scores combining the activity of the PI3K pathway with the activity of one of the other cellular signaling pathways perform better than the individual pathway activities, as depicted by a higher modulus of the Cox's coefficients, which indicate that a combination of the activity of the PI3K pathway together with the activity of (an)other cellular signaling pathway(s) performed better than the individual pathway activities with respect to prognosis of a clinical event, in this case, disease free survival. In addition, the p-values of the combinations activities of two cellular signaling pathways also demonstrate this superiority as they are typically smaller for the combinations of the activity of the PI3K pathway with the activity of another cellular signaling pathway than those of the individual pathway activities. Combining the activity of the PI3K pathway with the activities of two other cellular signaling pathways also improved the Cox's coefficients (and p-values) compared to the risk scores based on two pathway activities. The $MPS_{pweh}$ risk score combining the activities of the PI3K pathway, the Wnt pathway, the ER pathway, and the HH pathway, as described in Eq. (12), performs best, better than the individual pathway activities as well as the combinations of the activity of the PI3K pathway with the activities of two or three cellular signaling pathways, as is visible in the coefficient, standard error, HR and p-value. In addition, the $MPS_{probesets}$ risk score including the same probesets as used in the $MPS_{pweh}$ score outperforms the risk scores including the activity of the PI3K pathway and the activity of one other cellular signaling pathway, as is evident from the Cox's regression results. Nevertheless, the performance of the $MPS_{probesets}$ is worse than the $MPS_{peh}$ and $MPS_{pweh}$, which is likely the result of 'overfitting' the risk score on the training data due to high amount of fitted coefficients (276 coefficients in $MPS_{probesets}$ vs. three and four coefficients in $MPS_{peh}$ and $MPS_{pweh}$, respectively). All risk scores that combine the activity of the PI3K pathway and the activities of one or more other pathways performed better than the $MPS_{ewh}$ and RS risk scores, as is evident from the respective Cox's coefficient.

TABLE 15

Results of Cox's proportional hazard regression on the combined test sets E-MTAB-365, GSE20685 and GSE21653. All risk scores are normalized for a direct comparison of the regression results. The Cox's coefficient calculated on the test set gives the "strength" (and direction) of the risk score with respect to survival. A high (absolute) value corresponds to a strong predictor. Hence, the "strength" is a quantification of the prognostic power of the risk score.

| Risk score | Cox's Coefficient | SE | HR | HR 95% CI | | p-value (Cox's regression) | p-value (log-rank) |
|---|---|---|---|---|---|---|---|
| $MPS_{pw}$ | 1.12 | 0.29 | 3.07 | 1.73 | 5.46 | 6.48e−05 | 6.1e−04 |
| $MPS_{pe}$ | 1.54 | 0.26 | 4.66 | 2.78 | 7.82 | 2.73e−09 | 9.2e−08 |
| $MPS_{ph}$ | 1.56 | 0.25 | 4.76 | 2.91 | 7.77 | 2.44e−10 | 1.4e−08 |
| $MPS_{pwe}$ | 1.74 | 0.32 | 5.72 | 3.05 | 10.71 | 2.60e−08 | 1.7e−09 |
| $MPS_{pwh}$ | 1.76 | 0.33 | 5.80 | 3.02 | 11.12 | 6.22e−08 | 5.4e−06 |
| $MPS_{peh}$ | 2.04 | 0.30 | 7.67 | 4.25 | 13.83 | 6.36e−12 | 2.4e−09 |
| $MPS_{pweh}$ | 2.20 | 0.35 | 9.02 | 4.54 | 17.92 | 1.72e−10 | 1.8e−09 |
| $MPS_{probesets}$ | 1.87 | 0.40 | 6.50 | 2.97 | 14.23 | 1.43e−06 | 1.5e−05 |
| $P_p$ | 0.82 | 0.18 | 2.26 | 1.58 | 3.24 | 4.17e−06 | 1.6e−04 |
| $P_w$ | 0.29 | 0.27 | 1.34 | 0.79 | 2.27 | 0.14 | 0.20 |
| $P_e$ | −0.81 | 0.19 | 0.44 | 0.30 | 0.65 | 1.48e−05 | 0.001 |
| $P_h$ | 0.92 | 0.21 | 2.52 | 1.66 | 3.81 | 6.11e−06 | 9.9e−05 |
| $MPS_{ewh}$ | 1.21 | 0.24 | 3.37 | 2.09 | 5.42 | 3.01e−07 | 3.0e−06 |
| RS | 1.00 | 0.16 | 2.71 | 2.00 | 3.67 | 7.59e−11 | 8.9e−10 |

Figure 2:
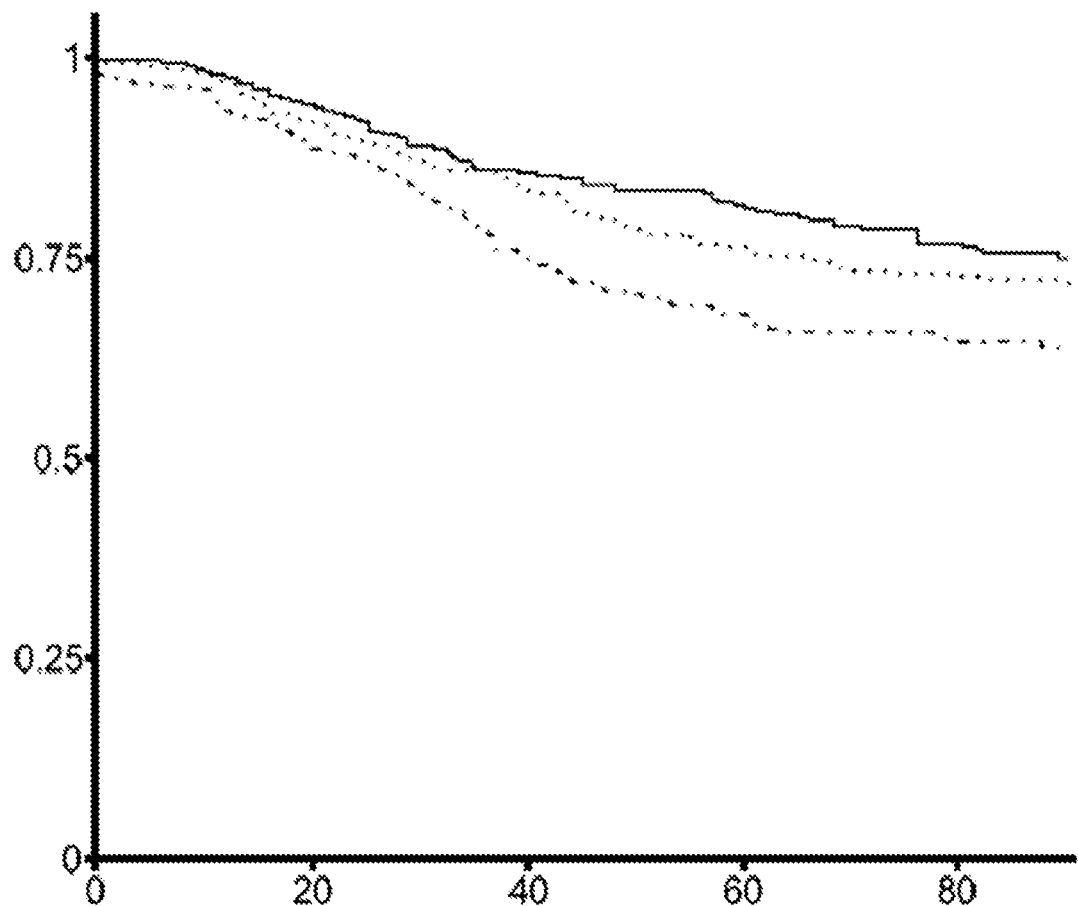
FIG. 2 shows a Kaplan-Meier plot of the disease free survival in breast cancer patients of E-MTAB-365, GSE20685 and GSE21653. The three patient groups are separated based on the tertiles of the $MPS_{pw}$ risk score, which is a combination of the calculated activities of the PI3K pathway and the Wnt pathway. The difference between the survival curves of the high and low risk patients is clearly significant (log-rank test: p=6.1e-4).
Figure 3:
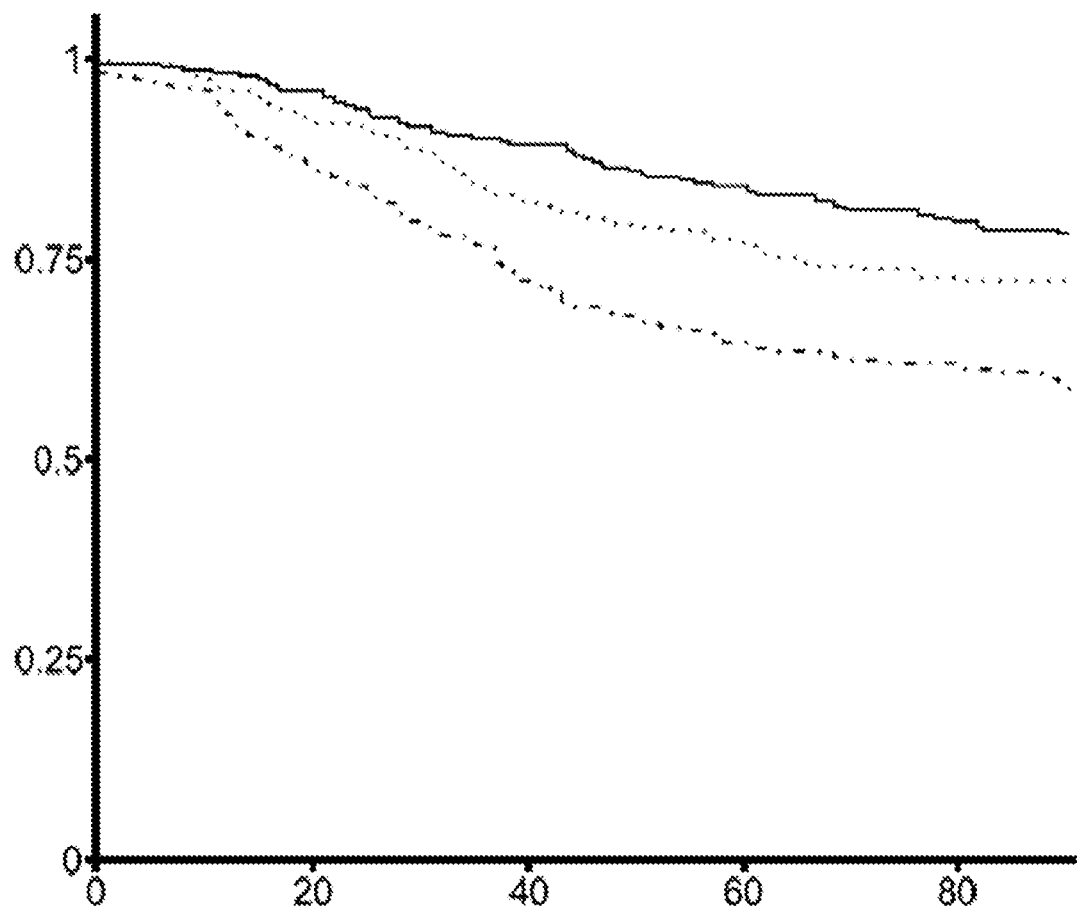
FIG. 3 shows a Kaplan-Meier plot of the disease free survival in breast cancer patients of E-MTAB-365, GSE20685 and GSE21653. The three patients groups are separated based on the tertiles of the $MPS_{pe}$ risk score, which is a combination of the inferred activities of the PI3K pathway and the HH pathway. The difference between the survival curves of the high and low risk patients is clearly significant (log-rank test: p=9.2e-8).
Figure 4:
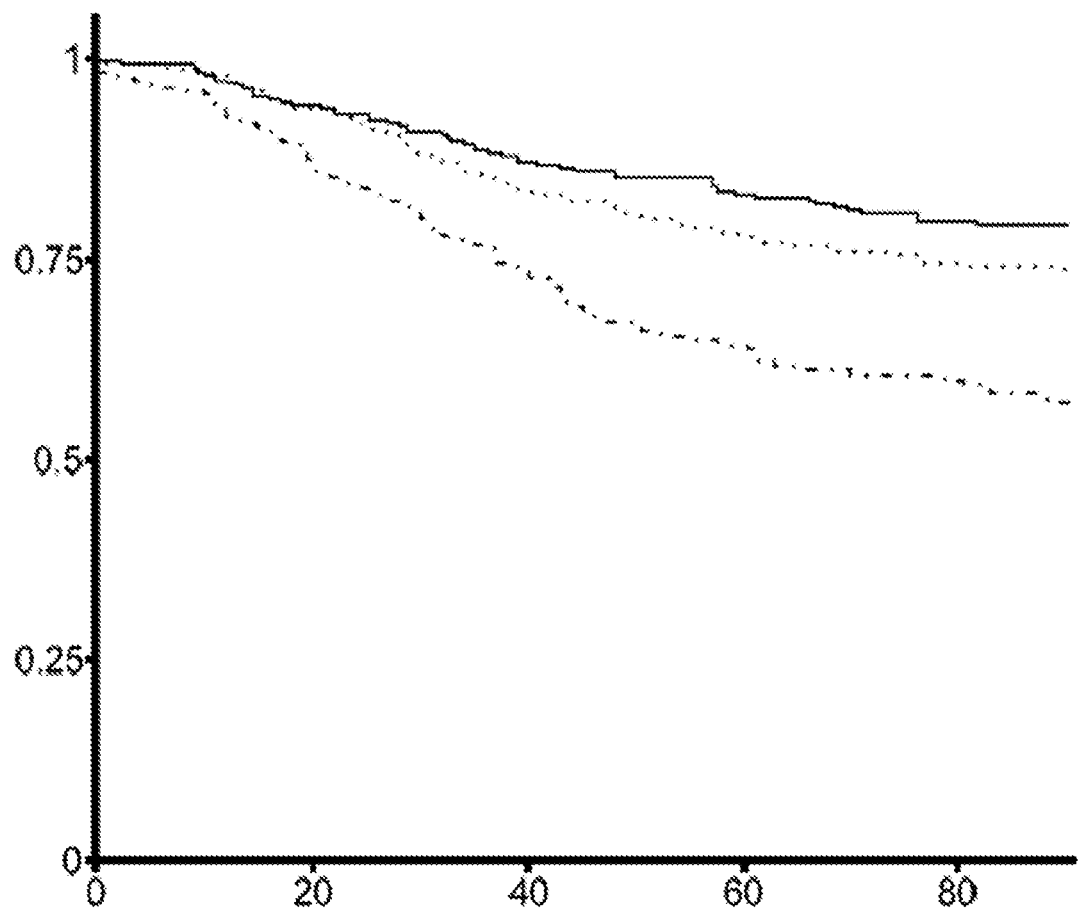
FIG. 4 shows a Kaplan-Meier plot of the disease free survival in breast cancer patients of E-MTAB-365, GSE20685 and GSE21653. The three patient groups are separated based on the tertiles of the $MPS_{ph}$ risk score, which is a combination of the inferred activities of the PI3K pathway and the HH pathway. The difference between the survival curves of the high and low risk patients is clearly significant (log-rank test: p=1.4e-8).
Figure 5:
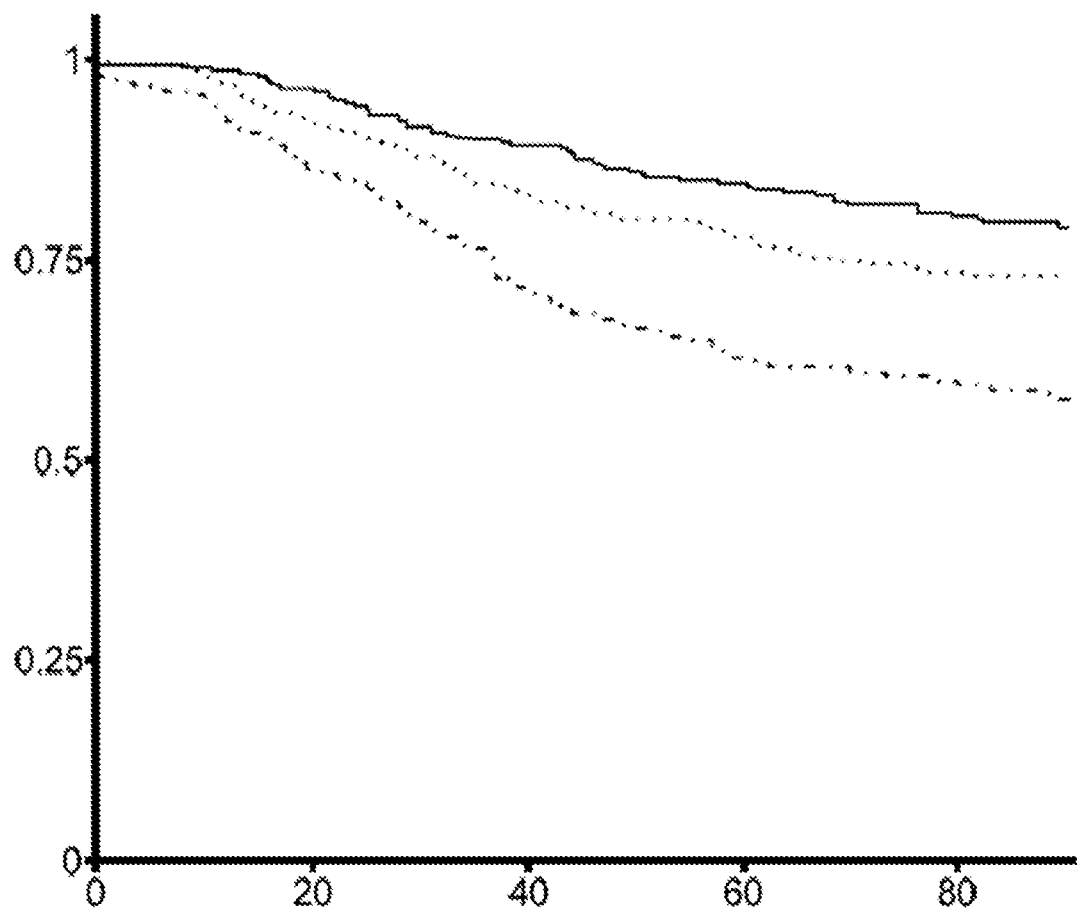
FIG. 5 shows a Kaplan-Meier plot of the disease free survival in breast cancer patients of E-MTAB-365, GSE20685 and GSE21653. The three patient groups are separated based on the tertiles of the $MPS_{pwe}$ risk score, which is a combination of the inferred activities of the PI3K pathway, the Wnt pathway, and the ER pathway. The difference between the survival curves of the high and low risk patients is clearly significant (log-rank test: p=1.7e-9).
Figure 6:
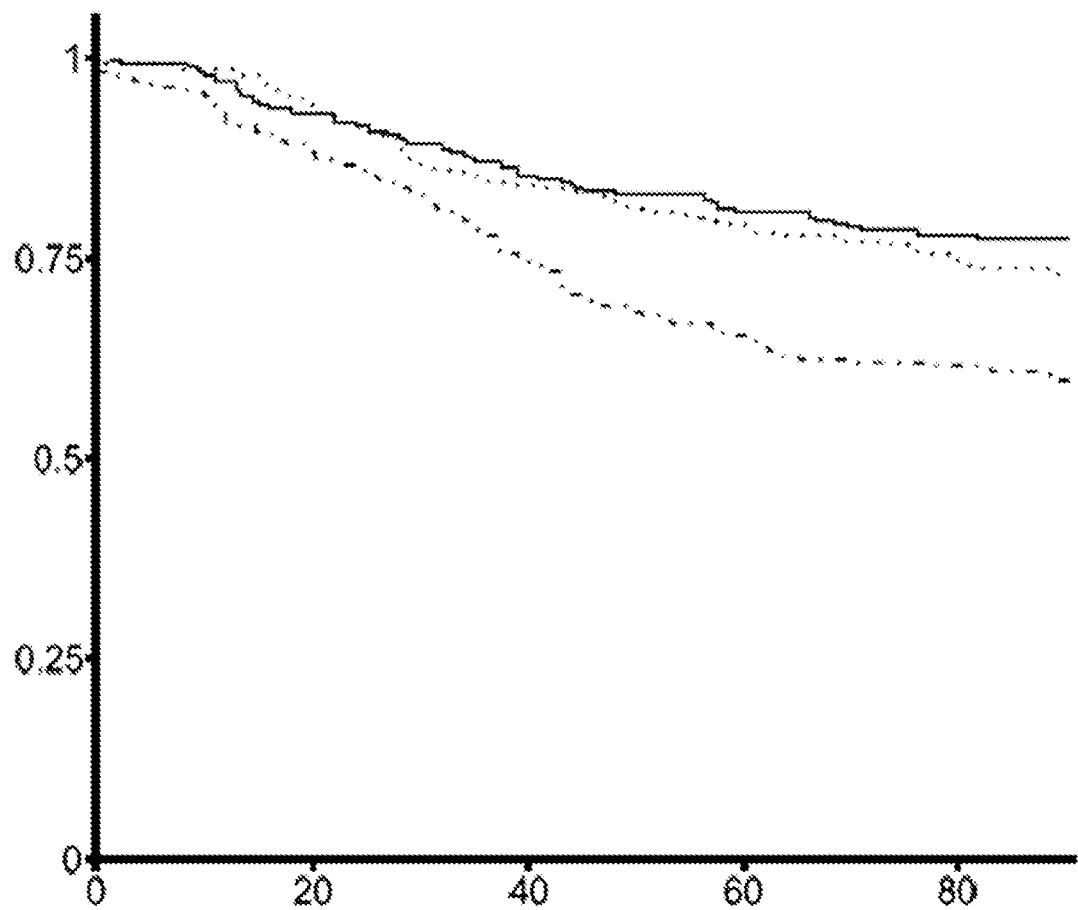
FIG. 6 shows a Kaplan-Meier plot of the disease free survival in breast cancer patients of E-MTAB-365, GSE20685 and GSE21653. The three patient groups are separated based on the tertiles of the $MPS_{pwh}$ risk score, which is a combination of the inferred activities of the PI3K pathway, the Wnt pathway, and the HH pathway. The difference between the survival curves of the high and low risk patients is clearly significant (log-rank test: p=5.4e-6).
Figure 7:
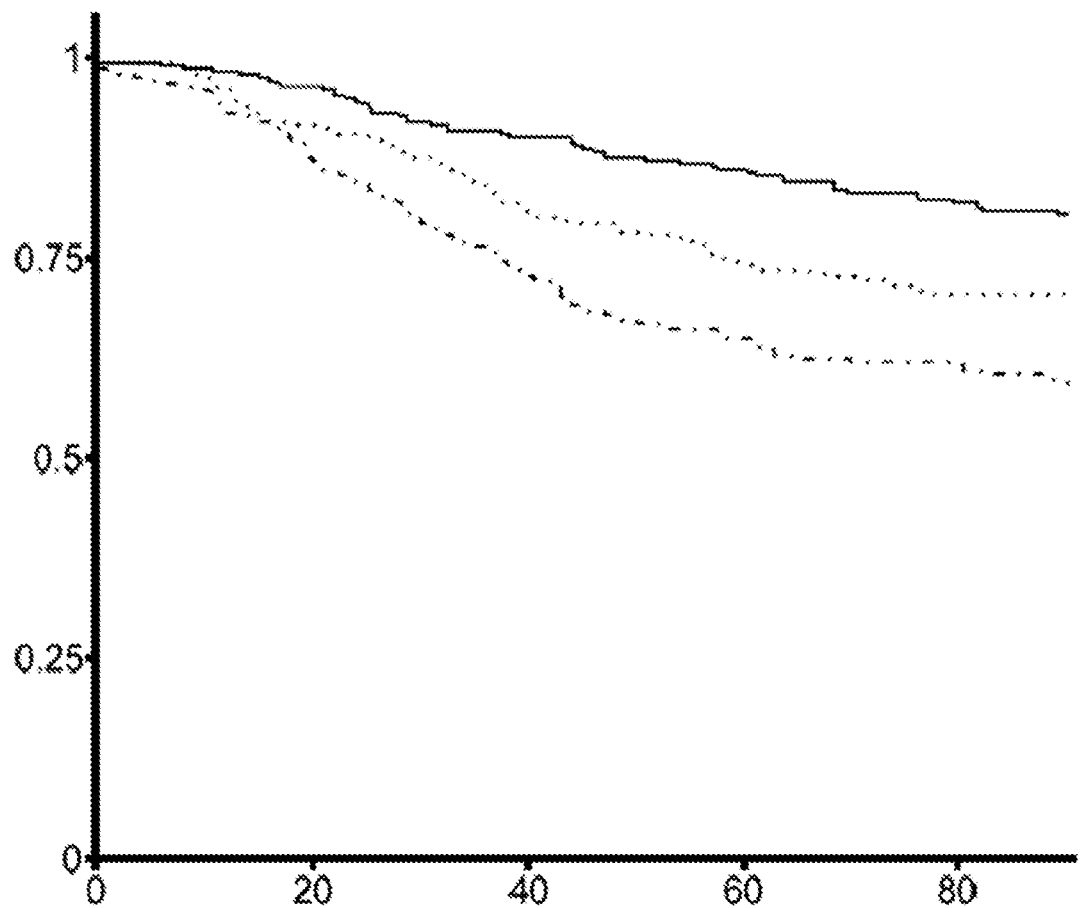
FIG. 7 shows a Kaplan-Meier plot of the disease free survival in breast cancer patients of E-MTAB-365, GSE20685 and GSE21653. The three patient groups are separated based on the tertiles of the $MPS_{peh}$ risk score, which is a combination of the inferred activities of the PI3K pathway, the ER pathway, and the HH pathway. The difference between the survival curves of the high and low risk patients is clearly significant (log-rank test: p=2.4e-9).
Figure 8:
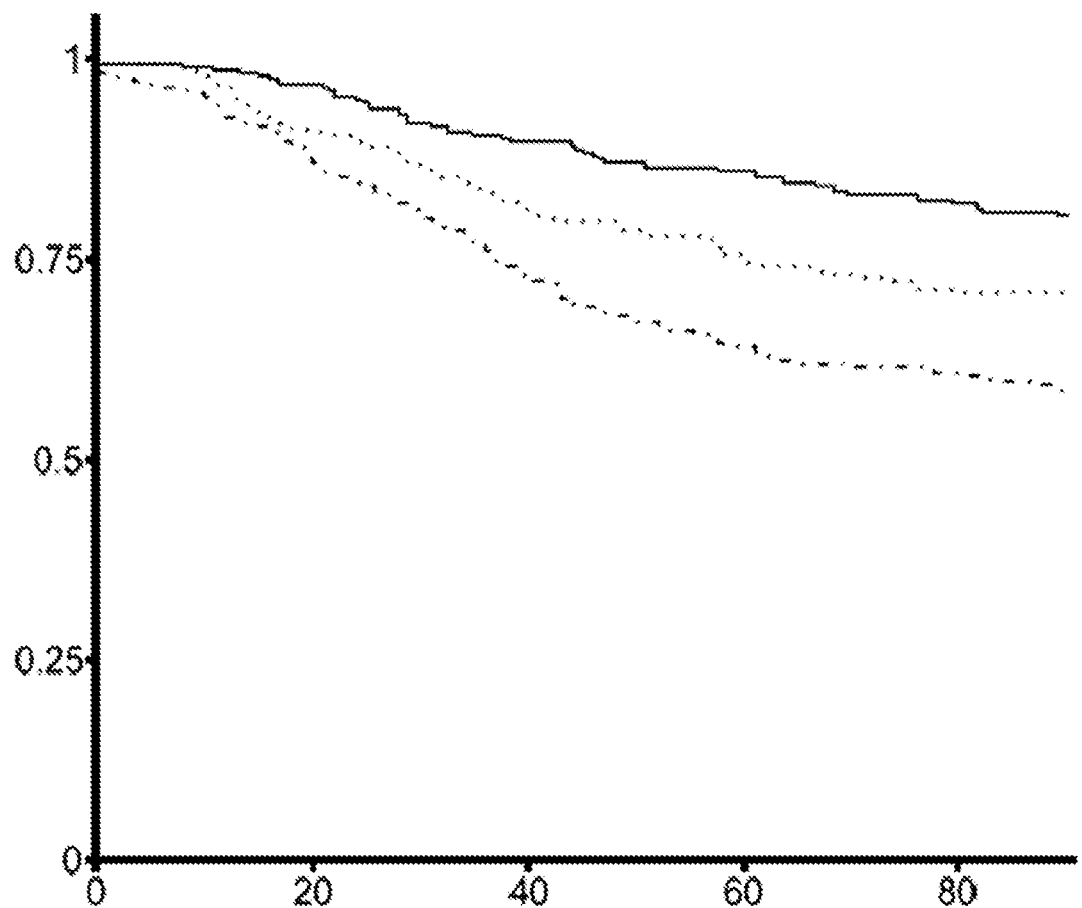
FIG. 8 shows a Kaplan-Meier plot of the disease free survival in breast cancer patients of E-MTAB-365, GSE20685 and GSE21653. The three patient groups are separated based on the tertiles of the $MPS_{pweh}$ risk score, which is a combination of the inferred activities of the PI3K pathway, the Wnt pathway, the ER pathway, and the HH pathway. The difference between the survival curves of the high and low risk patients is clearly significant (log-rank test: p=1.8e-9).
Figure 9:
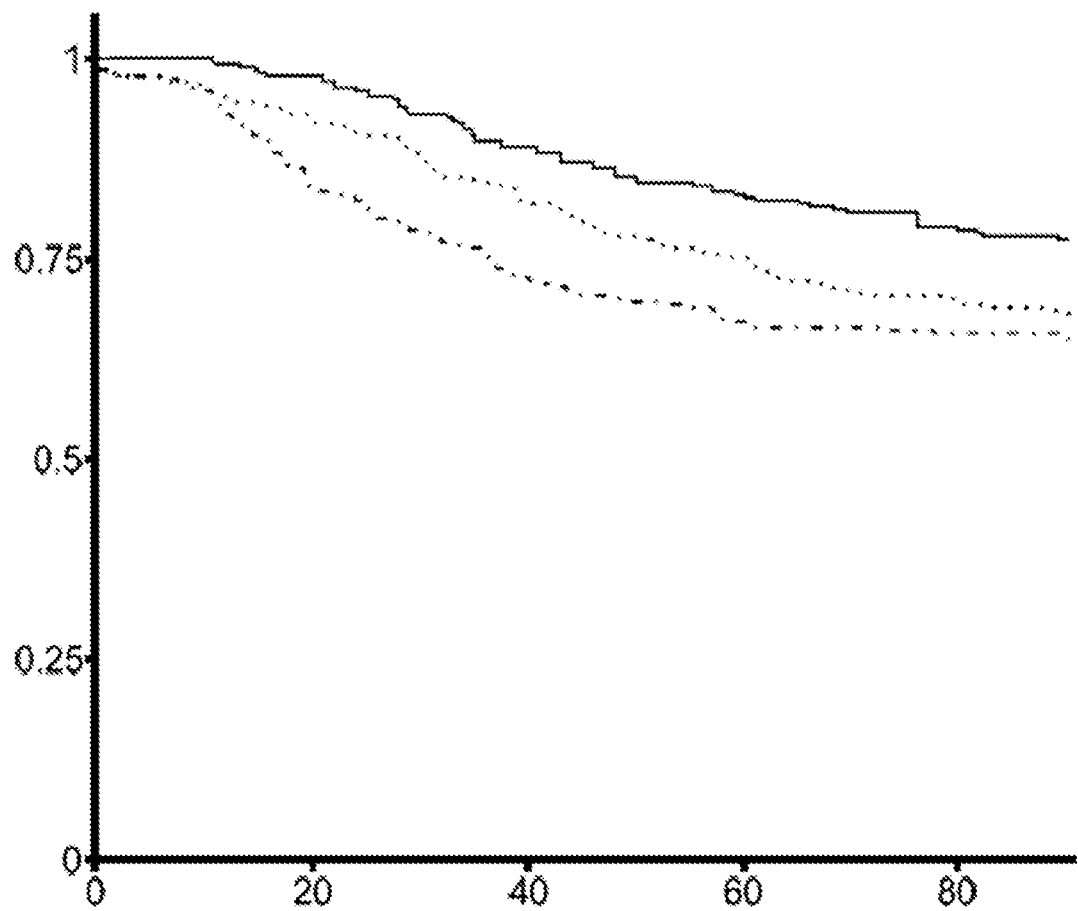
FIG. 9 shows a Kaplan-Meier plot of the disease free survival in breast cancer patients of E-MTAB-365, GSE20685 and GSE21653. The three patient groups are separated based on the tertiles of the $MPS_{probesets}$ risk score, which is a combination of the probesets associated with the selected target genes of the PI3K pathway, the Wnt pathway, the ER pathway, and the HH pathway. The difference between the survival curves of the high and low risk patients is clearly significant (log-rank test: p=3.0e-6).

Next the prognostic stratification of the risk scores of interests were analyzed using Kaplan-Meier plots in combination with the log-rank test. A simplistic algorithm is exemplarily used for the new risk scores described herein to stratify patients according to their risk score. The 1005 patients are divided into three equally sized groups (n=335) of increasing risk scores, i.e. the cutoffs are at the tertiles of the respective risk scores of all patients. Other variations of the risk stratification to the aforementioned method can be understood and effected by those skilled in the art using known optimization techniques. For example the Youden's J statistics can be used to infer risk thresholds. The risk stratification of the other risk scores included for comparison are performed as described by their inventors. That is, the activities of the PI3K pathway, the Wnt pathway, the ER pathway, and the HH pathway are used to stratify patients according to whether the respective pathway is either active, i.e., an activity of more than 0.5 on a scale from 0 to 1, or passive, i.e., an activity of 0.5 or less on a scale from 0 to 1. Patients with an $MPS_{ewh}$ of −0.1 or less are considered to be at low risk, patients with an $MPS_{ewh}$ higher or equal to 0.1 are considered to be at high risk, and all remaining patients (with an $MPS_{ewh}$ between −0.1 and 0.1) are considered to be at intermediate risk. On the other hand, patients with an RS less than 18 are considered to be at low risk, patients with an RS of 31 or higher are considered to be at high risk, and all remaining patients (with a RS between 18 and 31) are considered to be at intermediate risk. Kaplan-Meier plots are provided in FIG. 2 to 9 for the new risk scores as described herein, that is, $MPS_{pw}$ (see FIG. 2), $MPS_{pe}$ (see FIG. 3), $MPS_{ph}$ (see FIG. 4), $MPS_{pwe}$ (see FIG. 5), $MPS_{pwh}$ (see FIG. 6), $MPS_{peh}$ (see FIG. 7), $MPS_{pweh}$ (see FIG. 8) and $MPS_{probesets}$ (see FIG. 9). In these graphs, the vertical axis indicates the recurrence free survival as a fraction of the patient group and the horizontal axis indicates a time in years. The low, intermediate and high risk groups (each including 335 patients) are illustrated with a solid line (characteristically the upper line), a dotted line (characteristically the middle line), and a dashed-dotted line (characteristically the lower line), respectively. These plots show a clear discrimination of the risk that a subject might experience a clinical event within a certain period of time between the different groups. This difference in risk stratification can be quantized by means of the log-rank test. Here it was chosen to compare the Kaplan-Meier curve of the highest risk group vs. the lowest risk group (in case of the individual pathway activities this is active vs. passive). The log-rank p-values are depicted in the last column of Table 15. The Kaplan-Meier plots and associated log-rank statistics further exemplify the advantage of the risk scores including the activity of the PI3K pathway and the activity of one further cellular signaling pathway, as they can be used to stratify patients at lower or higher risk of disease recurrence.

Figure 10:
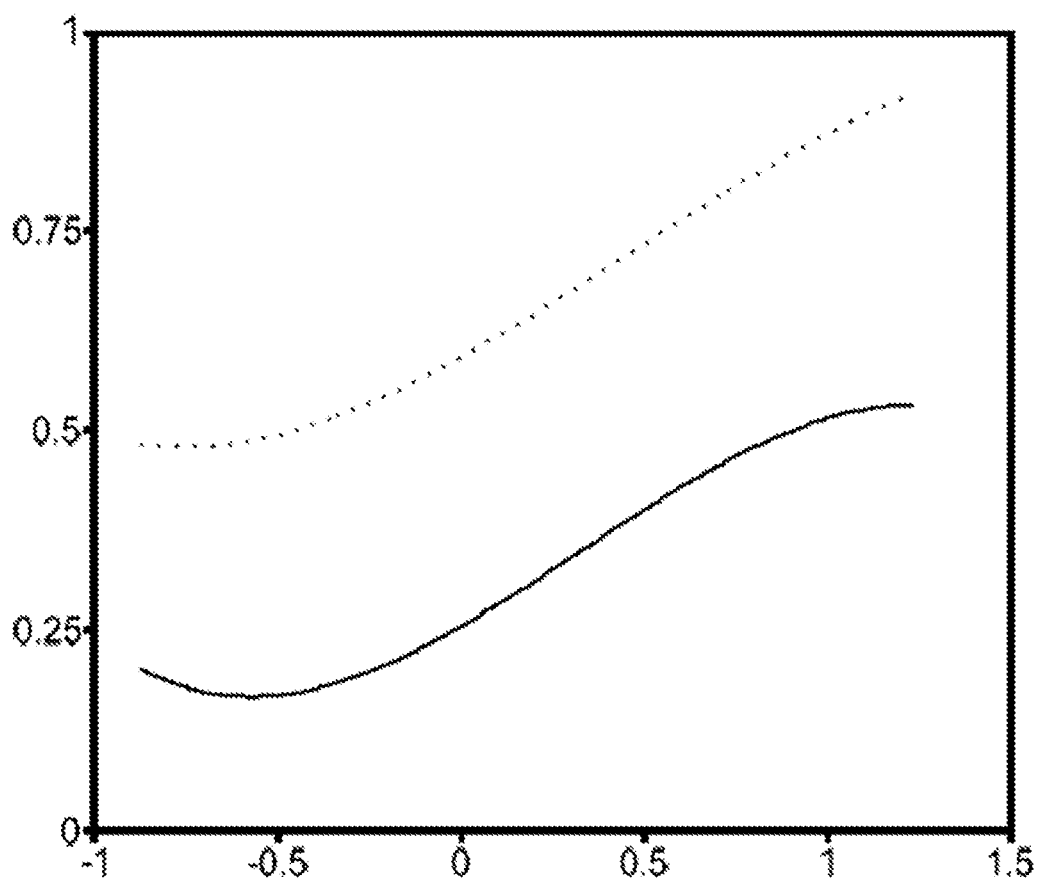
FIG. 10 shows the likelihood of disease free survival at five (lower, solid line) and ten years (upper, dotted lines) using the unscaled $MPS_{pweh}$ as example.

FIG. 10 shows the likelihood of disease free survival at five (solid line) and ten years (dotted lines) using the unscaled $MPS_{pweh}$ as example. The piecewise curve shows a strong (monotonic) increase in likelihood/risk of disease recurrence for value above −0.5, below this value the risk seems to level off, hence it would make sense to place cutoffs near this value. Furthermore, for ease of use of the user the multi-pathway scores could be rescaled to start at zero and range up to a certain positive number, e.g. a score between 0 and 15 or 0 and 100, instead of covering a range including negative values. For example a rescaled $MPS_{pweh}$ including these thresholds could look like this:

$$MPS_{pweh}^{sc} = \begin{cases} 0 & 60\,(MPS_{pweh} + 0.5) < 0 \\ 60\,(MPS_{pweh} + 0.5) & 0 \leq 60\,(MPS_{pweh} + 0.5) \leq 100 \\ 100 & 60\,(MPS_{pweh} + 0.5) > 100 \end{cases} \quad (15)$$

The $MPS_{pw}$, $MPS_{pe}$, $MPS_{ph}$, $MPS_{pweh}$ and $MPS_{probesets}$ risk scores trained on the initial training set of breast cancer patients in GSE6532 and GSE9195 were shown to generalize well on other datasets of breast cancer samples. Alternatively, the risk scores can be trained on the previously described datasets, i.e., GSE6532, GSE9195, E-MTAB-365, GSE20685 and GSE21653 simultaneously (in total 1169 patients with survival data) using the estimated Cox's coefficients as discussed previously. This results in the following risk scores:

$$MPS_{pw} = 0.70(\pm 0.17) \cdot P_p + 0.38(\pm 0.26) \cdot P_w \quad (16)$$

$$MPS_{pe} = 0.70(\pm 0.17) \cdot P_p + (-0.87(\pm 0.18)) \cdot P_e \quad (17)$$

$$MPS_{ph} = 0.70(\pm 0.17) \cdot P_p + 0.90(\pm 0.20) \cdot P_h \quad (18)$$

$$MPS_{pwe} = 0.70(\pm 0.17) \cdot P_p + 0.38(\pm 0.26) \cdot P_w + (-0.87(\pm 0.18)) \cdot P_e \quad (19)$$

$$MPS_{pwh} = 0.70(\pm 0.17) \cdot P_p + 0.38(\pm 0.26) \cdot P_w + 0.90(\pm 0.20) \cdot P_h \quad (20)$$

$$MPS_{peh} = 0.70(\pm 0.17) \cdot P_p + (-0.87(\pm 0.18)) \cdot P_e + 0.90(\pm 0.20) \cdot P_h \quad (21)$$

$$MPS_{pweh} = 0.70(\pm 0.17) \cdot P_p + 0.38(\pm 0.26) \cdot P_w + (-0.87(\pm 0.18)) \cdot P_e + 0.90(\pm 0.20) \cdot P_h \quad (22)$$

Alternatively, the coefficients of the risk scores can be determined by combining the Cox's coefficients estimated on the datasets independently. The independently determined Cox's coefficients together with their standard error are used to estimate the true coefficient for the activity of each pathway using maximum likelihood estimation. The patients of both datasets from the Guy's hospital, GSE6532 and GSE9195, were combined into one training dataset due to their small size. The most likely coefficients' values were determined by weighting the individually determined coefficient estimates with the number of patients included in the dataset over the standard error of the coefficient estimate:

$$\arg\min_{\hat{b}} \sum_{i \in datasets} n_i \left(\frac{\hat{b} - b_i}{\sigma_i}\right)^2 \quad (23)$$

wherein $n_i$ is the number of patients included in dataset i, $\hat{b}$ is the estimator of the true coefficient value, $b_i$ is the Cox's coefficient of dataset i, and $\sigma_i$ is the standard error of the Cox's coefficient estimated from dataset i. This minimization was performed for the activity of the PI3K pathway, the Wnt pathway, the ER pathway, and the HH pathway, respectively. The variances of the true coefficient estimates were determined using the Fisher information matrix. Using these values to parameterize the aforementioned linear combinations of pathway activities result in the following risk scores:

$$MPS_{pw} = 0.65(\pm 0.09) \cdot P_p + 0.12(\pm 0.09) \cdot P_w \quad (24)$$

$$MPS_{pe} = 0.65(\pm 0.09) \cdot P_p + (-0.85(\pm 0.06)) \cdot P_e \quad (25)$$

$$MPS_{ph} = 0.65(\pm 0.09) \cdot P_p + 0.68(\pm 0.16) \cdot P_h \quad (26)$$

$$MPS_{pwe} = 0.65(\pm 0.09) \cdot P_p + 0.12(\pm 0.09) \cdot P_w + (-0.85(\pm 0.06)) \cdot P_e \quad (27)$$

$$MPS_{pwh} = 0.65(\pm 0.09) \cdot P_p + 0.12(\pm 0.09) \cdot P_w + 0.68(\pm 0.16) \cdot P_h \quad (28)$$

$$MPS_{pwh} = 0.65(\pm 0.09) \cdot P_p + (-0.85(\pm 0.06)) \cdot P_e + 0.68(\pm 0.16) \cdot P_h \quad (29)$$

$$MPS_{pweh} = 0.65(\pm 0.09) \cdot P_p + 0.12(\pm 0.09) \cdot P_w + (-0.85(\pm 0.06)) \cdot P_e + 0.68(\pm 0.16) \cdot P_h \quad (30)$$

Example 3: CDS Application

With reference to FIG. 11 (diagrammatically showing a clinical decision support (CDS) system configured to determine a risk score that indicates a risk that a subject will experience a clinical event within a certain period of time, as disclosed herein), a clinical decision support (CDS) system 10 is implemented as a suitably configured computer 12. The computer 12a may be configured to operate as the CDS system 10 by executing suitable software, firmware, or other instructions stored on a non-transitory storage medium (not shown), such as a hard drive or other magnetic storage medium, an optical disk or another optical storage medium, a random access memory (RAM), a read-only memory (ROM), a flash memory, or another electronic storage medium, a network server, or so forth. While the illustrative CDS system 10 is embodied by the illustrative computer 12a, more generally the CDS system may be embodied by a digital processing device or an apparatus comprising a digital processor configured to perform clinical decision support methods as set forth herein. For example, the digital processing device may be a handheld device (e.g., a personal data assistant or smartphone running a CDS application), a notebook computer, a desktop computer, a tablet computer or device, a remote network server, or so forth. The computer 12a or other digital processing device typically includes or is operatively connected with a display device 14a via which information including clinical decision support recommendations are displayed to medical personnel. The computer 12a or other digital processing device typically also includes or is operatively connected with one or more user input devices, such as an illustrative keyboard 16a, or a mouse, a trackball, a trackpad, a touch-sensitive screen (possibly integrated with the display device 14a), or another pointer-based user input device, via which medical personnel can input information such as operational commands for controlling the CDS system 10, data for use by the CDS system 10, or so forth.

The CDS system 10 receives as input information pertaining to a subject (e.g., a hospital patient, or an outpatient being treated by an oncologist, physician, or other medical personnel, or a person undergoing cancer screening or some other medical diagnosis who is known or suspected to have a certain type of cancer, such as colon cancer, breast cancer, or liver cancer, or so forth). The CDS system 10 applies various data analysis algorithms to this input information in order to generate clinical decision support recommendations that are presented to medical personnel via the display device 14a (or via a voice synthesizer or other device providing human-perceptible output). In some embodiments, these algorithms may include applying a clinical guideline to the patient. A clinical guideline is a stored set of standard or "canonical" treatment recommendations, typically constructed based on recommendations of a panel of medical experts and optionally formatted in the form of a clinical "flowchart" to facilitate navigating through the clinical guideline. In various embodiments the data processing algorithms of the CDS 10 may additionally or alternatively include various diagnostic or clinical test algorithms that are performed on input information to extract clinical decision recommendations, such as machine learning methods disclosed herein.

In the illustrative CDS systems disclosed herein (e.g., CDS system 10), the CDS data analysis algorithms include one or more diagnostic or clinical test algorithms that are performed on input genomic and/or proteomic information acquired by one or more medical laboratories 18a. These laboratories may be variously located "on-site", that is, at the hospital or other location where the subject is undergoing medical examination and/or treatment, or "off-site", e.g., a specialized and centralized laboratory that receives (via mail or another delivery service) a sample of the subject that has been extracted from the subject (e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure). The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, the body fluid of which a sample is extracted may be urine, gastrointestinal contents, or an extravasate.

The sample is processed by the laboratory to generate genomic or proteomic information. For example, the sample may be processed using a microarray (also variously referred to in the art as a gene chip, DNA chip, biochip, or so forth) or by quantitative polymerase chain reaction (qPCR) processing to measure probative genomic or proteomic information such as expression levels of genes of interest, for example in the form of a level of messenger ribonucleic acid (mRNA) that is transcribed from the gene, or a level of a protein that is translated from the mRNA transcribed from the gene. As another example, the sample may be processed by a gene sequencing laboratory to generate sequences for deoxyribonucleic acid (DNA), or to generate an RNA sequence, copy number variation, methylation, or so forth. Other contemplated measurement approaches include immunohistochemistry (IHC), cytology, fluorescence in situ hybridization (FISH), proximity ligation assay or so forth, performed on a pathology slide. Other information that can be generated by microarray processing, mass spectrometry, gene sequencing, or other laboratory techniques includes methylation information. Various combinations of such genomic and/or proteomic measurements may also be performed.

In some embodiments, the medical laboratories 18a perform a number of standardized data acquisitions on the sample of the subject, so as to generate a large quantity of genomic and/or proteomic data. For example, the standardized data acquisition techniques may generate an (optionally aligned) DNA sequence for one or more chromosomes or chromosome portions, or for the entire genome. Applying a standard microarray can generate thousands or tens of thousands of data items such as expression levels for a large number of genes, various methylation data, and so forth. Similarly, PCR-based measurements can be used to measure the expression level of a selection of genes. This plethora of genomic and/or proteomic data, or selected portions thereof, are input to the CDS system 10 to be processed so as to develop clinically useful information for formulating clinical decision support recommendations.

The disclosed CDS systems and related methods relate to processing of genomic and/or proteomic data to assess activity of various cellular signaling pathways and to determine a risk score that indicates a risk that a subject will experience a clinical event (e.g., cancer) within a certain period of time. However, it is to be understood that the disclosed CDS systems (e.g., CDS system 10) may optionally further include diverse additional capabilities, such as generating clinical decision support recommendations in accordance with stored clinical guidelines based on various patient data such as vital sign monitoring data, patient history data, patient demographic data (e.g., gender, age, or so forth), patient medical imaging data, or so forth. Alternatively, in some embodiments the capabilities of the CDS system 10 may be limited to only performing genomic and/or proteomic data analyses to assess the activity of cellular signaling pathways and to determine a risk score that indicates a risk that a subject will experience a clinical event (e.g., cancer) within a certain period of time, as disclosed herein.

With continuing reference to exemplary FIG. 11, the CDS system 10 infers activity 22 of one or more cellular signaling pathways, here, the PI3K pathway and one or more of the Wnt pathway, the ER pathway, and the HH pathway, in the subject based at least on, but not restricted to, the expression levels 20a of one or more target gene(s) of the cellular signaling pathways measured in the sample of the subject. The PI3K pathway, the Wnt pathway, the ER pathway, and the HH pathway are of interest in various areas of oncology because loss of regulation of these pathways can be a cause of proliferation of a cancer. There are about 10 to 15 relevant signaling pathways, and each cancer is driven by at least one dominant pathway being deregulated. Without being limited to any particular theory of operation these pathways regulate cell proliferation, and consequentially a loss of regulation of these pathways in cancer cells can lead to the pathway being "always on" thus accelerating the proliferation of cancer cells, which in turn manifests as a growth, invasion or metastasis (spread) of the cancer.

Measurement of mRNA expression levels of genes that encode for regulatory proteins of the cellular signaling pathway, such as an intermediate protein that is part of a protein cascade forming the cellular signaling pathway, is an indirect measure of the regulatory protein expression level and may or may not correlate strongly with the actual regulatory protein expression level (much less with the overall activity of the cellular signaling pathway). The cellular signaling pathway directly regulates the transcription of the target genes—hence, the expression levels of mRNA transcribed from the target genes is a direct result of this regulatory activity. Hence, the CDS system 10 infers activity of the one or more cellular signaling pathways (here, the PI3K pathway and one or more of the Wnt pathway, the ER pathway, and the HH pathway) based at least on expression levels of one or more target gene(s) (mRNA or protein level as a surrogate measurement) of the cellular signaling pathways. This ensures that the CDS system 10 infers the activity of the pathway based on direct information provided by the measured expression levels of the target gene(s).

The inferred activities, in this example, $P_p$, $P_w$, $P_e$, and $P_h$, i.e., the inferred activities of the PI3K pathway, the Wnt pathway, the ER pathway, and the HH pathway, are then used to determine 24 a risk score that indicates a risk that the subject will experience the clinical event, in this example, cancer, in particular, breast cancer, within a certain period of time, as described in detail herein. The risk score is based at least in part on a combination of the inferred activities. For example, the risk score may be the "Multi-Pathway Score" (MPS) calculated as described in detail with reference to Eq. (4) or (5).

Based on the determined MPS, the CDS system 10, in this example, assigns 26 the subject to at least one of a plurality of risk groups associated with different indicated risks that the subject will experience the clinical event within the certain period of time, and/or decides 28 a treatment recommended for the subject based at least in part on the indicated risk that the subject will experience the clinical event within the certain period of time.

Determining the MPS and/or the risk classification for a particular patient by the CDS system or a standalone implementation of the MPS and risk classification as described herein will enable the oncologist, physician, or other medical personnel involved in diagnosis or treatment or monitoring/follow-up of the patient to tailor the treatment such that the patient has the best chance of long term survival while unwanted side-effects, especially those of aggressive chemotherapy and/or targeted therapy and/or immunotherapy and/or radiotherapy and/or surgery, are minimized. Thus, e.g., patients with a low risk of cancer recurrence, i.e., those with a low MPS and/or those classified as low risk based on the risk stratification algorithm as described herein, are currently typically treated with hormonal treatment alone or a combination of hormonal treatment, for example anti-estrogen and/or aromatase inhibitors, and a less toxic chemotherapeutic agent. On the other hand, patients with an intermediate or high risk of cancer recurrence, i.e., those with a medium to high MPS and/or those classified as intermediate or high risk based on the risk stratification algorithm as described herein, will currently typically be treated with more aggressive chemotherapy, such as anthracycline and/or taxane-based treatment regimes. In addition, the MPS, possibly in combination with other patient's test results and/or results from other prognostic or predictive (e.g., companion diagnostic) tests, can give rise to a decision to treat the patient with targeted drugs such as Tamoxifen, Trastuzumab, Bevacizumab, and/or other therapeutic drugs (for example immunotherapy) that are currently not part of the main line treatment protocol for the patient's particular cancer, and/or other treatment options, such as radiation therapy, for example brachytherapy, and/or different timings for treatment, for example before and/or after primary treatment.

It is noted that instead of directly using the determined risk score (MPS) as an indication of the risk that the subject will experience a clinical event (e.g., cancer) within the certain period of time, it is possible that the CDS system 10 is configured to combine the risk score with one or more additional risk scores obtained from one or more additional prognostic tests to obtain a combined risk score, wherein the combined risk score indicates a risk that the subject will experience the clinical event within the certain period of time. The one or more additional prognostic tests may comprise, in particular, the Oncotype DX® breast cancer test, the Mammostrat® breast cancer test, the MammaPrint® breast cancer test, the EndoPredict® breast cancer test, the BluePrint™ breast cancer test, the CompanDx® breast cancer test, the Breast Cancer Index$^{SM}$ (HOXB13/IL17BR), the OncotypeDX® colon cancer test, and/or a proliferation test performed by measuring expression of gene/protein Ki67.

Example 4: A Kit and Analysis Tools to Determine a Risk Score

The set of target genes which are found to best indicate the activity of the respective cellular signaling pathway, based on microarray/RNA sequencing based investigation using, e.g., the Bayesian model or the (pseudo-)linear model, can be translated into for example a multiplex quantitative PCR assay or dedicated microarray biochips to be performed on a sample of a subject. A selection of the gene sequence as described herein can be used to select for example a primer-probe set for RT-PCR or oligonucleotides for microarray development. To develop such an FDA-approved test for pathway activity and risk score determination, development of a standardized test kit is required, which needs to be clinically validated in clinical trials to obtain regulatory approval.

This application describes several embodiments. Modifications and alterations may occur to others upon reading and understanding the preceding detailed description. It is intended that the application is construed as including all such modifications and alterations insofar as they come within the scope of the appended claims or the equivalents thereof.

Other variations to the disclosed embodiments can be understood and effected by those skilled in the art in practicing the claims, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the determination of the risk score performed by one or several units or devices can be performed by any other number of units or devices.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

This specification has been described with reference to embodiments, which are illustrated by the accompanying Examples. The disclosure can, however, be embodied in different forms and should not be construed as limited to the embodiments set forth herein.

Given the teaching herein, one of ordinary skill in the art will be able to modify the disclosure for a desired purpose and such variations are considered within the scope of the disclosure.

Example 5: Sequence Listings Used in Application

Sequence Listing:

| Seq. No. | Gene: |
|---|---|
| Seq. 1 | ADRA2C |
| Seq. 2 | AGRP |
| Seq. 3 | AP1B1 |
| Seq. 4 | ASCL2 |
| Seq. 5 | ATG14 |
| Seq. 6 | ATP5J |
| Seq. 7 | ATP8A1 |
| Seq. 8 | AXIN2 |
| Seq. 9 | BCL2 |
| Seq. 10 | BCL2L11 |
| Seq. 11 | BCL6 |
| Seq. 12 | BIRC5 |
| Seq. 13 | BMP7 |
| Seq. 14 | BNIP3 |
| Seq. 15 | BTG1 |
| Seq. 16 | C10orf10 |
| Seq. 17 | CA12 |
| Seq. 18 | CAT |
| Seq. 19 | CAV1 |
| Seq. 20 | CBLB |
| Seq. 21 | CCND1 |
| Seq. 22 | CCND2 |
| Seq. 23 | CCNG2 |
| Seq. 24 | CD44 |
| Seq. 25 | CDH26 |
| Seq. 26 | CDKN1A |
| Seq. 27 | CDKN1B |
| Seq. 28 | CELSR2 |
| Seq. 29 | CFLAR |
| Seq. 30 | COL18A1 |
| Seq. 31 | COX7A2L |
| Seq. 32 | CTSD |
| Seq. 33 | CTSL |
| Seq. 34 | DDB1 |
| Seq. 35 | DEFA6 |
| Seq. 36 | DKK1 |
| Seq. 37 | DSCAM |
| Seq. 38 | DYRK2 |
| Seq. 39 | EBAG9 |
| Seq. 40 | EPHB2 |
| Seq. 41 | EPHB3 |
| Seq. 42 | ERBB2 |
| Seq. 43 | ERBB3 |
| Seq. 44 | EREG |
| Seq. 45 | ESR1 |
| Seq. 46 | EXT1 |
| Seq. 47 | FASLG |
| Seq. 48 | FAT1 |
| Seq. 49 | FBXO32 |
| Seq. 50 | FGFR2 |
| Seq. 51 | FOXA2 |
| Seq. 52 | FOXF1 |
| Seq. 53 | FOXL1 |
| Seq. 54 | FOXM1 |
| Seq. 55 | FST |
| Seq. 56 | FYN |
| Seq. 57 | FZD7 |
| Seq. 58 | GADD45A |
| Seq. 59 | GLI1 |
| Seq. 60 | GLI3 |
| Seq. 61 | GLUL |
| Seq. 62 | GREB1 |
| Seq. 63 | H19 |
| Seq. 64 | HHIP |
| Seq. 65 | HNF1A |
| Seq. 66 | HSPB1 |
| Seq. 67 | IGF1R |
| Seq. 68 | IGFBP1 |
| Seq. 69 | IGFBP3 |
| Seq. 70 | IGFBP4 |
| Seq. 71 | IGFBP6 |
| Seq. 72 | IL1R2 |
| Seq. 73 | IL8 (CXCL8) |
| Seq. 74 | INSR |
| Seq. 75 | JAG2 |
| Seq. 76 | JUP |
| Seq. 77 | KIAA1199 (CEMIP) |
| Seq. 78 | KLF2 |
| Seq. 79 | KLF4 |
| Seq. 80 | KLF6 |
| Seq. 81 | KRT19 |
| Seq. 82 | LECT2 |
| Seq. 83 | LEF1 |
| Seq. 84 | LGMN |
| Seq. 85 | LGR5 |
| Seq. 86 | MIF |
| Seq. 87 | MXI1 |
| Seq. 88 | MYC |
| Seq. 89 | MYCN |
| Seq. 90 | MYLK |
| Seq. 91 | MYOD1 |
| Seq. 92 | NDUFV3 |
| Seq. 93 | NKD1 |
| Seq. 94 | NKX2-2 |

Sequence Listing:

| Seq. No. | Gene: |
|---|---|
| Seq. 95 | NKX2-8 |
| Seq. 96 | NOS3 |
| Seq. 97 | NRIP1 |
| Seq. 98 | OAT |
| Seq. 99 | PCK1 |
| Seq. 100 | PDK4 |
| Seq. 101 | PGR |
| Seq. 102 | PISD |
| Seq. 103 | PITRM1 |
| Seq. 104 | POMC |
| Seq. 105 | PPARG |
| Seq. 106 | PPARGC1A |
| Seq. 107 | PPM1D |
| Seq. 108 | PRDM15 |
| Seq. 109 | PRDX3 |
| Seq. 110 | PTCH1 |
| Seq. 111 | PTCH2 |
| Seq. 112 | PTMA |
| Seq. 113 | RAB34 |
| Seq. 114 | RAG1 |
| Seq. 115 | RAG2 |
| Seq. 116 | RARA |
| Seq. 117 | RBL2 |
| Seq. 118 | REG1B |
| Seq. 119 | RNF43 |
| Seq. 120 | S100A7 |
| Seq. 121 | S100A9 |
| Seq. 122 | SEMA3C |
| Seq. 123 | SEPP1 |
| Seq. 124 | SESN1 |
| Seq. 125 | SGK3 |
| Seq. 126 | SIRT1 |
| Seq. 127 | SLC1A2 |
| Seq. 128 | SLC5A3 |
| Seq. 129 | SMAD4 |
| Seq. 130 | SOD1 |
| Seq. 131 | SOD2 |
| Seq. 132 | SOX9 |
| Seq. 133 | SP5 |
| Seq. 134 | SPP1 |
| Seq. 135 | STK11 |
| Seq. 136 | TBX3 |
| Seq. 137 | TCEA2 |
| Seq. 138 | TCF7L2 |
| Seq. 139 | TDGF1 |
| Seq. 140 | TFF1 |
| Seq. 141 | TLE4 |
| Seq. 142 | TNFSF10 |
| Seq. 143 | TOM1 |
| Seq. 144 | TRIM25 |
| Seq. 145 | TSC22D1 |
| Seq. 146 | TXNIP |
| Seq. 147 | WISP2 |
| Seq. 148 | XBP1 |
| Seq. 149 | ZNRF3 |
| Seq. 150 | SERPINE1 |
| Seq. 151 | PDZK1 |

TABLE 16

Oligo Sequences for PI3K Target Genes

| Target Gene | Oligo Name | Sequence 5'-3' | SEQ ID NO. |
|---|---|---|---|
| FBXO31 | FBXO32_F1 | GCTGCTGTGGAAGAAACT | 152 |
| FBXO31 | FBXO32_R1 | GCCCTTTGTCTGACAGAATTA | 153 |
| FBXO31 | FBXO32_FAM1 | TGCCAGTACCACTTCTCCGAGC | 154 |
| BCL2L11 | BCL2L11_F1 | CCTTTCTTGGCCCTTGTT | 155 |
| BCL2L11 | BCL2L11_R1 | AAGGTTGCTTTGCCATTTG | 156 |
| BCL2L11 | BCL2L11_FAM1 | TGACTCTCGGACTGAGAAACGCAA | 157 |
| SOD2 | SOD2_F3 | AGCGGCTTCAGCAGATC | 158 |
| SOD2 | SOD2_R1 | GCCTGGAGCCCAGATAC | 159 |
| SOD2 | SOD2_FAM1 | ACTAGCAGCATGTTGAGCCGGG | 160 |
| TNFSF10 | TNFSF10_F1 | CCTGCAGTCTCTCTGTGT | 161 |
| TNFSF10 | TNFSF10_R2 | GCCACTTTTGGAGTACTTGT | 162 |
| TNFSF10 | TNFSF10_FAM1 | TACCAACGAGCTGAAGCAGATGCA | 163 |
| BCL6 | BCL6_F1 | GAGCCGTGAGCAGTTTAG | 164 |
| BCL6 | BCL6_R1 | GATCACACTAAGGTTGCATTTC | 165 |
| BCL6 | BCL6_FAM1 | AAACGGTCCTCATGGCCTGCA | 166 |
| BTG1 | BTG1_F1 | AAGTTTCTCCGCACCAAG | 167 |
| BTG1 | BTG1_R1 | CTGGGAACCAGTGATGTTTAT | 168 |
| BTG1 | BTG1_FAM1 | AGCGACAGCTGCAGACCTTCA | 169 |
| CCNG2 | CCNG2_F1 | ACAGGTTCTTGGCTCTTATG | 170 |
| CCNG2 | CCNG2_R1 | TGCAGTCTTCTTCAACTATTCT | 171 |
| CCNG2 | CCNG2_FAM1 | ACATTTGTCTTGCATTGGAGTCTGT | 172 |
| CDKN1B | CDKN1B_F2 | CGGTTCTGTGGAGCAGACG | 173 |
| CDKN1B | CDKN1B_R1 | CTTCATCAAGCAGTGATGTATCTG | 174 |
| CDKN1B | CDKN1B_P2 | CCTGGCCTCAGAAGACGTCAAAC | 175 |
| BNIP3 | BNIP3_F4 | GATATGGGATTGGTCAAGTCG | 176 |
| BNIP3 | BNIP3_R2 | CGCTCGTGTTCCTCATGCTG | 177 |
| BNIP3 | BNIP3_FAM1 | TTAAACACCCGAAGCGCACGG | 178 |
| GADD45A | GADD45A_F1 | CAGAAGACCGAAAGGATGGA | 179 |
| GADD45A | GADD45A_R1 | GGCACAACACCACGTTATC | 180 |
| GADD45A | GADD45A_FAM1 | ACGAAGCGGCCAAGCTGCTCAA | 181 |
| INSR | INSR_F2 | CTCGGTCATGAAGGGCTTCA | 182 |
| INSR | INSR_R2 | CCGCAGAGAACGGAGGTAG | 183 |
| INSR | INSR_P2 | ACGCTGGTGGTGATGGAGCTGA | 184 |
| MXI1 | MXI1_F2 | CTGATTCCACTAGGACCAGAC | 185 |
| MXI1 | MXI1_R2 | CTCTGTTCTCGTTCCAAATTCTC | 186 |
| MXI1 | MXI1_P2 | CCCGGCACACAACACTTGGTTTGC | 187 |

TABLE 17

Oligo Sequences for Wnt Target Genes

| Target Gene | Oligo Name | Sequence 5'-3' | SEQ ID NO. |
|---|---|---|---|
| AXIN2 | AXIN2_For1 | GACAGTGAGATATCCAGTGATG | 188 |
| AXIN2 | AXIN2_Rev1 | CTTACTGCCCACACGATAAG | 189 |
| AXIN2 | AXIN2_Probe1 | CATGACGGACAGCAGTGTAGATGGA | 190 |
| CD44 | CD44_For1 | CAATGCCTTTGATGGACCAATTA | 191 |
| CD44 | CD44_Rev1 | GGGTAGATGTCTTCAGGATTCG | 192 |
| CD44 | CD44_Probe1 | TGATGGCACCCGCTATGTCCAGAA | 193 |
| LGR5 | LGR5_For1 | ACTTTCCAGCAGTTGCTTAG | 194 |
| LGR5 | LGR5_Rev2 | GGCAAAGTGGAAAATGCATTG | 195 |
| LGR5 | LGR5_Probe1 | TCCGATCGCTGAATTTGGCTTGA | 196 |
| CEMIP (KIAA1199) | CEMIP_For6 | ACATTCCACTGGGAAAATTCTA | 197 |
| CEMIP (KIAA1199) | CEMIP_RevS | GCTTGTCCTTGGCAGAG | 198 |
| CEMIP (KIAA1199) | CEMIP_Probe3 | TACCGGGCTGGCATGATCATAGACA | 199 |
| MYC | MYC_For1 | TTCGGGTAGTGGAAAACCA | 200 |
| MYC | MYC_Rev1 | CATAGTTCCTGTTGGTGAAGC | 201 |
| MYC | MYC_Probe1 | CTCCCGCGACGATGCCCCTCAA | 202 |
| CXCL8 (IL8) | CXCL8_For1 | GGCAGCCTTCCTGATTTCTG | 203 |
| CXCL8 (IL8) | CXCL8_Rev1 | GGTGGAAAGGTTTGGAGTATG | 204 |
| CXCL8 (IL8) | CXCL8_Probe1 | CAGCTCTGTGTGAAGGTGCAGTTT | 205 |
| SOX9 | SOX9_For5 | GACCAGTACCCGCACTT | 206 |
| SOX9 | SOX9_Rev6 | CGCTTCTCGCTCTCGTT | 207 |
| SOX9 | SOX9_P3 | CGCTGGGCAAGCTCTGGAGACT | 208 |
| EPHB3 | EPHB3_For1 | TCACTGAGTTCATGGAAACTG | 209 |
| EPHB3 | EPHB3_Rev1 | GTTCATCTCGGACAGGTACTT | 210 |
| EPHB3 | EPHB3_Probe1 | CCTTCCTCCGGCTCAACGATGGG | 211 |
| RNF43 | RNF43_For1 | GTTACATCAGCATCGGACTTG | 212 |
| RNF43 | RNF43_Rev1 | GAGTCTTCGACCTGGTTCTT | 213 |
| RNF43 | RNF43_Probe1 | AGTCCCTGGGACCCTCTCGATCTTA | 214 |
| TDGF1 | TDGF1_For6 | TCCGCTGCTTTCCTCAG | 215 |
| TDGF1 | TDGF1_Rev6 | GCAGATGCCAACTAGCATAAA | 216 |
| TDGF1 | TDGF1_Probe1 | TACCCGGCTGTGATGGCCTTGTG | 217 |
| ZNRF3 | ZNRF3_For2 | AAGCTGGAACAGCCAGAATT | 218 |
| ZNRF3 | ZNRF3_Rev1 | CATCAAAGATGACTGCAGTAGCT | 219 |
| ZNRF3 | ZNRF3_Probe1 | TCCTAGGCAAGGCCAAGCGAGC | 220 |
| DEFA6 | DEFA6_For3 | AGAGGATGCAAGCTCAAGT | 221 |
| DEFA6 | DEFA6_Rev1 | AATAACAGGACCTTCTGCAATG | 222 |
| DEFA6 | DEFA6_Probe1 | TGGGCTCAACAAGGGCTTTCACTT | 223 |

TABLE 18

Oligo Sequences for ER Target Genes

| Target Gene | Oligo Name | Sequence 5'-3' | SEQ ID NO. |
|---|---|---|---|
| TFF1 | TFF1_F4 | CCCTGGTGCTTCTATCCTAA | 224 |
| TFF1 | TFF1_R4 | ATCCCTGCAGAAGTGTCTAA | 225 |
| TFF1 | TFF1_P4 | ACCATCGACGTCCCTCCAGAA | 226 |
| GREB1 | GREB1_F9 | AAGAGGTTCTTGCCAGATGA | 227 |
| GREB1 | GREB1_R10 | GGAGAATTCCGTGAAGTAACAG | 228 |
| GREB1 | GREB1_P8 | TCTCTGGGAATTGTGTTGGCTGTGGA | 229 |
| PGR | PGR_F3 | TGGCAGATCCCACAGGAGTT | 230 |
| PGR | PGR_R7 | AGCCCTTCCAAAGGAATTGTATTA | 231 |
| PGR | PGR_P7 | AGCTTCAAGTTAGCCAAGAAGAGTTCCTCT | 232 |
| SGK3 | SGK3_F1 | CTGCCAAGAGAATATTTGGTGATAA | 233 |

TABLE 18-continued

Oligo Sequences for ER Target Genes

| Target Gene | Oligo Name | Sequence 5'-3' | SEQ ID NO. |
|---|---|---|---|
| SGK3 | SGK3_R1 | TGGATACCTAACTAGGTTCTGAATG | 234 |
| SGK3 | SGK3_P1 | ACAAAGACGAGCAGGACTAAACGA | 235 |
| PDZK1 | PDZK1_F4 | GCCATGAGGAAGTGGTTGAAA | 236 |
| PDZK1 | PDZK1_R4 | TGCTCAACATGACGCTTGTC | 237 |
| PDZK1 | PDZK1_P1 | AAGCCGTGTCATGTTCCTGCTGGT | 238 |
| IGFBP4 | IGFBP4_F4 | CCAACTGCGACCGCAAC | 239 |
| IGFBP4 | IGFBP4_R3 | GTCTTCCGGTCCACACAC | 240 |
| IGFBP4 | IGFBP4_P3 | CAAGCAGTGTCACCCAGCTCTGGA | 241 |
| NRIP1 | NRIP1_F3 | CCGGATGACATCAGAGCTA | 242 |
| NRIP1 | NRIP1_R3 | AATGCAAATATCAGTGTTCGTC | 243 |
| NRIP1 | NRIP1_P2 | TCTCAGAAAGCAGAGGCTCAGAGCTT | 244 |
| CA12 | CA12_F4 | GGCATTCTTGGCATCTGTATT | 245 |
| CA12 | CA12_R4 | GCTTGTAAATGACTCCCTTGTT | 246 |
| CA12 | CA12_P2 | TGGTGGTGGTGTCCATTTGGCTTT | 247 |
| XBP1 | XBP1_F1 | GGATTCTGGCGGTATTGACT | 248 |
| XBP1 | XBP1_R3 | CATGACTGGGTCCAAGTTGTC | 249 |
| XBP1 | XBP1_P4 | TCAGAGTCTGATATCCTGTTGGGCATTCTG | 250 |
| ERBB2 | ERBB2_F1 | GTTTGAGTCCATGCCCAATC | 251 |
| ERBB2 | ERBB2_R2 | GATCCCACGTCCGTAGAAA | 252 |
| ERBB2 | ERBB2_P1 | CGCCAGCTGTGTGACTGCCTGT | 253 |
| ESR1 | ESR1_F1 | AGCTTCGATGATGGGCTTAC | 254 |
| ESR1 | ESR1_R2 | CCTGATCATGGAGGGTCAAA | 255 |
| ESR1 | ESR1_P1 | CAACTGGGCGAAGAGGGTGCCA | 256 |
| CELSR2 | CELSR2_F2 | GGTCCGGAAAGCACTCAA | 257 |
| CELSR2 | CELSR2_R2 | TCCGTAGGGCTGGTACA | 258 |
| CELSR2 | CELSR2_P2 | TCCTACAACTGCCCCAGCCCTA | 259 |

TABLE 19

Oligo Sequences for HH Target Genes

| Target Gene | Oligo Name | Sequence 5'-3' | SEQ ID NO. |
|---|---|---|---|
| GLI1 | GLI1_F6 | CAGTACATGCTGGTGGTTCAC | 260 |
| GLI1 | GLI1_R6 | TTCGAGGCGTGAGTATGACTT | 261 |
| GLI1 | GLI1_P6 | ACTGGCGAGAAGCCACACAAGTGC | 262 |
| PTCH1 | PTCH1_F10 | CTTCTTCATGGCCGCGTTAAT | 263 |
| PTCH1 | PTCH1_R10 | AATGAGCAGAACCATGGCAAA | 264 |
| PTCH1 | PTCH1_P9 | TCCAGGCAGCGGTAGTAGTGGTGT | 265 |
| PTCH2 | PTCH2_F13 | CTCCACTGCCCACCTAGT | 266 |
| PTCH2 | PTCH2_R11 | CTCCTGCCAGTGCATGAATTT | 267 |
| PTCH2 | PTCH2_P11 | ATCACAGCAGGCAGGCTCCCAATG | 268 |
| CCND2 | CCND2_F2 | ACACCGACAACTCCATCAA | 269 |
| CCND2 | CCND2_R2 | CGCAAGATGTGCTCAATGAA | 270 |
| CCND2 | CCND2_P2 | TGGAGTGGGAACTGGTGGTGCT | 271 |
| IGFBP6 | IGFBP6_F5 | CCCTCCCAGCCCAATTC | 272 |
| IGFBP6 | IGFBP6_R5 | GGGCACGTAGAGTGTTTGA | 273 |
| IGFBP6 | IGFBP6_P2 | TGCCGTAGACATCTGGACTCAGTGCT | 274 |
| MYCN | MycN_F2 | GACACCCTGAGCGATTC | 275 |
| MYCN | MycN_R4 | GAATGTGGTGACAGCCTTG | 276 |
| MYCN | MycN_P3 | TGAAGATGATGAAGAGGAAGATGAAGAGG | 277 |
| FST | FST_F1 | AGCCTATGAGGGAAAGTGTATC | 278 |
| FST | FST_R2 | CCCAACCTTGAAATCCCATAAA | 279 |
| FST | FST_P1 | AGCAAAGTCCTGTGAAGATATCCAGTGCAC | 280 |
| RAB34 | RAB34_F3 | GGGCAGGAGAGGTTCAAATG | 281 |
| RAB34 | RAB34_R3 | CAGCCACTGCTTGGTATGTT | 282 |
| RAB34 | RAB34_P3 | TCTTCAACCTGAATGATGTGGCATCTCTGG | 283 |
| GLI3 | GLI3_F1 | CCTGTACCAATTGATGCCAGAC | 284 |
| GLI3 | GLI3_R2 | CGGATACGTAGGGCTACTAGATAAG | 285 |
| GLI3 | GLI3_P2 | ACGATCCATCTCCGATTCCTCCATTGCA | 286 |
| CFLAR | CFLAR_F3 | GGTGAGGATTTGGATAAATCTGATG | 287 |
| CFLAR | CFLAR_R1 | TCAACCACAAGGTCCAAGAAAC | 288 |
| CFLAR | CFLAR_P2 | ACATGGGCCGAGGCAAGATAAGCAA | 289 |
| S100A7 | S100A7_F1 | CCAGACGTGATGACAAGATTGAG | 290 |
| S100A7 | S100A7_R1 | GCGAGGTAATTTGTGCCCTT | 291 |
| S100A7 | S100A7_P1 | CCCAACTTCCTTAGTGCCTGTGACA | 292 |
| S100A9 | S100A9_F1 | ATTCAAAGAGCTGGTGCGAAA | 293 |
| S100A9 | S100A9_R2 | AGGTCCTCCATGATGTGTTCT | 294 |
| S100A9 | S100A9_P2 | CTGCAAAATTTTCTCAAGAAGGAGAATAAGAATG | 295 |

TABLE 20

Oligo Sequences for Reference Genes

| Reference Gene | Oligo Name | Sequence 5'-3' | SEQ ID NO. |
|---|---|---|---|
| ACTB | Hum_BACT_F1 | CCAACCGCGAGAAGATGA | 296 |
| ACTB | Hum_BACT_R1 | CCAGAGGCGTACAGGGATAG | 297 |

TABLE 20-continued

Oligo Sequences for Reference Genes

| Reference Gene | Oligo Name | Sequence 5'-3' | SEQ ID NO. |
|---|---|---|---|
| ACTB | Hum_BACT_P1 | CCATGTACGTTGCTATCCAGGCT | 298 |
| POLR2A | Hum_POLR2A_F1 | AGTCCTGAGTCCGGATGAA | 299 |
| POLR2A | Hum_POLR2A_R1 | CCTCCCTCAGTCGTCTCT | 300 |
| POLR2A | Hum_POLR2A_P1 | TGACGGAGGGTGGCATCAAATACC | 301 |
| PUM1 | Hum_PUM1_F2 | GCCAGCTTGTCTTCAATGAAAT | 302 |
| PUM1 | Hum_PUM1_R2 | CAAAGCCAGCTTCTGTTCAAG | 303 |
| PUM1 | Hum_PUM1_P1 | ATCCACCATGAGTTGGTAGGCAGC | 304 |
| TBP | Hum_TBP_F1 | GCCAAGAAGAAAGTGAACATCAT | 305 |
| TBP | Hum_TBP_1_R1 | ATAGGGATTCCGGGAGTCAT | 306 |
| TBP | Hum_TBP_P1 | TCAGAACAACAGCCTGCCACCTTA | 307 |
| TUBA1B | K-ALPHA-1_F1 | TGACTCCTTCAACACCTTCTTC | 308 |
| TUBA1B | K-ALPHA-1_R1 | TGCCAGTGCGAACTTCAT | 309 |
| TUBA1B | K-ALPHA-1_FAM1 | CCGGGCTGTGTTTGTAGACTTGGA | 310 |
| ALAS1 | ALAS1_F1 | AGCCACATCATCCCTGT | 311 |
| ALAS1 | ALAS1_R1 | CGTAGATGTTATGTCTGCTCAT | 312 |
| ALAS1 | ALAS1_FAM1 | TTTAGCAGCATCTGCAACCCGC | 313 |
| HPRT1 | Hum_HPRT1_F1 | GAGGATTTGGAAAGGGTGTTTATT | 314 |
| HPRT1 | Hum_HPRT1_R1 | ACAGAGGGCTACAATGTGATG | 315 |
| HPRT1 | Hum_HPRT1_P1 | ACGTCTTGCTCGAGATGTGATGAAG | 316 |
| RPLP0 | Hum_RPLP0_F2 | TAAACCCTGCGTGGCAAT | 317 |
| RPLP0 | Hum_RPLP0_R2 | ACATTTCGGATAATCATCCAATAGTTG | 318 |
| RPLP0 | Hum_RPLP0_P1 | AAGTAGTTGGACTTCCAGGTCGCC | 319 |
| B2M | Hum_B2M_F1 | CCGTGGCCTTAGCTGTG | 320 |
| B2M | Hum_B2M_R1 | CTGCTGGATGACGTGAGTAAA | 321 |
| B2M | Hum_B2M_P1 | TCTCTCTTTCTGGCCTGGAGGCTA | 322 |
| TPT1 | TPT1_F_PACE | AAATGTTAACAAATGTGGCAATTAT | 323 |
| TPT1 | TPT1_R_PACE | AACAATGCCTCCACTCCAAA | 324 |
| TPT1 | TPT1_P_PACE | TCCACACAACACCAGGACTT | 325 |
| EEF1A1 | EEF1A1_F_PACE | TGAAAACTACCCCTAAAAGCCA | 326 |
| EEF1A1 | EEF1A1_R_PACE | TATCCAAGACCCAGGCATACT | 327 |
| EEF1A1 | EEF1A1_P_PACE | TAGATTCGGGCAAGTCCACCA | 328 |
| RPL41 | RPL41_F_PACE | AAGATGAGGCAGAGGTCCAA | 329 |
| RPL41 | RPL41_R_PACE | TCCAGAATGTCACAGGTCCA | 330 |
| RPL41 | RPL41_P_PACE | TGCTGGTACAAGTTGTGGGA | 331 |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11640845B2). An electronic copy of the "Sequence Listing" will also be available from the USPTO upon request and payment of the fee set forth in 37 CFR 1.19(b)(3).

The invention claimed is:

1. A method for administering a course of treatment to a subject in response to an assigned risk of breast cancer for that subject, comprising:
   a. calculating an activity level of a phosphatidylinositide 3-kinase (PI3K) signaling pathway in a sample isolated from a subject, wherein the PI3K cellular signaling pathway activity is calculated by:
      i. calculating an activity level of a PI3K transcription factor element in the sample, wherein the PI3K transcription factor element comprises a FOXO family member, and wherein the activity level of the PI3K transcription factor element in the sample is calculated by:
         1. obtaining, by using at least one of Polymerase Chain Reaction (PCR), a microarray technique, and RNA-sequencing, data on the expression levels of at least three PI3K target genes derived from the sample, wherein the PI3K transcription factor controls transcription of the at least three PI3K target genes,
         2. calculating the activity level of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level the PI3K transcription factor element; and,
      ii. calculating the activity level of the PI3K cellular signaling pathway in the sample based on the calculated activity level of the PI3K transcription factor element in the sample; and, b. calculating an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity level of the at least one additional cellular signaling pathway is calculated by:
  i. calculating an activity level of a transcription factor element from the at least one additional cellular signaling pathway in the sample, wherein the Wnt signaling pathway transcription factor element comprises (3-catenin/TCF4, the ER signaling pathway transcription factor element comprises an ERα dimer, and the HH signaling pathway transcription factor element comprises a GLI family member, and wherein the activity level of the transcription factor element of the at least one additional cellular signaling pathway is calculated by:
    1. obtaining, by using at least one of Polymerase Chain Reaction (PCR), a microarray technique, and RNA-sequencing, data on the expression levels of at least three target genes of the at least one additional cellular signaling pathway derived from the sample, wherein the transcription factor element of the at least one additional cellular signaling pathway controls transcription of the at least three target genes of the at least one additional cellular signaling pathway,
    2. calculating the activity level of the transcription factor element of the at least one additional cellular signaling pathway in the sample using a calibrated pathway model, wherein the calibrated pathway model compares the expression levels of the at least three target genes from the at least one additional cellular signaling pathway in the sample with expression levels of the at least three target genes from the at least one additional cellular signaling pathway in the calibrated pathway model which define an activity level of the transcription factor element of the at least one additional cellular signaling pathway; and,
  ii. calculating the activity level of the at least one additional cellular signaling pathway in the sample based on the calculated activity level of the transcription factor element of the at least one additional cellular signaling pathway in the sample; and,
c. calculating a risk score using a calibrated Multi-Pathway Score (MPS) model, wherein the calibrated MPS model compares the calculated activity level of the PI3K cellular signaling pathway and the calculated activity level of the at least one additional cellular signaling pathway in the sample with an activity level of a PI3K cellular signaling pathway and activity level of the at least one additional cellular signaling pathway determinative of the occurrence of a clinical event, wherein the calculated activity of the PI3K cellular signaling pathway is increased in the sample and the calculated activity of the at least one additional cellular signaling pathway is increased in the sample, and wherein the calibrated MPS model thus calculates a high risk score, and wherein calculating the risk score using the calibrated MPS model comprises the formula $MPS = w_p \cdot P_p + w_x \cdot P_x$, wherein $P_p$ is the calculated activity of the PI3K cellular signaling pathway and $w_p$ is a weighting coefficient representing a correlation between the activity of the PI3K cellular signaling pathway and the risk of the clinical event occurring; and wherein $P_x$ is the calculated activity of the at least one additional cellular signaling pathway, and $w_x$ is a weighting coefficient representing a correlation between the activity of the at least one additional cellular signaling pathway and the risk of the clinical event occurring;

d. assigning a high risk of experiencing the clinical event associated with a disease within a defined period of time based on the calculated high risk score, wherein the disease is breast cancer;

e. prescribing a course of treatment to decrease the risk of the clinical event occurring based on the assigned high risk of experiencing the clinical event, wherein the course of treatment is configured to inhibit the PI3K cellular signaling pathway and/or the at least one additional cellular signaling pathway; and f. administering the prescribed course of treatment to the subject to inhibit the PI3K cellular signaling pathway and/or the at least one additional cellular signaling pathway; wherein the clinical event is death.

2. The method of claim 1, wherein calculating the risk score using the calibrated MPS model comprises the formula:

$$MPS = w_p \cdot P_p + w_w \cdot P_w + w_e \cdot P_e + w_h \cdot P_h$$

wherein $P_p$, $P_w$, $P_e$, and $P_h$ denote the calculated activity of the PI3K cellular signaling pathway, the Wnt cellular signaling pathway, the ER cellular signaling pathway, and the HH cellular signaling pathway respectively; and wherein $w_p$, $w_w$, $w_e$ and $w_h$ are, respectively, weighting coefficients representing a correlation between the activity of the PI3K cellular signaling pathway and the risk of the clinical event occurring, the activity of the Wnt cellular signaling pathway and the risk of the clinical event occurring, the activity of the ER cellular signaling pathway and the risk of the clinical event occurring, and the activity of the HH cellular signaling pathway and the risk of the clinical event occurring.

3. A method of treating a subject suffering from a disease, wherein the disease places the subject at risk of experiencing a clinical event in a defined period of time, comprising:

a. receiving information regarding the risk that the subject will experience a clinical event within a defined period of time associated with the disease, wherein the disease is breast cancer, wherein the risk is determined by:
  i. calculating an activity level of a PI3K cellular signaling pathway in a sample isolated from the subject, wherein the PI3K cellular signaling pathway activity is calculated by:
    1. calculating an activity level of a PI3K transcription factor element in the sample, wherein the PI3K transcription factor element comprises a FOXO family member, and wherein the activity level of the PI3K transcription factor element in the sample is calculated by:
      a. obtaining, by using at least one of Polymerase Chain Reaction (PCR), a microarray technique, and RNA-sequencing, data on the expression levels of at least three PI3K target genes derived from the sample, wherein the PI3K transcription factor element controls transcription of the at least three PI3K target genes,
      b. calculating the activity level of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and, 2. calculating the activity level of the PI3K cellular signaling pathway in the sample based on the calculated activity level of the PI3K transcription factor element in the sample; and, ii. calculating an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity level of the at least one additional cellular signaling pathway is calculated by:

1. calculating an activity level of a transcription factor element from the at least one additional cellular signaling pathway in the sample, wherein the Wnt signaling pathway transcription factor element comprises β-catenin/TCF4, the ER signaling pathway transcription factor element comprises an ERα dimer, and the HH signaling pathway transcription factor element comprises a GLI family member, and wherein the activity level of the transcription factor element of the at least one additional cellular signaling pathway is calculated by:

a. obtaining, by using at least one of Polymerase Chain Reaction (PCR), a microarray technique, and RNA-sequencing, data on the expression levels of at least three target genes of the at least one additional cellular signaling pathway derived from the sample, wherein the transcription factor element of the at least one additional cellular signaling pathway controls transcription of the at least three target genes of the at least one additional cellular signaling pathway, b. calculating the activity level of the transcription factor element of the at least one additional cellular signaling pathway in the sample using a calibrated pathway model, wherein the calibrated pathway model compares the expression levels of the at least three target genes from the at least one additional cellular signaling pathway in the sample with expression levels of the at least three target genes from the at least one additional cellular signaling pathway in the calibrated pathway model which define an activity level of the transcription factor element of the at least one additional cellular signaling pathway; and, 2. calculating the activity level of the at least one additional cellular signaling pathway in the sample based on the calculated activity level of the transcription factor element of the at least one additional cellular signaling pathway in the sample; and, iii. calculating a risk score using a calibrated Multi-Pathway Score (MPS) model, wherein the calibrated MPS model compares the calculated activity level of the PI3K cellular signaling pathway and the calculated activity level of the at least one additional cellular signaling pathway in the sample with an activity level of a PI3K cellular signaling pathway and activity level of the at least one additional cellular signaling pathway determinative of the occurrence of the clinical event, wherein the calculated activity of the PI3K cellular signaling pathway is increased in the sample and the calculated activity of the at least one additional cellular signaling pathway is increased in the sample, and wherein the calibrated MPS model thus calculates a high risk score, and wherein calculating the risk score using the calibrated MPS model comprises the formula $MPS = w_p \cdot P_p + w_x \cdot P_x$, wherein $P_p$ is the calculated activity of the PI3K cellular signaling pathway and $w_p$ is a weighting coefficient representing a correlation between the activity of the PI3K cellular signaling pathway and the risk of the clinical event occurring, and wherein $P_x$ is the calculated activity of the at least one additional cellular signaling pathway, and $w_x$ is a weighting coefficient representing a correlation between the activity of the at least one additional cellular signaling pathway and the risk of the clinical event occurring; and iv. assigning a high risk of experiencing the clinical event based on the calculated high risk score;

b. prescribing a course of treatment to decrease the risk of the clinical event occurring based on the assigned high risk that the subject will experience the clinical event within the certain period of time, wherein the course of treatment is configured to inhibit the PI3K cellular signaling pathway and/or the at least one additional cellular signaling pathway; and c. administering the prescribed course of treatment to the subject to inhibit the PI3K cellular signaling pathway and/or the at least one additional cellular signaling pathway;

wherein the clinical event is death.

4. The method of claim 3, wherein the risk monotonically increases with an increasing activity level of the PI3K cellular signaling pathway in the sample.

5. The method of claim 4, wherein the prescribed course of treatment administered to the subject comprises a PI3K cellular signaling pathway inhibitor.

6. The method of claim 3, wherein the prescribed course of treatment administered to the subject comprises a Wnt cellular signaling pathway inhibitor.

7. A method of treating a subject suffering from a disease, wherein the disease places the subject at risk of experiencing a clinical event in a defined period of time, comprising:

a. receiving information regarding the risk that the subject will experience a clinical event within a defined period of time associated with the disease, wherein the disease is breast cancer, wherein the risk is determined by:

i. calculating an activity level of a PI3K cellular signaling pathway in a sample isolated from the subject, wherein the PI3K cellular signaling pathway activity is calculated by:

1. calculating an activity level of a PI3K transcription factor element in the sample, wherein the PI3K transcription factor element comprises a FOXO family member, and wherein the activity level of the PI3K transcription factor element in the sample is calculated by:

a. obtaining data on the expression levels of at least three PI3K target genes derived from the sample, wherein the PI3K transcription factor element controls transcription of the at least three PI3K target genes, b. calculating the activity level of the PI3K transcription factor element in the sample using a calibrated pathway model, wherein the calibrated pathway model compares the expression levels of the at least three PI3K target genes in the sample with expression levels of the at least three PI3K target genes in the calibrated pathway model which define an activity level of the PI3K transcription factor element; and, 2. calculating the activity level of the PI3K cellular signaling pathway in the sample based on the calculated activity level of the PI3K transcription factor element in the sample; and, ii. calculating an activity level of at least one additional cellular signaling pathway in the sample, wherein the at least one additional cellular signaling pathway is selected from a Wnt signaling pathway, an estrogen-receptor (ER) signaling pathway, or a hedgehog (HH) signaling pathway in the sample, wherein the activity level of the at least one additional cellular signaling pathway is calculated by:

1. calculating an activity level of a transcription factor element from the at least one additional cellular signaling pathway in the sample, wherein the Wnt signaling pathway transcription factor element comprises β-catenin/TCF4, the ER signaling pathway transcription factor element comprises an ERα dimer, and the HH signaling pathway transcription factor element comprises a GLI family member, and wherein the activity level of the transcription factor element of the at least one additional cellular signaling pathway is calculated by:

a. obtaining data on the expression levels of at least three target genes of the at least one additional cellular signaling pathway derived from the sample, wherein the transcription factor element of the at least one additional cellular signaling pathway controls transcription of the at least three target genes of the at least one additional cellular signaling pathway, b. calculating the activity level of the transcription factor element of the at least one additional cellular signaling pathway in the sample using a calibrated pathway model, wherein the calibrated pathway model compares the expression levels of the at least three target genes from the at least one additional cellular signaling pathway in the sample with expression levels of the at least three target genes from the at least one additional cellular signaling pathway in the calibrated pathway model which define an activity level of the transcription factor element of the at least one additional cellular signaling pathway; and, 2. calculating the activity level of the at least one additional cellular signaling pathway in the sample based on the calculated activity level of the transcription factor element of the at least one additional cellular signaling pathway in the sample; and, iii. calculating a risk score using a calibrated Multi-Pathway Score (MPS) model, wherein the calibrated MPS model compares the calculated activity level of the PI3K cellular signaling pathway and the calculated activity level of the at least one additional cellular signaling pathway in the sample with an activity level of a PI3K cellular signaling pathway and activity level of the at least one additional cellular signaling pathway determinative of the occurrence of the clinical event, wherein the calculated activity of the PI3K cellular signaling pathway is increased in the sample and the calculated activity of the at least one additional cellular signaling pathway is increased in the sample, and wherein the calibrated MPS model thus calculates a high risk score, and wherein calculating the risk score using the calibrated MPS model comprises the formula $MPS = w_p \cdot P_p + w_x \cdot P_x$, wherein $P_p$ is the calculated activity of the PI3K cellular signaling pathway and $w_p$ is a weighting coefficient representing a correlation between the activity of the PI3K cellular signaling pathway and the risk of the clinical event occurring; and wherein $P_x$ is the calculated activity of the at least one additional cellular signaling pathway, and $w_x$ is a weighting coefficient representing a correlation between the activity of the at least one additional cellular signaling pathway and the risk of the clinical event occurring; and iv. assigning a high risk of experiencing the clinical event based on the calculated high risk score;

b. administering a course of treatment to the subject to decrease the risk of the clinical event occurring based on the assigned high risk that the subject will experience the clinical event within the certain period of time, wherein the course of treatment is configured to inhibit the PI3K cellular signaling pathway and/or the at least one additional cellular signaling pathway; and wherein the clinical event is death.

* * * * *